United States Patent
Sun et al.

(10) Patent No.: US 11,657,940 B1
(45) Date of Patent: May 23, 2023

(54) METHODS AND APPARATUS FOR MICROAGENT CONTROL

(71) Applicant: City University of Hong Kong, Hong Kong (CN)

(72) Inventors: Dong Sun, Hong Kong (CN); Dongfang Li, Hong Kong (CN); Liuxi Xing, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 37 days.

(21) Appl. No.: 17/454,077

(22) Filed: Nov. 9, 2021

(51) Int. Cl.
*H01H 47/00* (2006.01)
*H01F 7/06* (2006.01)
*A61N 2/00* (2006.01)

(52) U.S. Cl.
CPC .............. *H01F 7/064* (2013.01); *A61N 2/002* (2013.01)

(58) Field of Classification Search
None
See application file for complete search history.

(56) References Cited

U.S. PATENT DOCUMENTS

| | | | |
|---|---|---|---|
| 10,950,378 B2 | 3/2021 | Zhang et al. | |
| 10,952,803 B2* | 3/2021 | Martel | A61B 6/4258 |
| 2010/0079142 A1* | 4/2010 | Fontius | A61B 34/73 |
| | | | 324/309 |
| 2014/0074062 A1* | 3/2014 | Caffey | A61M 5/1452 |
| | | | 604/82 |
| 2014/0225694 A1 | 8/2014 | Sitti et al. | |
| 2015/0230810 A1* | 8/2015 | Creighton | A61K 41/0028 |
| | | | 604/518 |
| 2016/0263391 A1* | 9/2016 | Tasci | A61B 34/73 |
| 2021/0072229 A1* | 3/2021 | Stadler | B01L 3/502715 |

OTHER PUBLICATIONS

Grzybowski et al.; Dynamic, self-assembled aggregates of magnetized, millimeter-sized objects rotating at the liquid-air interface: Macroscopic, two-dimensional classical artificial atoms and molecules. Phys. Rev. E 64, 011603 (2001).
Wang et al.; Ultrasound Doppler-guided real-time navigation of a magnetic microswarm for active endovascular delivery. Sci. Adv. 7, eabe5914 (2021).
Yu et al.; Pattern generation and motion control of a vortex-like paramagnetic nanoparticle swarm. Int J Rob Res 37, 912-930 (2018).
Crassous et al.; Field-induced assembly of colloidal ellipsoids into well-defined microtubules. Nat. Commun. 5: 5516 (2014).
Xie et al.; Reconfigurable magnetic microrobot swarm: Multimode transformation, locomotion, and manipulation. Sci. Robot. 4, eaav8006 (2019).

(Continued)

Primary Examiner — Stephen W Jackson
(74) Attorney, Agent, or Firm — S&F/WEHRW

(57) ABSTRACT

One embodiment provides a method for controlling a microagent in a workspace. The method includes providing a plurality of magnetic sources and generating a rotating gradient magnetic field by activating the plurality of magnetic sources differently such that a driving force is created to drive the microagent towards an aggregation center in the workspace.

20 Claims, 50 Drawing Sheets
(30 of 50 Drawing Sheet(s) Filed in Color)

(56) References Cited

OTHER PUBLICATIONS

Yang et al.; Statistics-based automated control for a swarm of paramagnetic nanoparticles in 2D space. IEEE Trans. Robot. 36, 254-270 (2019).
Li et al.; Micro/nanorobots for biomedicine: Delivery, surgery, sensing, and detoxification. Sci. Robot. 2, eaam6431 (2017).
Servant et al.; Controlled in vivo swimming of a swarm of bacteria-like microrobotic flagella. Adv. Mater. 27, 2981-2988 (2015).
Garcia-Gradilla et al.; Functionalized Ultrasound-Propelled Magnetically Guided Nanomotors: Toward Practical Biomedical Applications ACS Nano 7, 10, 9232-9240 (2013).

* cited by examiner h = 10 mm h = 20 mm

| $c$ | | x (mm) | | | |
|---|---|---|---|---|---|
| | | -7 | -6 | -5 | -4 |
| y (mm) | -7 | 1,1.81,1.79,1 | 1,1.8,1.68,1 | 1,1.8,1.57,1 | 1,1.8,1.46,1 |
| | -6 | 1,1.69,1.79,1 | 1,1.69,1.68,1 | 1,1.69,1.57,1 | 1,1.69,1.46,1 |
| | -5 | 1,1.58,1.79,1 | 1,1.58,1.68,1 | 1,1.58,1.57,1 | 1,1.57,1.46,1 |
| | -4 | 1,1.47,1.78,1 | 1,1.47,1.67,1 | 1,1.46,1.56,1 | 1,1.46,1.45,1 |
| | -3 | 1,1.36,1.78,1 | 1,1.35,1.67,1 | 1,1.35,1.56,1 | 1,1.35,1.45,1 |
| | -2 | 1,1.24,1.78,1 | 1,1.24,1.67,1 | 1,1.24,1.56,1 | 1,1.24,1.45,1 |
| | -1 | 1,1.13,1.78,1 | 1,1.13,1.67,1 | 1,1.13,1.55,1 | 1,1.12,1.44,1 |
| | 0 | 1,1.02,1.77,1 | 1,1.02,1.66,1 | 1,1.01,1.55,1 | 1,1.01,1.44,1 |
| | 1 | 1,1,1.77,1.1 | 1,1,1.66,1.1 | 1,1,1.55,1.1 | 1,1,1.44,1.1 |
| | 2 | 1,1,1.77,1.21 | 1,1,1.66,1.21 | 1,1,1.55,1.21 | 1,1,1.44,1.22 |
| | 3 | 1,1,1.76,1.32 | 1,1,1.65,1.32 | 1,1,1.54,1.33 | 1,1,1.43,1.33 |
| | 4 | 1,1,1.76,1.43 | 1,1,1.65,1.44 | 1,1,1.54,1.44 | 1,1,1.43,1.44 |
| | 5 | 1,1,1.76,1.55 | 1,1,1.65,1.55 | 1,1,1.54,1.55 | 1,1,1.43,1.55 |
| | 6 | 1,1,1.76,1.66 | 1,1,1.65,1.66 | 1,1,1.54,1.66 | 1,1,1.42,1.67 |
| | 7 | 1,1,1.75,1.77 | 1,1,1.64,1.77 | 1,1,1.53,1.78 | 1,1,1.42,1.78 |

| $c$ | | x (mm) | | | |
|---|---|---|---|---|---|
| | | -3 | -2 | -1 | 0 |
| y (mm) | -7 | 1,1.8,1.35,1 | 1,1.79,1.24,1 | 1,1.79,1.13,1 | 1,1.79,1.02,1 |
| | -6 | 1,1.68,1.35,1 | 1,1.68,1.24,1 | 1,1.68,1.13,1 | 1,1.68,1.02,1 |
| | -5 | 1,1.57,1.35,1 | 1,1.57,1.23,1 | 1,1.57,1.12,1 | 1,1.56,1.01,1 |
| | -4 | 1,1.46,1.34,1 | 1,1.46,1.23,1 | 1,1.45,1.12,1 | 1,1.45,1.01,1 |
| | -3 | 1,1.35,1.34,1 | 1,1.34,1.23,1 | 1,1.34,1.12,1 | 1,1.34,1.01,1 |
| | -2 | 1,1.23,1.34,1 | 1,1.23,1.23,1 | 1,1.23,1.12,1 | 1,1.23,1.01,1 |
| | -1 | 1,1.12,1.33,1 | 1,1.12,1.22,1 | 1,1.12,1.11,1 | 1,1.11,1,1 |
| | 0 | 1,1.01,1.33,1 | 1,1.01,1.22,1 | 1,1,1.11,1 | 1,1,1,1 |
| | 1 | 1,1,1.33,1.11 | 1,1,1.22,1.11 | 1,1,1.11,1.11 | 1,1,1,1.11 |
| | 2 | 1,1,1.33,1.22 | 1,1,1.22,1.22 | 1,1,1,1.22 | 1.01,1,1,1.23 |
| | 3 | 1,1,1.32,1.33 | 1,1,1.21,1.33 | 1,1,1,1.34 | 1.01,1,1,1.34 |
| | 4 | 1,1,1.32,1.44 | 1,1,1.21,1.45 | 1,1,1,1.45 | 1.01,1,1,1.45 |
| | 5 | 1,1,1.32,1.56 | 1,1,1.21,1.56 | 1,1,1,1.56 | 1.01,1,1,1.56 |
| | 6 | 1,1,1.31,1.67 | 1,1,1.2,1.67 | 1,1,1.09,1.67 | 1.02,1,1,1.68 |
| | 7 | 1,1,1.31,1.78 | 1,1,1.2,1.78 | 1,1,1.09,1.79 | 1.02,1,1,1.79 |

Figure 9

| $c$ | | x (mm) | | | |
|---|---|---|---|---|---|
| | | 1 | 2 | 3 | 4 |
| y (mm) | -7 | 1.09,1.79,1,1 | 1.2,1.78,1,1 | 1.31,1.78,1,1 | 1.42,1.78,1,1 |
| | -6 | 1.09,1.67,1,1 | 1.2,1.67,1,1 | 1.31,1.67,1,1 | 1.42,1.67,1,1 |
| | -5 | 1.1,1.56,1,1 | 1.21,1.56,1,1 | 1.32,1.56,1,1 | 1.43,1.55,1,1 |
| | -4 | 1.1,1.45,1,1 | 1.21,1.45,1,1 | 1.32,1.44,1,1 | 1.43,1.44,1,1 |
| | -3 | 1.1,1.34,1,1 | 1.21,1.33,1,1 | 1.32,1.33,1,1 | 1.43,1.33,1,1 |
| | -2 | 1.1,1.22,1,1 | 1.22,1.22,1,1 | 1.33,1.22,1,1 | 1.44,1.22,1,1 |
| | -1 | 1.11,1.11,1,1 | 1.22,1.11,1,1 | 1.33,1.11,1,1 | 1.44,1.1,1,1 |
| | 0 | 1.11,1,1,1 | 1.22,1,1,1.01 | 1.33,1,1,1.01 | 1.44,1,1,1.01 |
| | 1 | 1.11,1,1,1.12 | 1.22,1,1,1.12 | 1.33,1,1,1.12 | 1.44,1,1,1.12 |
| | 2 | 1.12,1,1,1.23 | 1.23,1,1,1.23 | 1.34,1,1,1.23 | 1.45,1,1,1.24 |
| | 3 | 1.12,1,1,1.34 | 1.23,1,1,1.34 | 1.34,1,1,1.35 | 1.45,1,1,1.35 |
| | 4 | 1.12,1,1,1.45 | 1.23,1,1,1.46 | 1.34,1,1,1.46 | 1.45,1,1,1.46 |
| | 5 | 1.12,1,1,1.57 | 1.23,1,1,1.57 | 1.35,1,1,1.57 | 1.46,1,1,1.57 |
| | 6 | 1.13,1,1,1.68 | 1.24,1,1,1.68 | 1.35,1,1,1.68 | 1.46,1,1,1.69 |
| | 7 | 1.13,1,1,1.79 | 1.24,1,1,1.79 | 1.35,1,1,1.8 | 1.46,1,1,1.8 |

| $c$ | | x (mm) | | |
|---|---|---|---|---|
| | | 5 | 6 | 7 |
| y (mm) | -7 | 1.53,1.78,1,1 | 1.64,1.77,1,1 | 1.75,1.77,1,1 |
| | -6 | 1.54,1.66,1,1 | 1.65,1.66,1,1 | 1.76,1.66,1,1 |
| | -5 | 1.54,1.55,1,1 | 1.65,1.55,1,1 | 1.76,1.55,1,1 |
| | -4 | 1.54,1.44,1,1 | 1.65,1.44,1,1 | 1.76,1.43,1,1 |
| | -3 | 1.54,1.33,1,1 | 1.65,1.32,1,1 | 1.76,1.32,1,1 |
| | -2 | 1.55,1.21,1,1 | 1.66,1.21,1,1 | 1.77,1.21,1,1 |
| | -1 | 1.55,1.1,1,1 | 1.66,1.1,1,1 | 1.77,1.1,1,1 |
| | 0 | 1.55,1,1,1.01 | 1.66,1,1,1.02 | 1.77,1,1,1.02 |
| | 1 | 1.55,1,1,1.13 | 1.67,1,1,1.13 | 1.78,1,1,1.13 |
| | 2 | 1.56,1,1,1.24 | 1.67,1,1,1.24 | 1.78,1,1,1.24 |
| | 3 | 1.56,1,1,1.35 | 1.67,1,1,1.35 | 1.78,1,1,1.36 |
| | 4 | 1.56,1,1,1.46 | 1.67,1,1,1.47 | 1.78,1,1,1.47 |
| | 5 | 1.57,1,1,1.58 | 1.68,1,1,1.58 | 1.79,1,1,1.58 |
| | 6 | 1.57,1,1,1.69 | 1.68,1,1,1.69 | 1.79,1,1,1.69 |
| | 7 | 1.57,1,1,1.8 | 1.68,1,1,1.8 | 1.79,1,1,1.81 |

METHODS AND APPARATUS FOR MICROAGENT CONTROL

FIELD OF THE INVENTION

The present invention relates to microagent control, and more particularly to controlling of migration of a microagent, or a swarm of microagents.

BACKGROUND

Microagents, such as microparticles, microrobots, etc. are useful in many industrial applications. For example, precision targeted therapy is a modern medical treatment that can precisely locate a lesion in a human body and deliver drugs or therapeutic cells to interact with it. The used drugs or cells can identify specific genes, proteins, and environmental characteristics (pH values, temperature, osmotic pressure, etc.) that are involved in the lesion tissue. Using microagents as carriers to deliver these drugs or cells has been commonly recognized as a promising solution, and its feasibility has been verified in recent years. Microagents can be small particles in the range of a few microns or less, which can protect the drug from degradation and control drug release over a certain period of time; or relatively large microrobots ranging from tens to hundreds of microns, which can deliver cells on the basis of appropriately designed three-dimensional (3 D) structures to facilitate loading, adhesion, transport, and release of functional cells. As another example, microrobots may be used in harsh industrial environment that is dangerous for human beings or is difficult to access. In such harsh applications, microrobots may be expected to migrate towards a desirable site or area to perform certain tasks.

New methods and apparatus that assist in advancing technological needs and industrial applications in microagent control are desirable.

SUMMARY OF THE INVENTION

One embodiment provides a method for controlling a microagent in a workspace. The method includes providing a plurality of magnetic sources and generating a rotating gradient magnetic field by activating the plurality of magnetic sources differently such that a driving force is created to drive the microagent towards an aggregation center in the workspace.

Other example embodiments are discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 shows a mapping relationship between aggregation center position g(x, y) and c=($c_1$, $c_2$, $c_3$, $c_4$) in accordance with certain embodiments.

DETAILED DESCRIPTION

Figure 1:
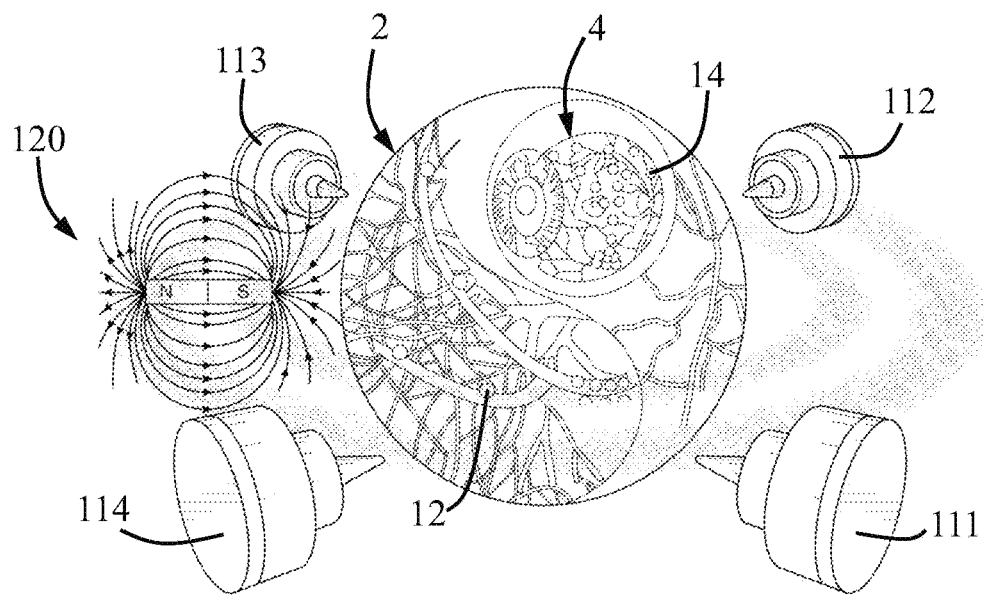
FIG. 1 illustrates rotating gradient magnetic field actuation in accordance with certain embodiments.

Example embodiments relate to methods and apparatus for microagent control by which a microagent or a swarm of microagents can migrate towards a desirable site or area effectively.

Take an application of microagent in therapy as an example. The success of targeted therapy largely depends on accuracy of delivery to a targeted lesion. To overcome limitations of the carrying capacity of a single microagent, a group of microagents (i.e., microagent swarm) must be used for delivery, which puts forward a high requirement for the actuation and control. The microagent swarm can be triggered and actuated by external field stimuli, such as ultrasound, optical tweezers, electricity, and magnetic actuation. Among these methods, electromagnetic actuation is popular for in-vivo applications for its advantages of non-invasive and good control ability, minimal damage to tissues, and insensitivity to biological substances. In this regard, two typical magnetic drive methods are used. One is based on torque-driven magnetic field, and the other is based on gradient magnetic field. The torque-driven magnetic field rotates microagents by first imposing a torque on them, and then converts the rotation into a driving force on the basis of the specifically designed shape and structure of microagents. Such a torque-driven mechanism has a strong driving capacity but limits the shape of the designed microagents. The gradient-based magnetic field can generate a magnetic force directly to drive microagents. The method liberates the constraint of the microagent shape design but requires a high magnetic field gradient to drive microagents. The imaging methods used for the above two drive mechanisms are limited by low resolution and/or shallow penetration depth, which hinders the application of microagent delivery in the in-vivo environment, especially in small and complex regions, such as tiny cavities or tortuous ducts across the blood circulation system.

Example embodiments solve one or more of the problems associated with the existing methods and systems and provide technical solutions with improved microagent control. With one or more methods and apparatus as described herein, a microagent or a microagent swarm can be effectively controlled and migrate to a desirable site or area.

According to one or more embodiments, a rotating gradient magnetic field is used to transport a microagent or a swarm of microagents to a target site precisely. The rotating gradient magnetic field can be generated by sequentially energizing each of magnetic sources (such as magnetic coils of a gradient-based electromagnetic coil system). Compared with the traditional gradient field drive, under the driving force of the rotating gradient magnetic field, rotation of microagent will reduce viscous resistance and friction of surrounding environment to the microagent, thereby greatly enhancing the motion ability of each microagent. Considering that the gradient magnetic field remains as the main driving force, the shape design of the microagent is unrestricted. The rotating gradient field will produce a volume of high gradient concentrated onto the target site, which attracts the microagent or microagent swarm to automatically converge to the target site from different directions under the action of centripetal force.

According to one or more embodiments, rotating gradient-based magnetic field is used to drive magnetic microswarms as carriers to precisely deliver drugs or cells. A sequentially energized electromagnetic coil system generates an equivalent centripetal force pointing to a target site, which will attract magnetic microswarms to converge to the target site in the lesion tissue from different directions. The target site can be adjustable through changing various factors, such as the current inputs of magnetic coils.

According to one or more embodiments, under a rotating gradient magnetic field, a microagent is driven to rotate while moving forward, thereby reducing the viscous resistance and friction on the microagent and improving its motion ability.

According to one or more embodiments, the microagent control does not rely on any specific trajectory plan and real-time visual guidance for each microagent navigation, which greatly simplifies practical applications.

According to one or more embodiments, a rotating gradient magnetic field is generated to drive different magnetic microagents despite their properties such as size, shape, and material. Further, the microagent control does not rely on the initial distribution density of microagents.

According to one or more embodiments, a rotating gradient magnetic field is used to gather and drive a swarm of magnetic agents, such as microparticles, microrobots, and other agents which can be magnetized, and make them aggregate in a designed target site or area or aggregation position in absence of imaging guide. The aggregation position can be changed by adjusting various factors, such as the input current of the magnetic system. The microagent control is suitable for precision targeted therapy by delivering drugs or therapeutic cells in complex or harsh environments or other industrial applications, such as harsh environment or environment that is difficult to access by human beings.

According to one or more embodiments, for microagent control, electric magnetic coils are used to form a dynamic magnetic field, which is more easily for the generating and adjusting process of the magnetic field by programming input current of the coils when compared with using a permanent magnet to force microagents. The microagent control is based on the principle of creating a zone of attraction in certain position which attracts all the magnetic microswarms. So the microagent control can drive different magnetic microswarms regardless of their properties such as size, shape, and material and does not rely on their distribution density. This is different from traditional methods that require a specific trigger mechanism. The microagent control can drive the microswarms accurately to move to different target positions by adjusting various factors, such as the input current of the coils. The aggregation area moves and attracts the microswarms from its initial position naturally. The control process is simple and can be more easily and effectively achieved than existing methods. No external navigation and feedback methods are needed. The control approach can overcome numerous problems that exist in traditional methods, such as maintaining pattern stability, stochasticity of initial distribution, and navigating in an unpredictable dynamic fluid environment. One or more advantages have been experimentally demonstrated in different microswarm environments including open area environment in chamber, constrained environment in microfluidic chip, and ex-vivo environment in bovine eyeball with different micro swarm agents.

According to one or more embodiments, a rotating magnetic field is generated for microagent control. By adjusting the rotating frequency of the magnetic field, different types of microagents are driven to converge to a produced aggregation center or scatter at different rates. Considering that the aggregation does not depend on mutual attraction of the microagents, there is no specific requirement on the distribution density of the microagents. A numerical model of rotating gradient magnetic field actuation is established, based on which the location of the microagent aggregation can be determined by adjusting the input current of each magnetic source, such as each magnetic coil. The relationship between the current input and the location of the aggregation center is characterized to ensure that the microagents are controllable in the entire workspace.

According to one or more embodiments, the driving ability of a rotating gradient magnetic field to transport microagents to a simulated blood flow environment is investigated. Given that the driving mechanism does not depend on the agent-agent interaction, the aggregation does not depend on the specific characteristics of the microagents, such as size, shape and material. Experiments performed in a microfluidic channel have confirmed that when an aggregation area is created, the majority of microagents passing through the area are firmly attracted by the magnetic field.

According to one or more embodiments, an ex-vivo test is conducted in a bovine eyeball to demonstrate the effectiveness of a rotating gradient magnetic field in driving microagents to a target site. No motion planning is needed for each microagent, and no guidance is required for real-time imaging. The experimental results show that the control method can enrich microagents in complex environments with good performance.

According to one or more embodiments, new actuation mechanism is developed that uses a rotating gradient-based magnetic field to drive magnetic microagents to the target site. By programming a microcontroller unit (MCU) of an actuator to sequentially energize electromagnetic coils, the gradient magnetic field can be rotated, and an equivalent centripetal force is generated on the microagents and converge the microagents to a common target position. By modifying the input currents of coils, the position of aggregation center can be adjusted. Experimental results verify the feasibility of this new magnetic drive mechanism. The effectiveness of the rotating gradient magnetic field is verified in a microfluidic chip network that simulates a vascular environment. The ex-vivo experiment has also been conducted successfully on a bovine eyeball model. The experimental results have confirmed the feasibility of the rotating gradient magnetic field in driving different kinds of microagents to a common site for targeted delivery.

According to one or more embodiments, the magnetic drive mechanism for microagent control is different from existing methods in several aspects. First, unlike the method that uses permanent magnet to force microagents to form a dynamic stable swarm, the rotating gradient magnetic field in accordance with one or more embodiments as described herein can be easily generated and adjusted by only programming the input current of the coil. Second, the rotating gradient magnetic field can drive different magnetic microagents regardless of their properties such as size, shape, and material and does not rely on the distribution density. This is different from many traditional methods that require a specific trigger mechanism. In addition, the generated swarm can have a large size (e.g., at millimeter scale) and be located in the entire workspace. Third, the microagent swarm can accurately move to different target positions by adjusting the input current of magnetic sources, such as coils. The control process is can be easily implanted.

According to one or more embodiments, the microagent control approach can overcome various problems that exist in traditional methods, such as maintaining pattern stability, stochasticity of initial distribution, and navigating in an unpredictable dynamic fluid environment. The experimental results have revealed that the low-density microagents can accumulate in a wide open area and finally form a dynamic equilibrium pattern in a desired aggregation area.

FIG. 1 illustrates a rotating gradient magnetic field actuation in accordance with certain embodiments.

By way of example, FIG. 1 illustrates microagents 12 (For concise, only one microagent is referenced with a sign 12) in blood vessels 2 and microagents 14 (For concise, only one microagent is referenced with a sign 14) on the surface of the retina of an eyeball 4. Magnetic sources 111, 112, 113, and 114 are employed to generate a magnetic field. For concise, only magnetic field 120 is shown for illustrative purpose. By way of example, the magnetic sources have four orthogonal electromagnetic coils. When current flows through a magnetic coil, a static gradient magnetic field with a donut-shaped distribution is generated. By way of example, by sequentially inputting direct current (DC) to each coil, a rotating magnetic field can be created. A microagent or a swarm of magnetic microagents can be excited to migrate or navigate to and accumulate at an aggregation center or target site or target position. The position or location of the aggregation center can be adjusted by changing the input current of the coils.

Figure 2A:
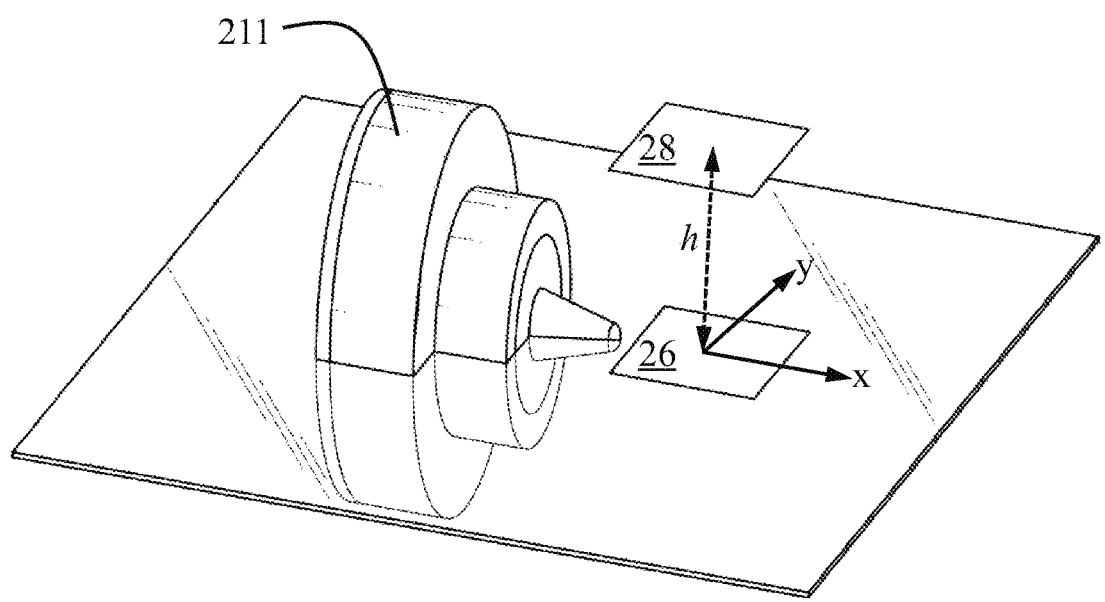
FIG. 2A illustrates a magnetic field generation system in accordance with certain embodiments.

FIG. 2A illustrates a magnetic field generation system. For concise, only a single magnetic source 211 is shown. The magnetic source can be a specific implementation of magnetic sources 111, 112, 113, or 114 with reference to FIG. 1.

By way of example, the magnetic source includes a magnetic coil. FIG. 2A illustrates a reference plane 26 and a working plane 28. The reference plane 26 can be a horizontal plane where point dipoles of magnetic coils are located. The distance between the two planes is denoted by h, which is also height of the working plane 28 relative to the reference plane 26 along a direction perpendicular to the two planes 26, 28. The working plane is also called h-plane in one or more embodiments.

Figure 2B:
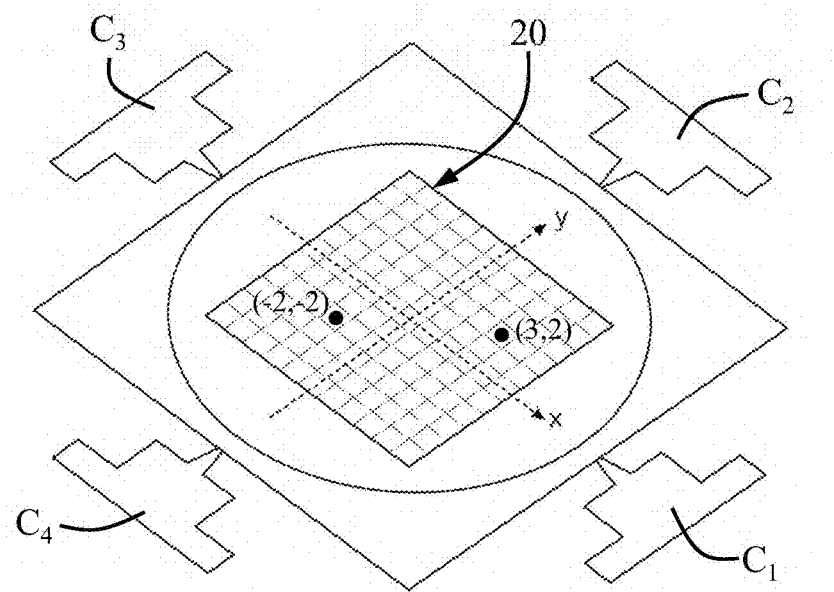
FIG. 2B illustrates a workspace generated by the magnetic field generation system of FIG. 2A.

FIG. 2B illustrates a workspace 20. The workspace is a space where a microagent or a microagent swarm or a majority of a microagent swarm migrates. In reality, the workspace can be a 3 D space, such as substantially having a configuration of a sphere or cuboid. A working plane is a plane passing through the workspace and in parallel with the reference plane. The working plane typically passes through the center of a workspace with which it associates. In one or more embodiments as described herein, for concise, the workspace is illustrated as a two-dimensional (2 D) space, and as such, the workspace and the associated working plane are in a same plane. In the present embodiment, the workspace 20 is illustrated as a square area of 15×15 unit square areas in the working plan and defined by the four magnetic coils $C_1$, $C_2$, $C_3$, and $C_4$.

Figure 3A:
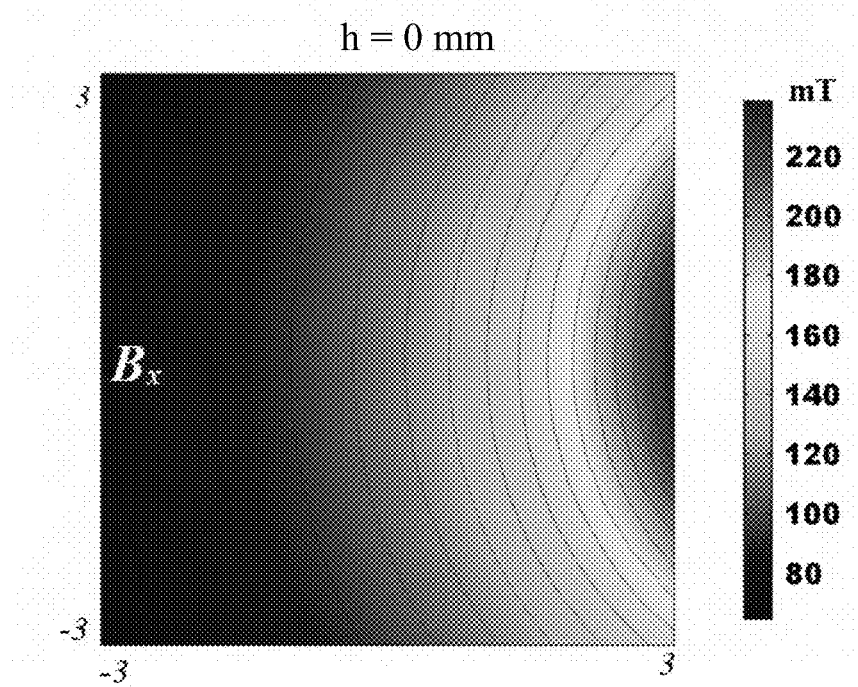
FIG. 3A shows simulation results of magnetic field unit flux density in x direction ($B_x$) generated by a single magnetic coil in a platform with height h=0 in accordance with certain embodiments.
Figure 3B:
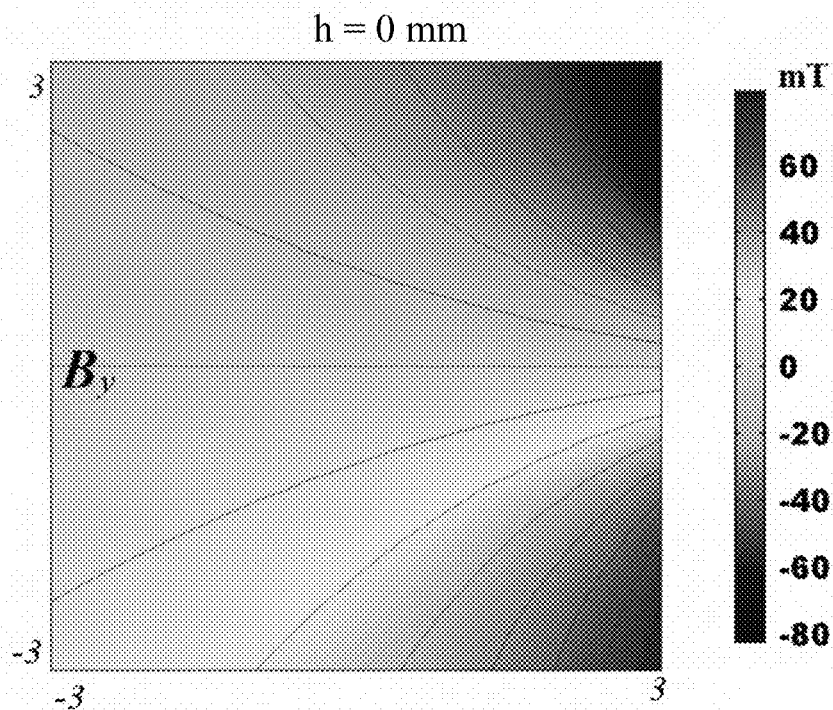
FIG. 3B shows simulation results of magnetic field unit flux density in y direction ($B_y$) generated by a single magnetic coil in a platform with height h=0 in accordance with certain embodiments.
Figure 4A:
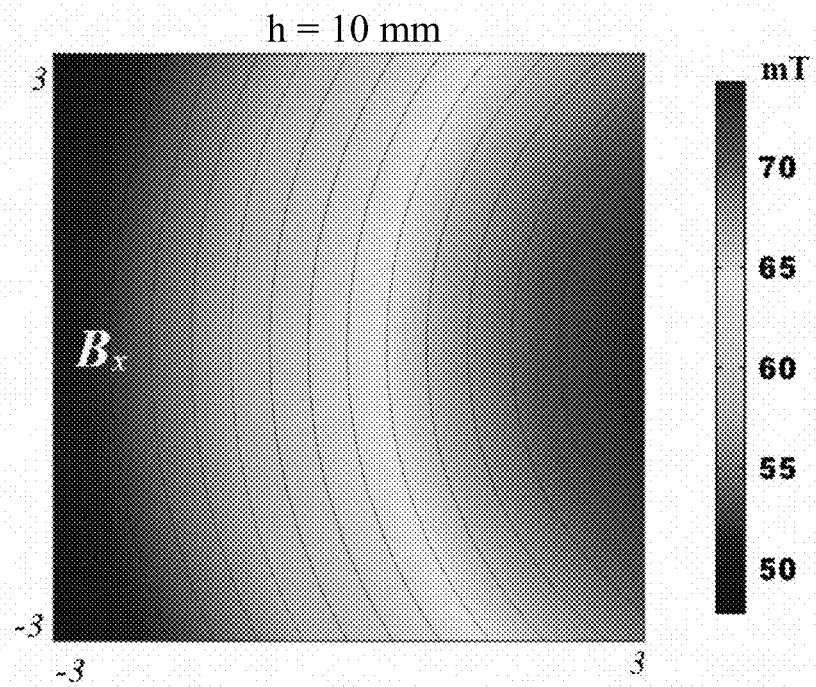
FIG. 4A shows simulation results of magnetic field unit flux density in x direction ($B_x$) generated by a single magnetic coil in a platform with height h=10 in accordance with certain embodiments.
Figure 4B:
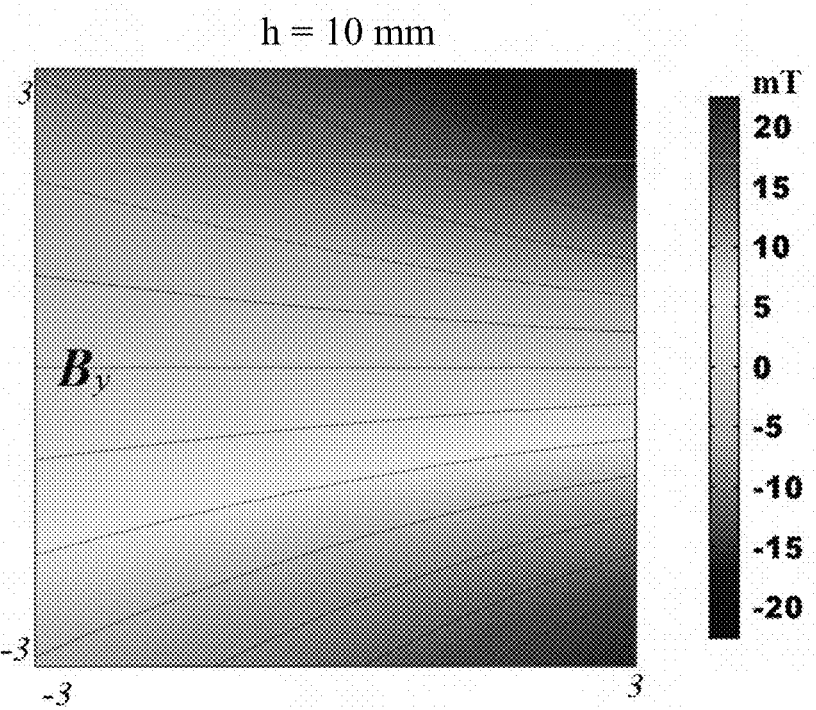
FIG. 4B shows simulation results of magnetic field unit flux density in y direction ($B_y$) generated by a single magnetic coil in a platform with height h=10 in accordance with certain embodiments.
Figure 5A:
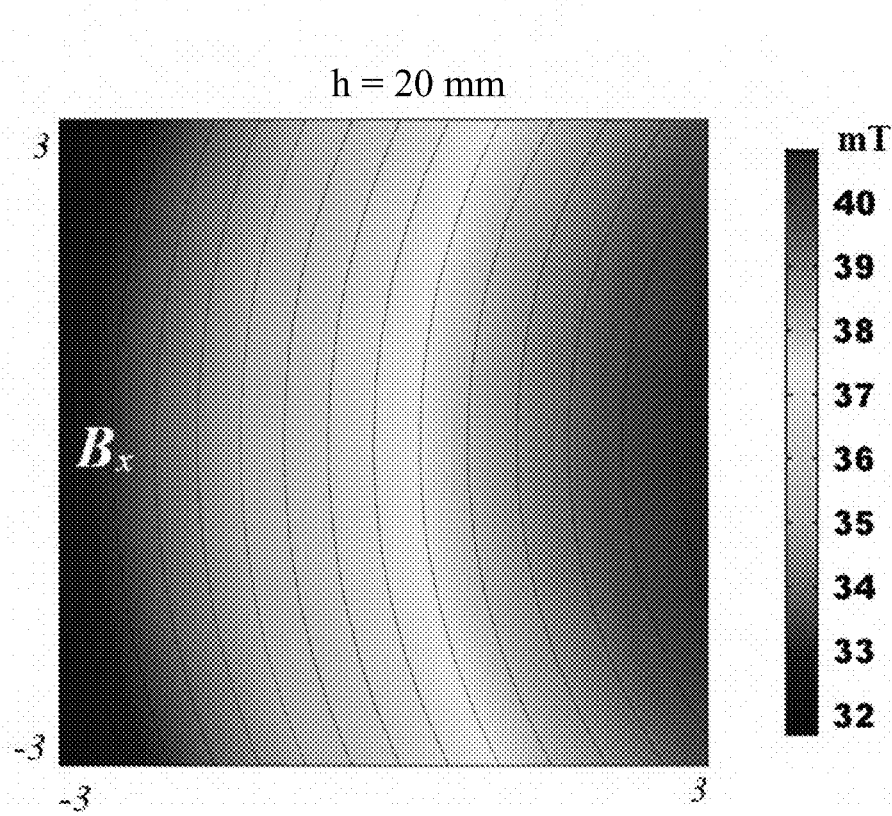
FIG. 5A shows simulation results of magnetic field unit flux density in x direction ($B_x$) generated by a single magnetic coil in a platform with height h=20 in accordance with certain embodiments.
Figure 5B:
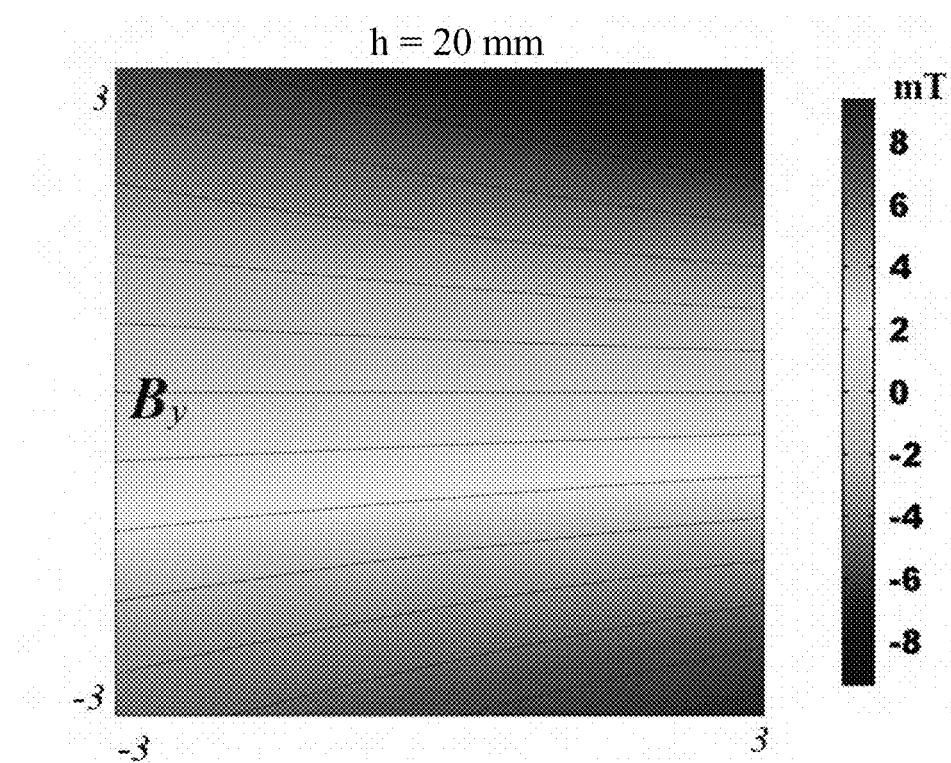
FIG. 5B shows simulation results of magnetic field unit flux density in y direction ($B_y$) generated by a single magnetic coil in a platform with height h=20 in accordance with certain embodiments.
Figure 6A:
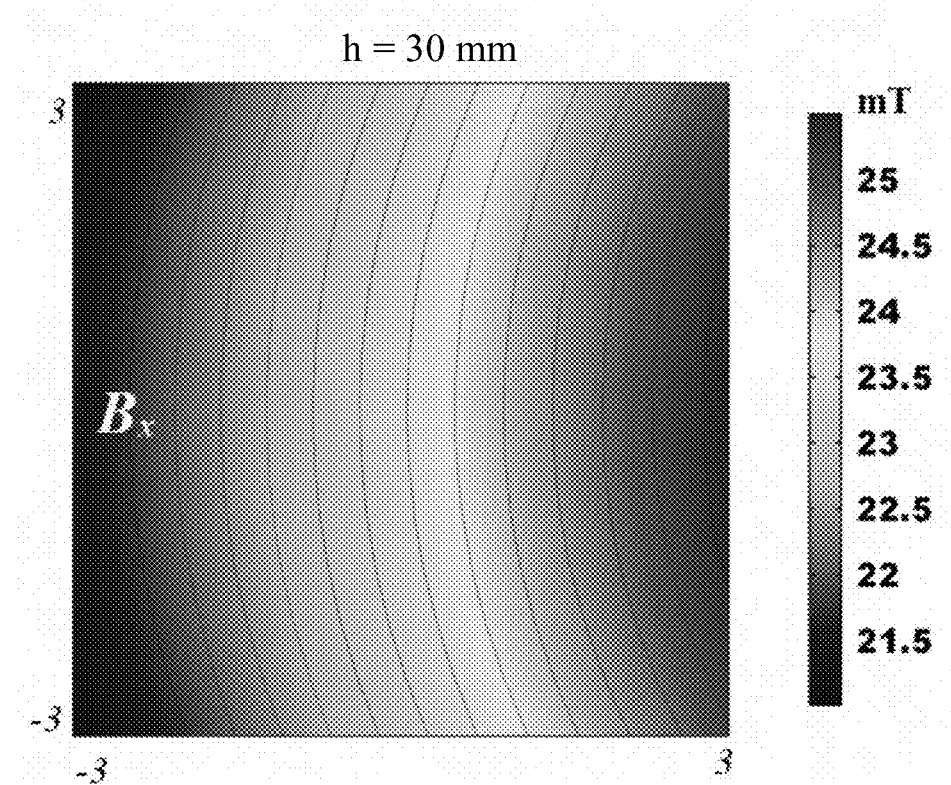
FIG. 6A shows simulation results of magnetic field unit flux density in x direction ($B_x$) generated by a single magnetic coil in a platform with height h=30 in accordance with certain embodiments.
Figure 6B:
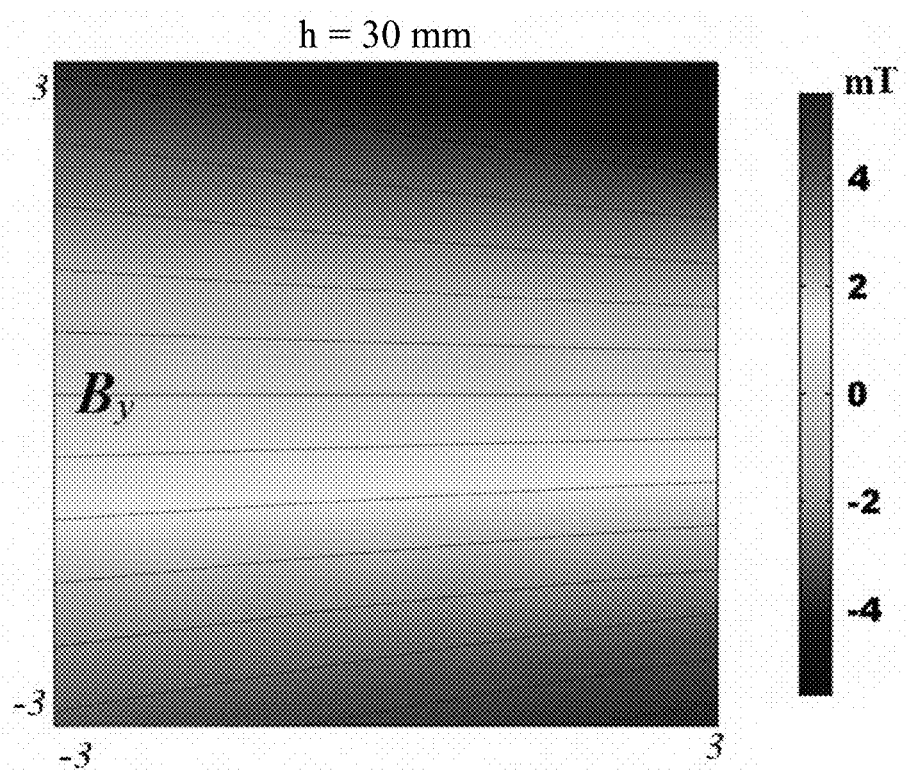
FIG. 6B shows simulation results of magnetic field unit flux density in y direction ($B_y$) generated by a single magnetic coil in a platform with height h=30 in accordance with certain embodiments.

FIGS. 3A-6B shows simulation results of magnetic field unit flux density $B_{unit}(r, h)$ generated by a single magnetic coil in different platforms with different height h. $B_x$ and $B_y$ are the flux density in x and y directions respectively, and h is the height of h-plane relative to a reference plane. FIGS. 3A-3B shows $B_x$ and $B_y$ at h=0 mm (i.e. the working plane and the reference plane are on a same plane) respectively. FIGS. 4A-4B shows $B_x$ and $B_y$ at h=10 mm respectively. FIGS. 5A-5B shows $B_x$ and $B_y$ at h=20 mm respectively. FIGS. 6A-6B shows $B_x$ and $B_y$ at h=30 mm respectively.

In accordance with one or more embodiments, a rotating gradient magnetic field can be generated by activating multiple magnetic sources differently (such as activating the magnetic sources on a different time sequence, with a different current input, etc.) such that a driving force (such as a centripetal force) is created to drive a microagent towards an aggregation center in a workspace. The driving force can also drive a microagent swarm towards an aggregation area.

Figure 7:
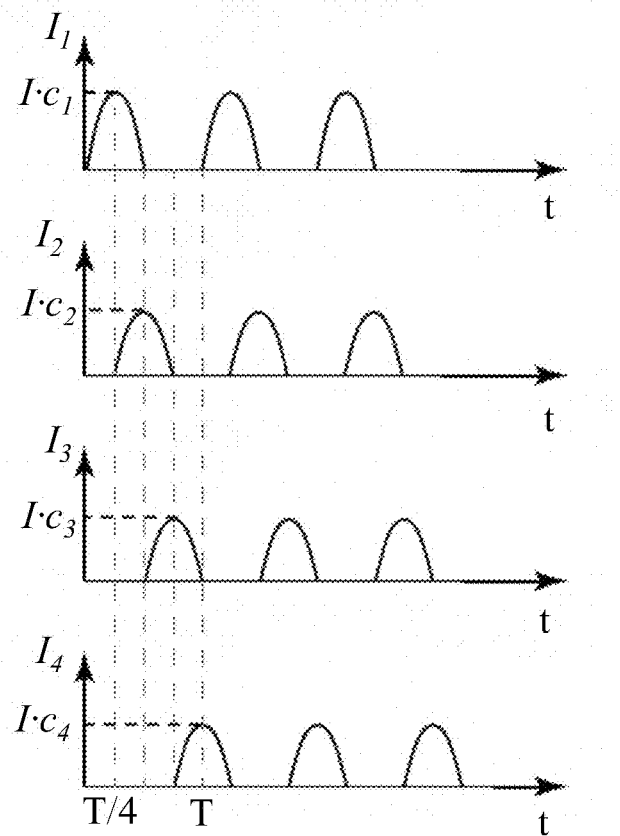
FIG. 7 illustrates a sequential activation for a plurality of magnetic sources in accordance with certain embodiments.

By way of example, FIG. 7 illustrates a sequential activation for a plurality of magnetic sources for generating a centripetal force in accordance with certain embodiments. In the present embodiment, the magnetic sources are illustrated as four magnetic coils that are magnetic coils $C_1$, $C_2$, $C_3$, and $C_4$ respectively with reference to FIG. 2B. The magnetic coils are energized by four DC power sources or power supplies. The current input feeding the magnetic coils are DC input. As illustrated, a sequentially DC input of the coils is performed so as to generated a rotating magnetic field. When applying the sequentially DC input $I_i$, i=1, 2, 3, 4 in the present embodiment, the flux density B(r, h) is then rotated with a frequency f. Denoting I as the current amplitude from the power source, the current of the ith coil is expressed as:

$$I'_i = I \cdot \sin\left(2\pi\left(ft - \frac{i-1}{n}\right)\right) \cdot c_i \quad (1)$$

$$I_i = \begin{cases} I'_i & \text{when } I'_i \geq 0 \\ 0 & \text{when } I'_i < 0 \end{cases}$$

where f and t denote the rotating frequency of the magnetic field and time period respectively. In real-time applications, a current parameter $c_i$ can be introduced to $I_i$ to adjust the current of the ith coil. In this way, the position or location of the aggregation center can be changed. In the present embodiment, I can be adjusted by the power source, and the parameter $c_i$ can be adjusted by a microcontroller unit or controller.

Figure 8A:
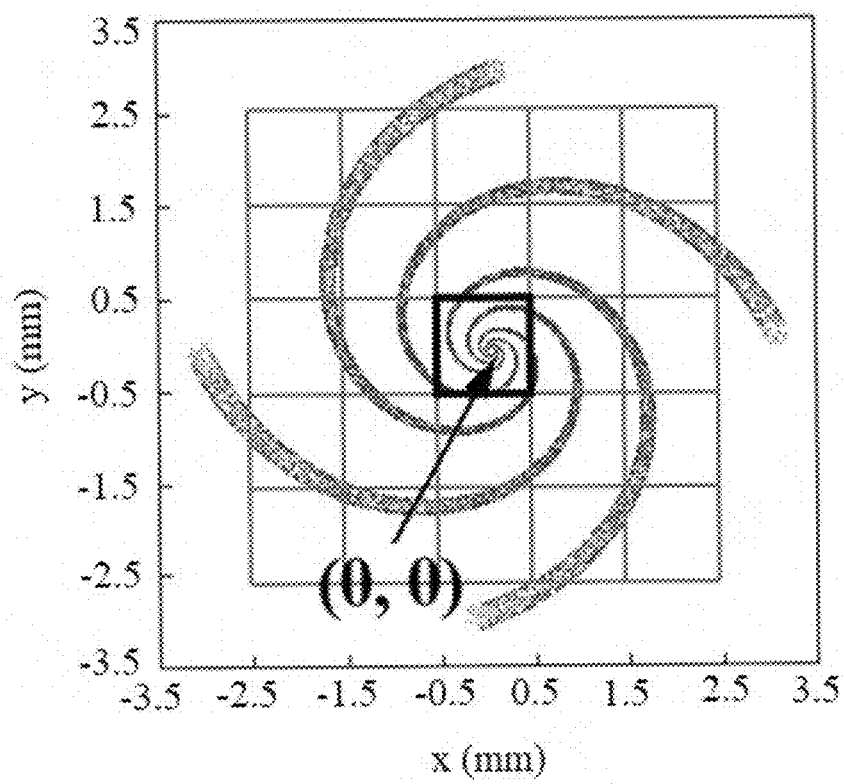
FIG. 8A illustrates motion trajectories of a microagent moving from four directions to an aggregation center under parameter c=(1, 1, 1, 1) in accordance with certain embodiments.

FIGS. 8A-8D illustrate motion trajectories of a microagent moving from four directions to different aggregation centers under different parameter c=($c_1$, $c_2$, $c_3$, $c_4$) in accordance with certain embodiments. The microagent is initially located at (0, 3), (3, 0), (0, −3), (−3, 0). In FIG. 8A, $c_1=c_2=c_3=c_4=1$, under a rotating gradient magnetic field, the microagent converges to a center of the workspace, i.e. (0, 0). The trajectories of the microagent are denoted by dotted lines. It can be seen that the microagent converges to the center from four different positions successfully, which indicates that the rotating magnetic field can produce a centripetal force to attract the microagent to converge to a target position.

Figure 8B:
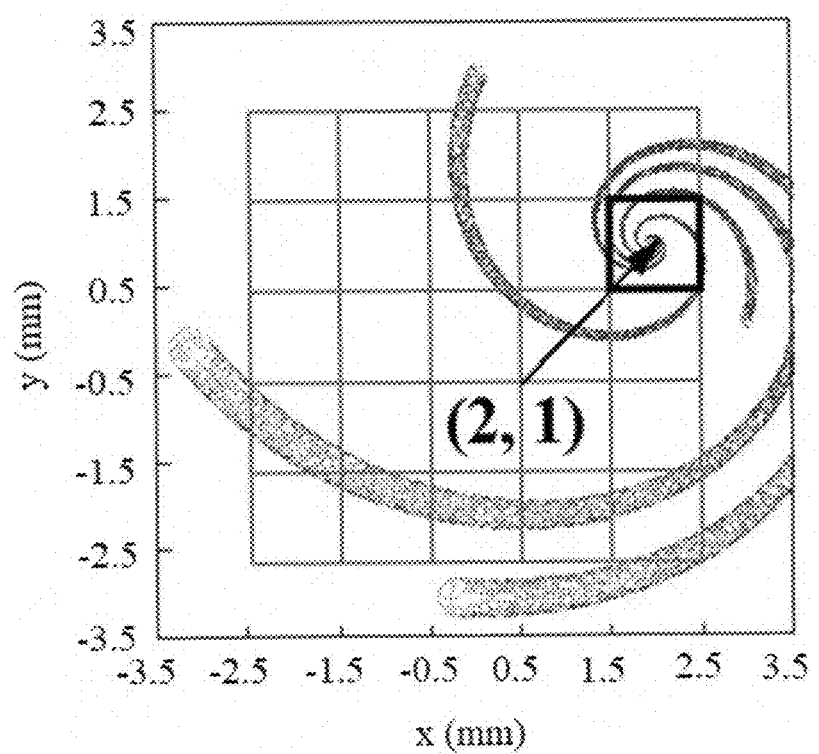
FIG. 8B illustrates motion trajectories of a microagent moving from four directions to an aggregation center under parameter c=(1.22, 1.11, 1, 1) in accordance with certain embodiments.
Figure 8C:
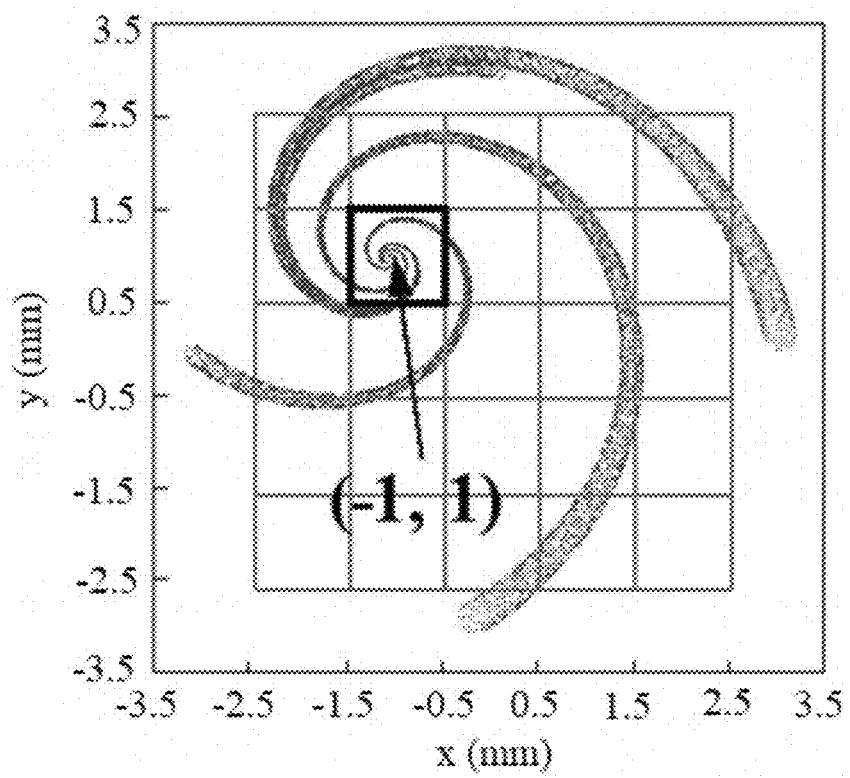
FIG. 8C illustrates motion trajectories of a microagent moving from four directions to an aggregation center under parameter c=(1, 1.12, 1.11, 1) in accordance with certain embodiments.
Figure 8D:
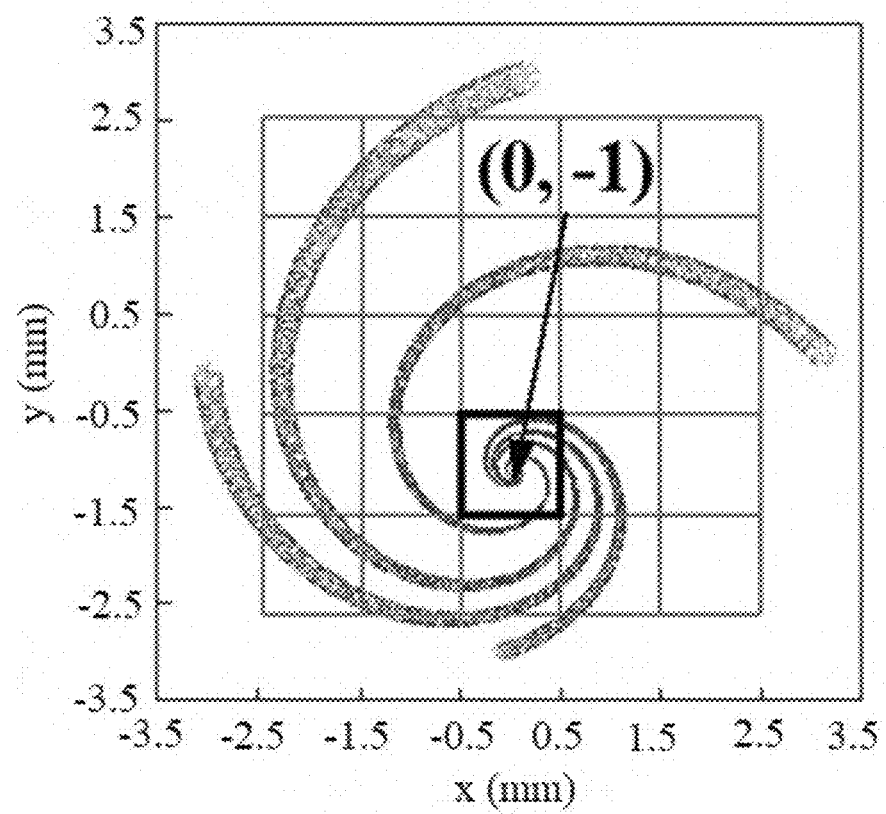
FIG. 8D illustrates motion trajectories of a microagent moving from four directions to an aggregation center under parameter c=(1.01, 1, 1, 1.11) in accordance with certain embodiments.

In FIG. 8B, ($c_1$, $c_2$, $c_3$, $c_4$)=(1.22, 1.11, 1, 1). Under a rotating gradient magnetic field, the microagent converges to (2, 1). In FIG. 8C, ($c_1$, $c_2$, $c_3$, $c_4$)=(1, 1.12, 1.11, 1). Under a rotating gradient magnetic field, the microagent converges to (−1, 1). In FIG. 8D, ($c_1$, $c_2$, $c_3$, $c_4$)=(1.01, 1, 1, 1.11). Under a rotating gradient magnetic field, the microagent converges to (0, −1). These figures show that the microagent moves to different aggregation centers when changing the parameter c. That is, the location of the aggregation center can be adjusted by adjusting the current parameter c.

In accordance with some embodiments, the following rules apply when adjusting $c_i$ to determine the position of an aggregation center. First, $c_i$ for the magnetic coils on the same axis cannot be adjusted simultaneously. That is, taking the magnetic sources with four coils as an example, when adjusting $c_1$ for the first coil, the $c_3$ for the third coil in the opposite direction should keep the base value of 1. This should be applied to $c_2$ and $c_4$ similarly. Second, the current change is always conducted incrementally, which means that $c_i$ is no less than 1 when $c_i$ starts to change from a base value of 1. Coil pairs that change the coil current have four types, which are coils 1-2, 2-3, 3-4, and 4-1. Considering c=($c_1$, $c_2$, $c_3$, $c_4$) as the parameter group for four coils. When c=(1, 1, 1, 1), the aggregation center is located at the physical center of the workspace, namely, (x, y)=(0, 0). By changing $c_i$, the position of the new aggregation center can be calculated on the basis of Equation (5) as set forth below. Then, the reverse mapping relationship from g(x, y) to c can be established using a back propagation neural network (BPNN) model. Here, the BPNN model contains three layers, namely, an input layer g(x, y), an output layer c, and a hidden layer. By way of example, the number of hidden layer units is 10. The rectified linear unit and mean squared error functions are used as the activation function and loss function, respectively. When $c_i$ is increased from 1 to 2 at a step of 0.01, 100×100 data will be used to train the BPNN model with Python, and the reduced state sequence estimation (RSSE) method will be used as the evaluation function. When the RSSE is less than 0.001 after 10,000 iterations, convergence is reached, and then the training model is established. In this way, the position of any desired aggregation center can be determined by setting the corresponding c. As an example, FIG. 9 shows a mapping relationship between the aggregation center position g(x, y) and c when the workspace of 15 mm×15 mm is divided into 15×15 unit square areas. The unit square area with a length of 1 mm is accurate enough for most clinical treatments (e.g., tumor therapy).

The model of an individual microagent driven by a rotating gradient magnetic field in low-Reynolds (Re) number regimes was established as follows. Let $\mu_0 = 4\pi \times 10^{-7}$ Tm/A denote the permeability of a free space, $m_0$ denote the point dipole moment, E denote the identity matrix, r denote the position of a microagent in the field, and p denote the magnetized vector of point dipole starting from the center of a workspace to the point dipole of coil. Under unit electric current, the magnetic field unit flux density $B_{unit}(r')$ of a single magnetic coil can be described as:

$$B_{unit}(r') = \frac{\mu_0}{4\pi}\left(\frac{3(m_0 \cdot r')r'}{\|r'\|^5} - \frac{m_0}{\|r'\|^3}\right) \quad (2)$$

where r'=−r+p, representing the vector connecting the position of the microagent and the point dipole of the coil. Define a horizontal plane that includes the point dipole of coil as reference plane (or zero-plane) and a plane higher than the reference plane by a distance of h as h-plane. For a single magnetic coil, the flux density $B_{unit}(r, 0)$ in the h-plane (where h=0) can be simplified as $B_{unit}(r, 0) = \mu_0 m_0/(2\pi\|-r+p\|^3)$. Then, the unit flux density $B_{unit}(r, h)$ in the h-plane can be derived by extending as follows:

$$B_{unit}(r, h) = \frac{\mu_0 m_0}{2\pi\left(\|-r+p\|^2 + h^2\right)^{3/2}} \quad (3)$$

When applying the sequentially DC input $I_i$ described in equation (1) and FIG. 7, the flux density B(r, h) of the rotating gradient magnetic field is expressed by $$B(r, h) = \sum_{i=1}^{n} B_i(r, h) = \sum_{i=1}^{n} B_{unit}(r, h) I_i R_i \quad (4)$$
$$= \sum_{i=1}^{n}\left(\frac{\mu_0 m_0}{2\pi\left(\|-r+p\|^2 + h^2\right)^{3/2}}\right) I_i R_i$$

where $B_i(r, h)$ is the flux density generated by the ith magnetic coil, $I_i$ is the current input of the ith coil, n is the number of coils, and $R_i$ is an orientation matrix of the ith coil expressed as $$R_1 = \begin{bmatrix} 1 & 0 \\ 0 & 1 \end{bmatrix}, R_2 = \begin{bmatrix} 0 & -1 \\ 1 & 0 \end{bmatrix}, R_3 = \begin{bmatrix} -1 & 0 \\ 0 & -1 \end{bmatrix}, R_4 = \begin{bmatrix} 0 & 1 \\ -1 & 0 \end{bmatrix} \text{ when } n = 4.$$

Using Equation (4), the magnetic driving force $F_{mag}$ can be estimated as $$F_{mag} = (m \cdot \nabla) B(r, h) \tag{5}$$

where $m = VTx/\mu_0(1+x)$, representing the magnetic moment of the microagent, and $\nabla$ denotes the Hamiltonian operator representing the gradient of field. Given that the microagent always moves in a quasi-equilibrium state in a low Re number regime, the resistance force of the liquid, denoted by drag force $F_{drag}$, is equal to $F_{mag}$, namely, $F_{mag} = F_{drag}$. The drag force is calculated as $F_{drag} = 6\pi\eta R v$, where R is the equivalent radius of the microagent, $\eta$ is the dynamic viscosity of the fluid, and v is the velocity of the microagent.

Then, the position of the microagent at time t, denoted by r(t), can be derived as:

$$r(t) = \int_0^t v dt = \int_0^t \frac{F_{drag}}{6\pi\eta R} \cdot dt = \int_0^t \frac{1}{6\pi\eta R} \cdot (m \cdot \nabla) B(r, h) dt \tag{6}$$

As time $t \to \infty$, $r(\infty)$ represents an equilibrium position to which the microagent converges, which is defined as the aggregation center, denoted by g(x, y), where x and y are coordinates in the working plane. The point dipole moment $m_0$ and the magnetic moment m can be solved by Genetic Algorithm (Python, scikit-opt solver). As a function of r(t), p can be solved. Using r(t) in Equation (6), the velocity v of the microagent can be estimated; therefore, the drag force $F_{drag}$ can be determined. Consequently, the magnetic force $F_{mag}$, which is equal to $F_{drag}$, can be estimated.

Figure 10:
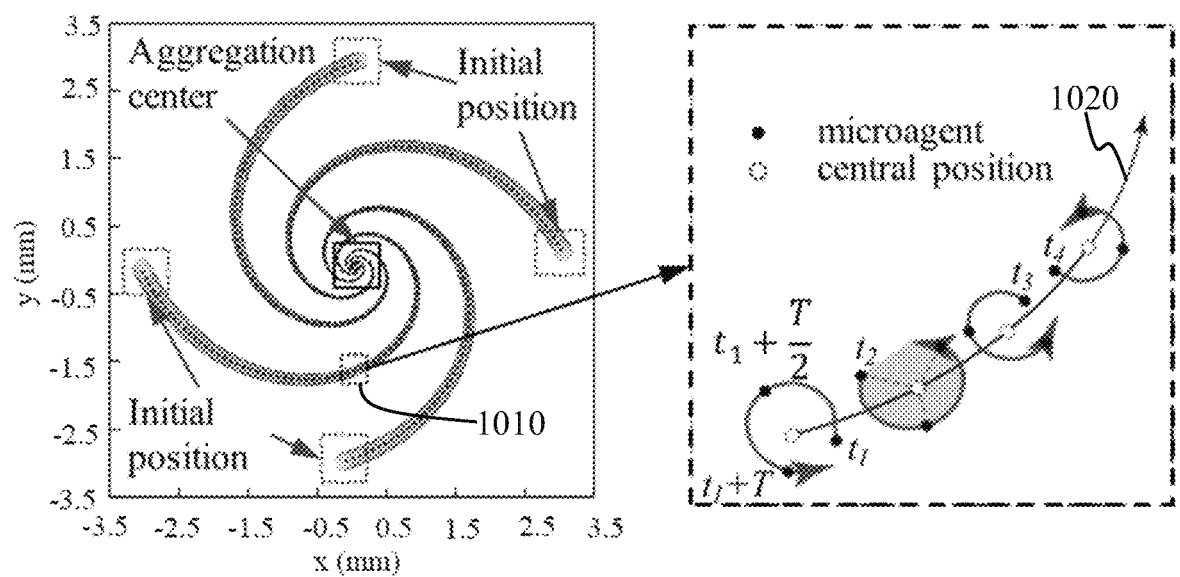
FIG. 10 illustrates simulation results of a converging trajectory in accordance with certain embodiments.
Figure 11:
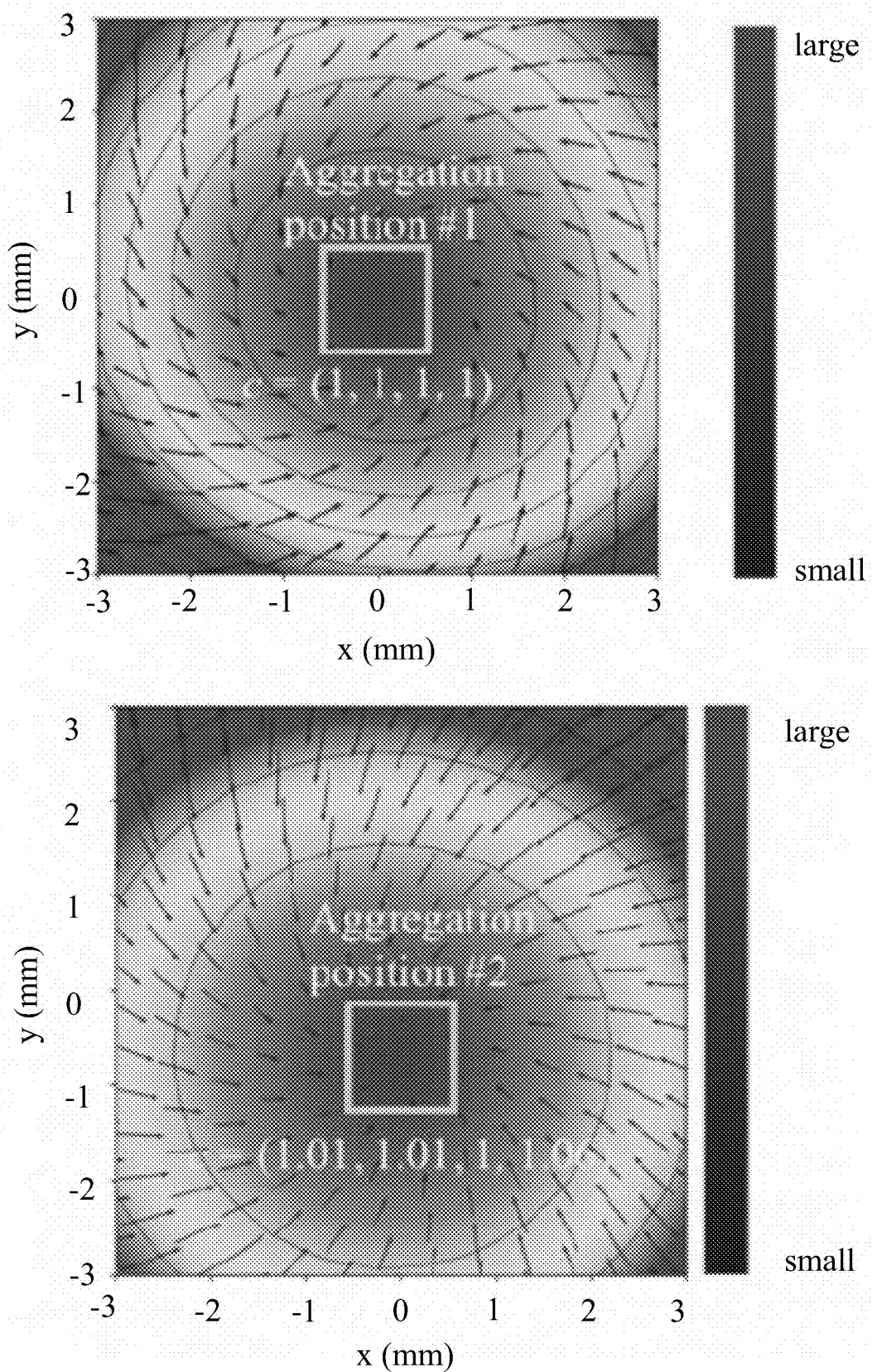
FIG. 11 illustrates force field distributions with two different aggregation centers in according with certain embodiments.
Figure 12A:
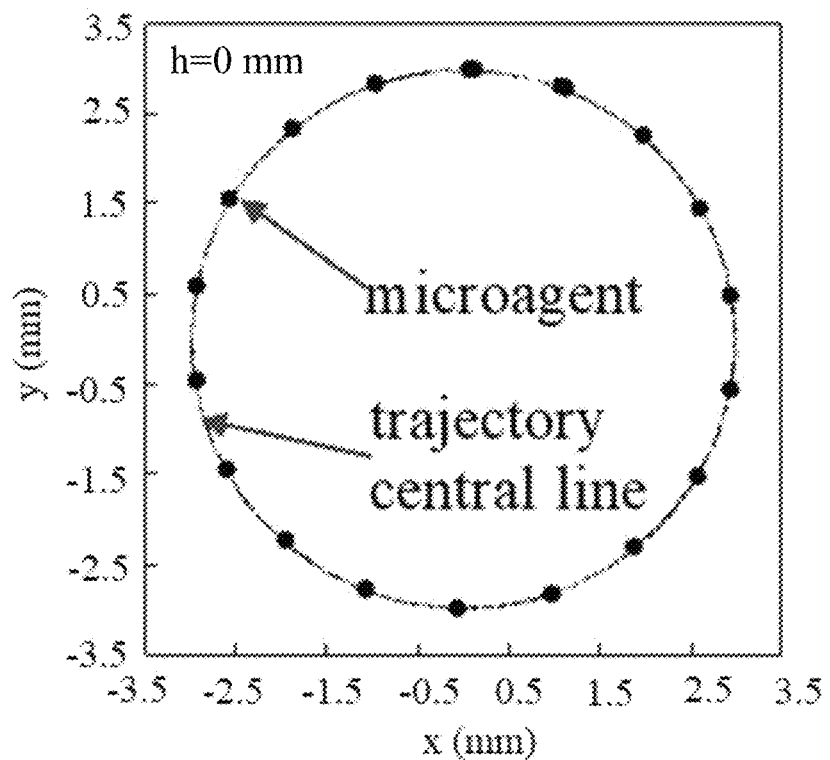
FIG. 12A shows simulation results of motion trajectory of a microagent in a working plane with h=0 in accordance with certain embodiments.
Figure 12B:
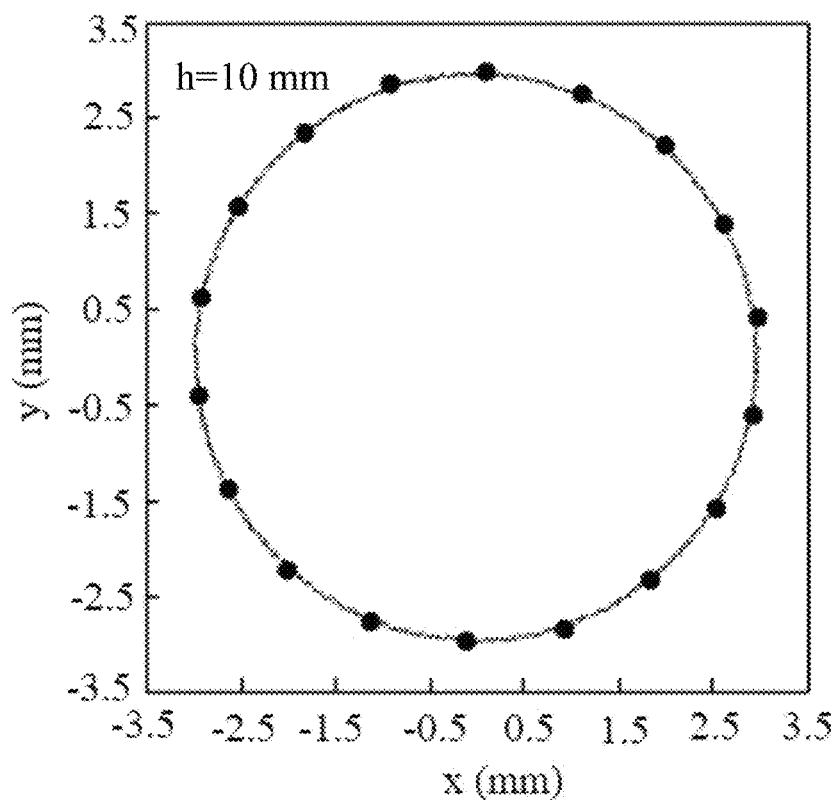
FIG. 12B shows simulation results of motion trajectory of a microagent in a working plane with h=10 in accordance with certain embodiments.
Figure 12C:
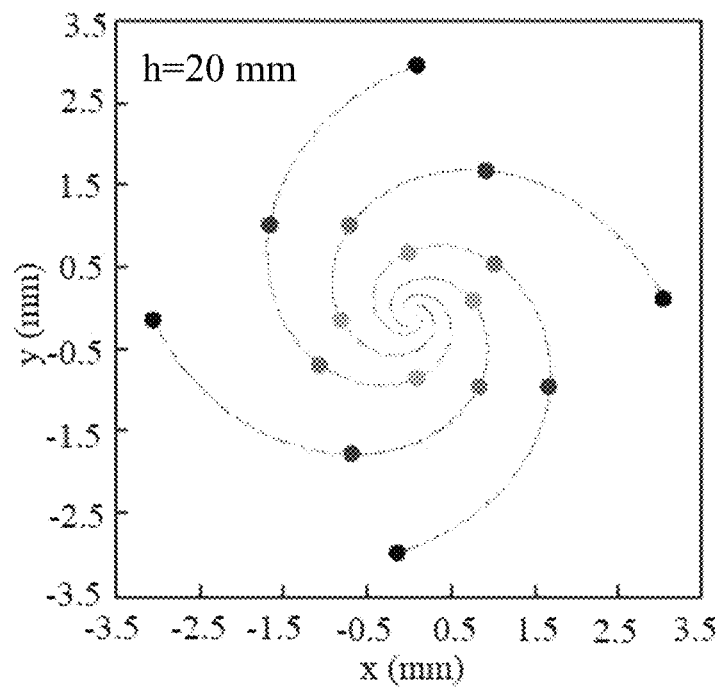
FIG. 12C shows simulation results of motion trajectory of a microagent in a working plane with h=20 in accordance with certain embodiments.
Figure 12D:
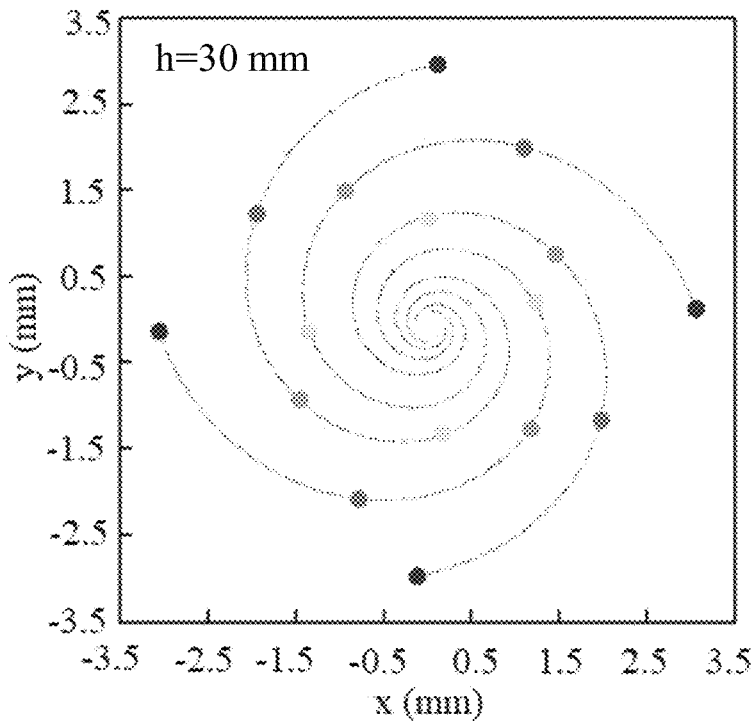
FIG. 12D shows simulation results of motion trajectory of a microagent in a working plane with h=30 in accordance with certain embodiments.

FIG. 10 illustrates simulation results of a converging trajectory r(t) in accordance with certain embodiments. FIG. 11 illustrates force field distributions (magnetic force $F_{mag}$) with two different aggregation centers in according with certain embodiments. By way of example, for FIG. 10 and the Aggregation position #1 of FIG. 11, frequency f=20 Hz, current I=2 A and $c_1=c_2=c_3=c_4=1$. As illustrated in FIG. 10, the microagent is initially located at four initial positions respectively, which are (0, 3), (3, 0), (0, −3), (−3, 0). Then the individual microagent converges to the center of the workspace, i.e. the aggregation center. The trajectory of the microagent is expressed with dotted lines.

The right of FIG. 10 is an enlarged view of a trajectory portion 1010. As can be seen, the microagent rotates around a centerline or central line 1020 and moves forward along the arrow of the centerline 1020, where T represents time period, and $t_1$, $t_2$, $t_3$, $t_4$ represent different time points. Given that actual motion of the microagent is an orbital revolution around the centerline 1020, it can be treated as a movement along the centerline 1020. It can be seen that the microagent converges to the aggregation center from four different positions successfully, showing that the rotating magnetic field can produce a centripetal force to attract the microagent to converge to a target position or site.

FIG. 11 displays field distributions of the estimated magnetic force $F_{mag}$, which are calculated on the basis of Equation (6). The arrows represent directions of the magnetic force, and the contour maps and distribution represent the value of the estimated magnetic force.

FIGS. 12A-12D shows simulation results of motion trajectory of a microagent in the working planes with different h=0, 10, 20, and 30 mm respectively in accordance with certain embodiments. The solid dots represent microagents, and the dot lines represent trajectories. The calculation result shows that the flux density B(r, h) of the rotating gradient magnetic field is closely related to the height h of the working plane. In the planes of h=0 mm (FIG. 12A) and h=10 mm (FIG. 12B), the microagent moves near the boundary of the workspace, and the aggregation effect is not so obvious. In the planes of h=20 mm (FIG. 12C) and h=30 mm (FIG. 12D), the microagent moves towards a central position or an aggregation center, indicating that the microagent can be attracted by the rotating magnetic field in these two planes.

Figure 13:
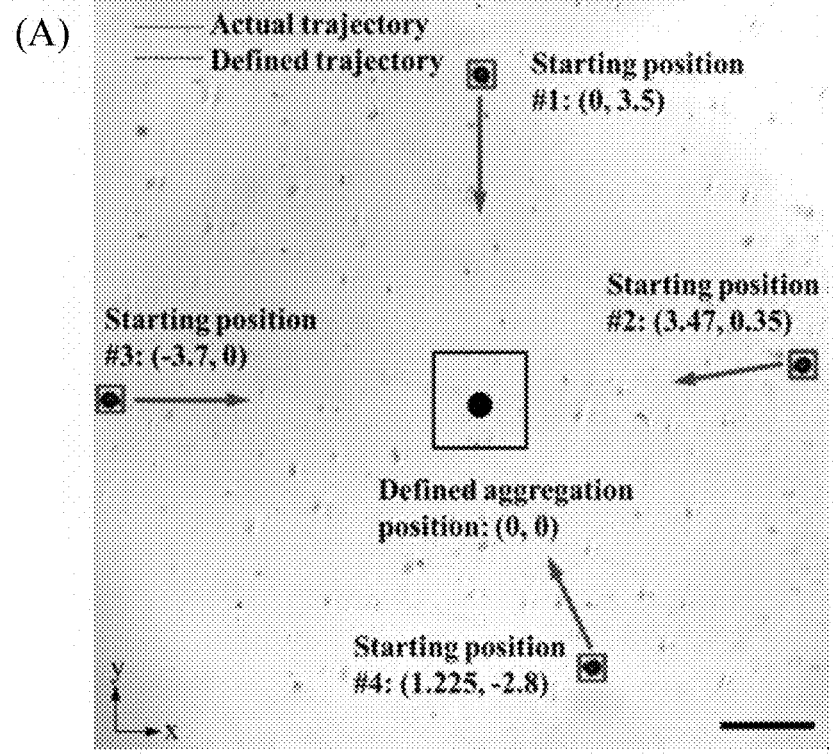
FIG. 13 illustrates experimental results of a single microagent convergence in accordance with certain embodiments where (A) shows moving trajectories of single microagents (Fe, 300 μm) from four different starting positions in 1,000 pcs dimethylsiloxane (I=2.5 A, f=20 Hz, $c_i$=1); (B) shows moving trajectories of single microagents in 1,000 pcs dimethylsiloxane when the aggregation position is changed by adjusting current parameter $c_i$ for the rotating gradient magnetic field.
Figure 13:
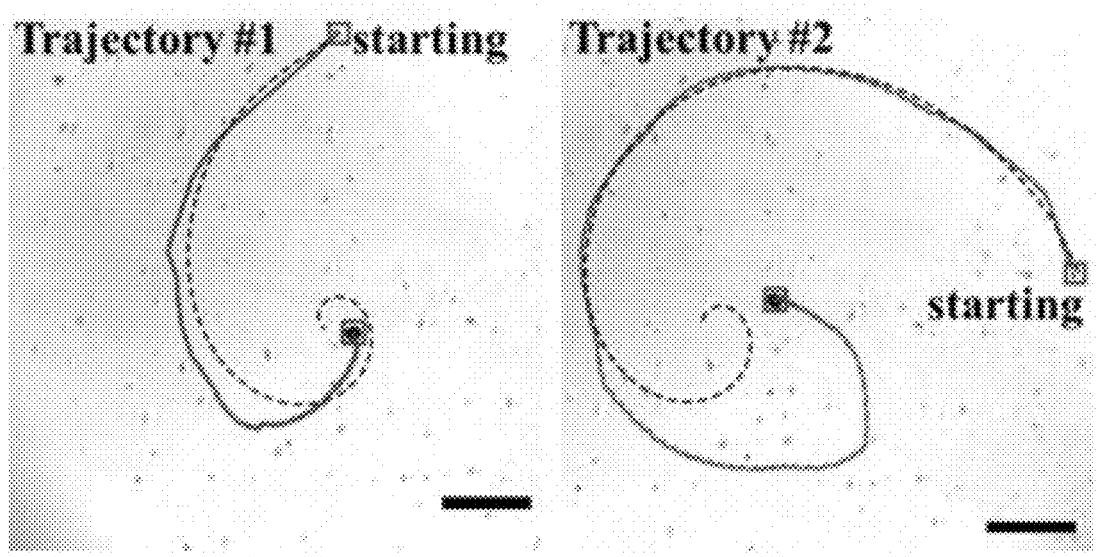
Figure 13:
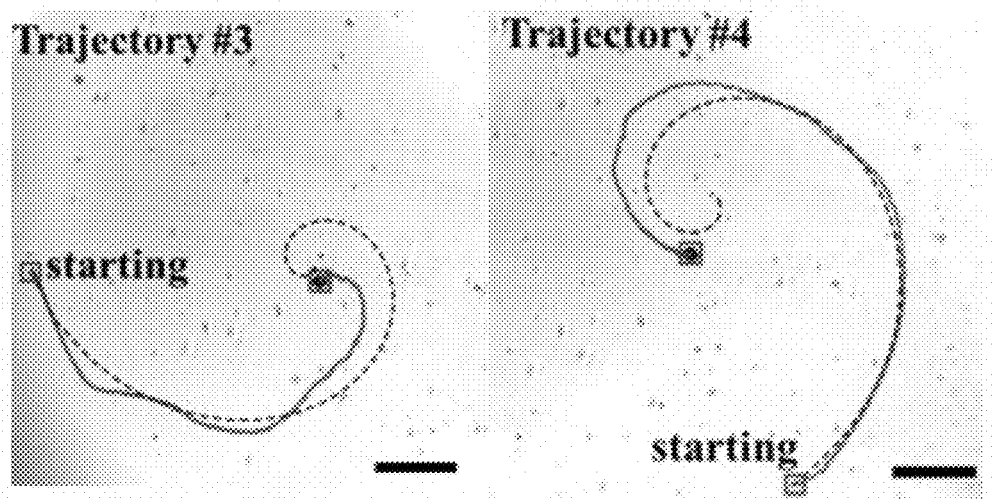
Figure 13:
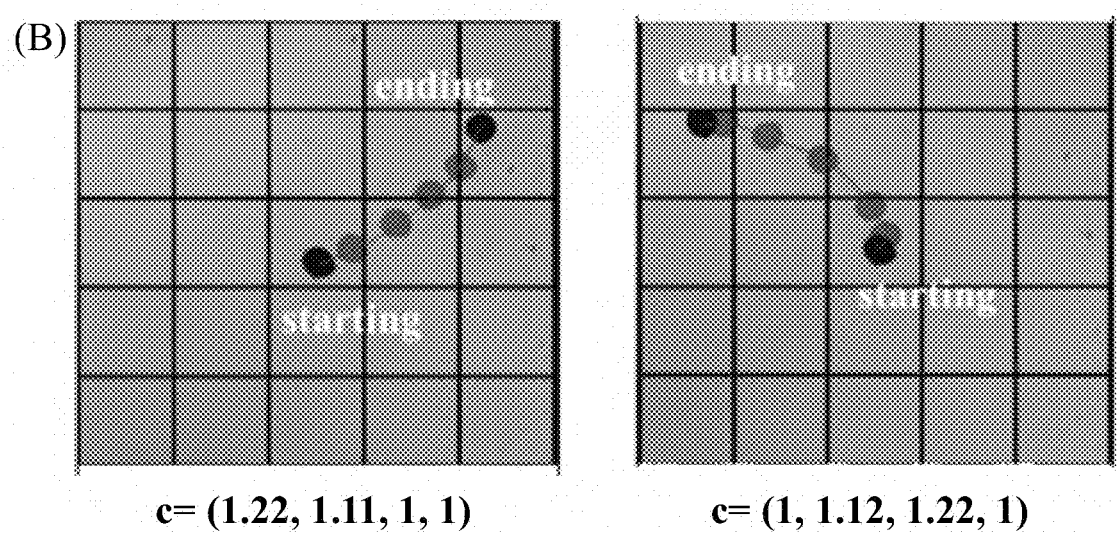
Figure 13:
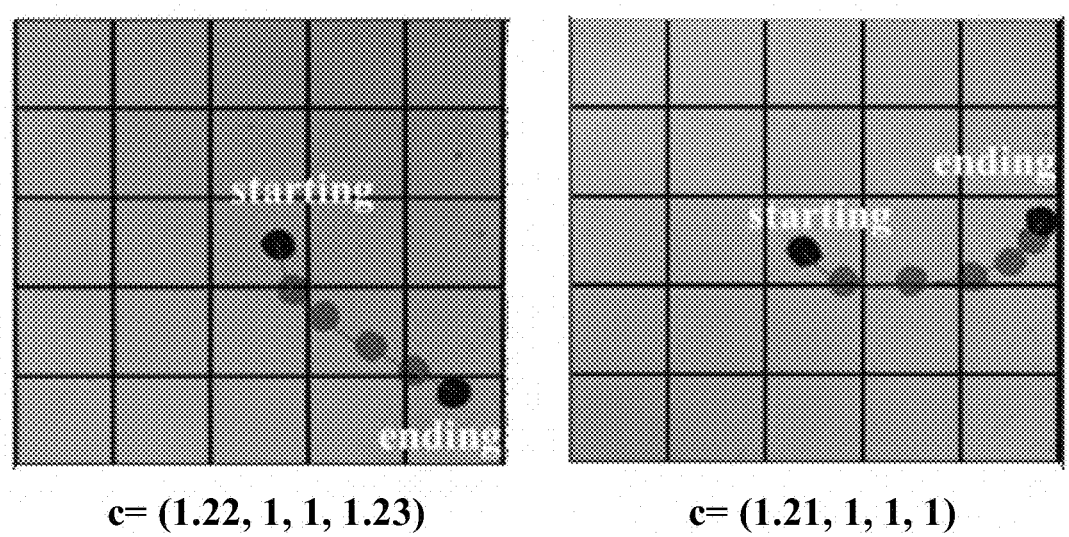

FIG. 13 illustrates experimental results of a single microagent convergence. FIG. 13(A) shows moving trajectories of single microagents (Fe, 300 µm) from four different starting positions in 1,000 pcs dimethylsiloxane (I=2.5 A, f=20 Hz, $c_i$=1). Scale bar=1 mm. Each starting point corresponds to a respective trajectory group, and therefore there are four trajectory groups #1, #2, #3, and #4. For each trajectory group, a dot line represents a defined trajectory while a solid line represents an actual trajectory. FIG. 13(B) shows moving trajectories of single microagents in 1,000 pcs dimethylsiloxane when the aggregation position is changed by adjusting current parameter $c_i$ for the rotating gradient magnetic field. As can be seen, when the current parameter $c_i$ changes, the trajectory changes and accordingly a different aggregation center is reached.

Figure 14A:
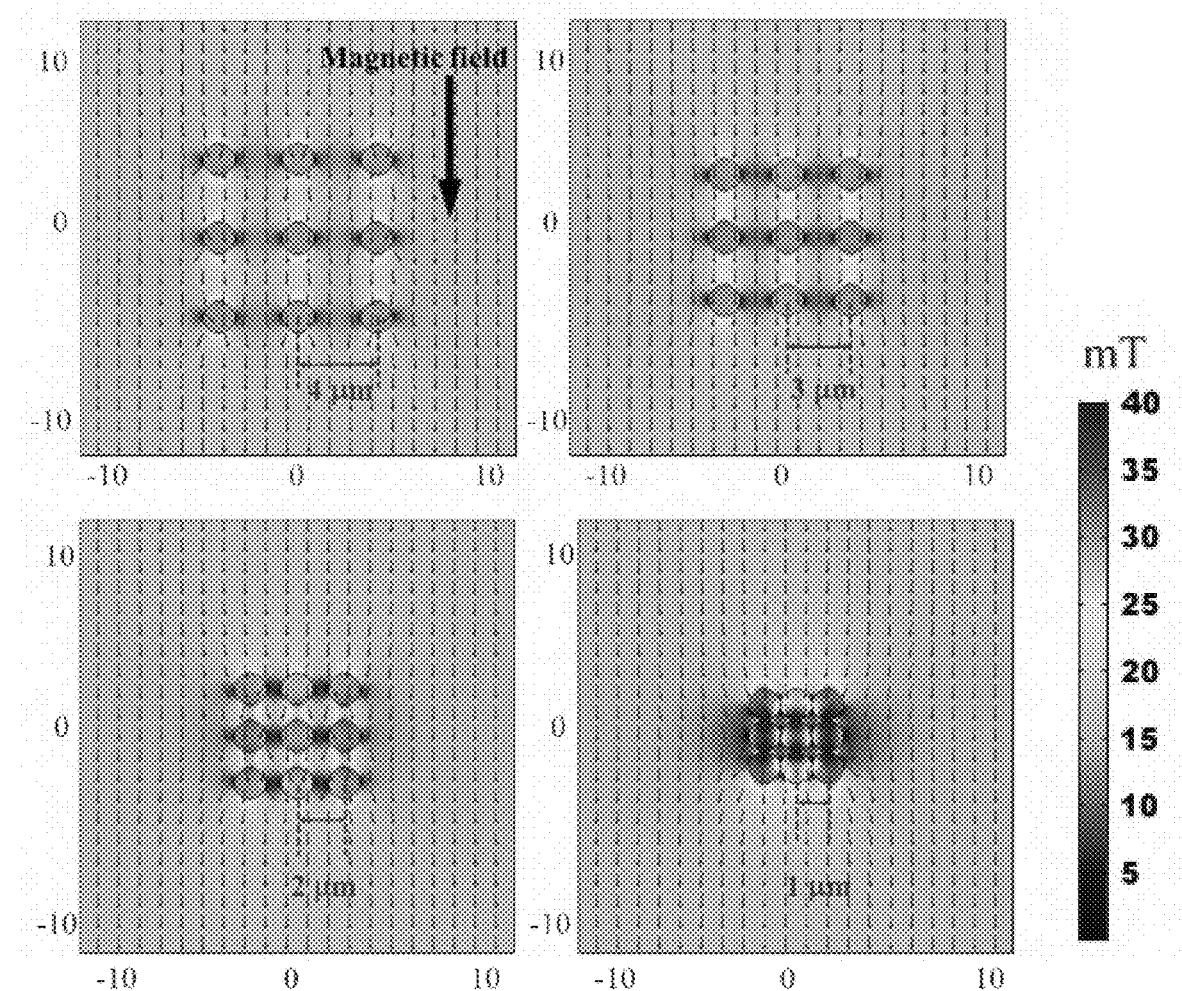
FIG. 14A shows simulation results of agent-agent interaction in a magnetic field with a vertically downward direction in accordance with certain embodiments.
Figure 14B:
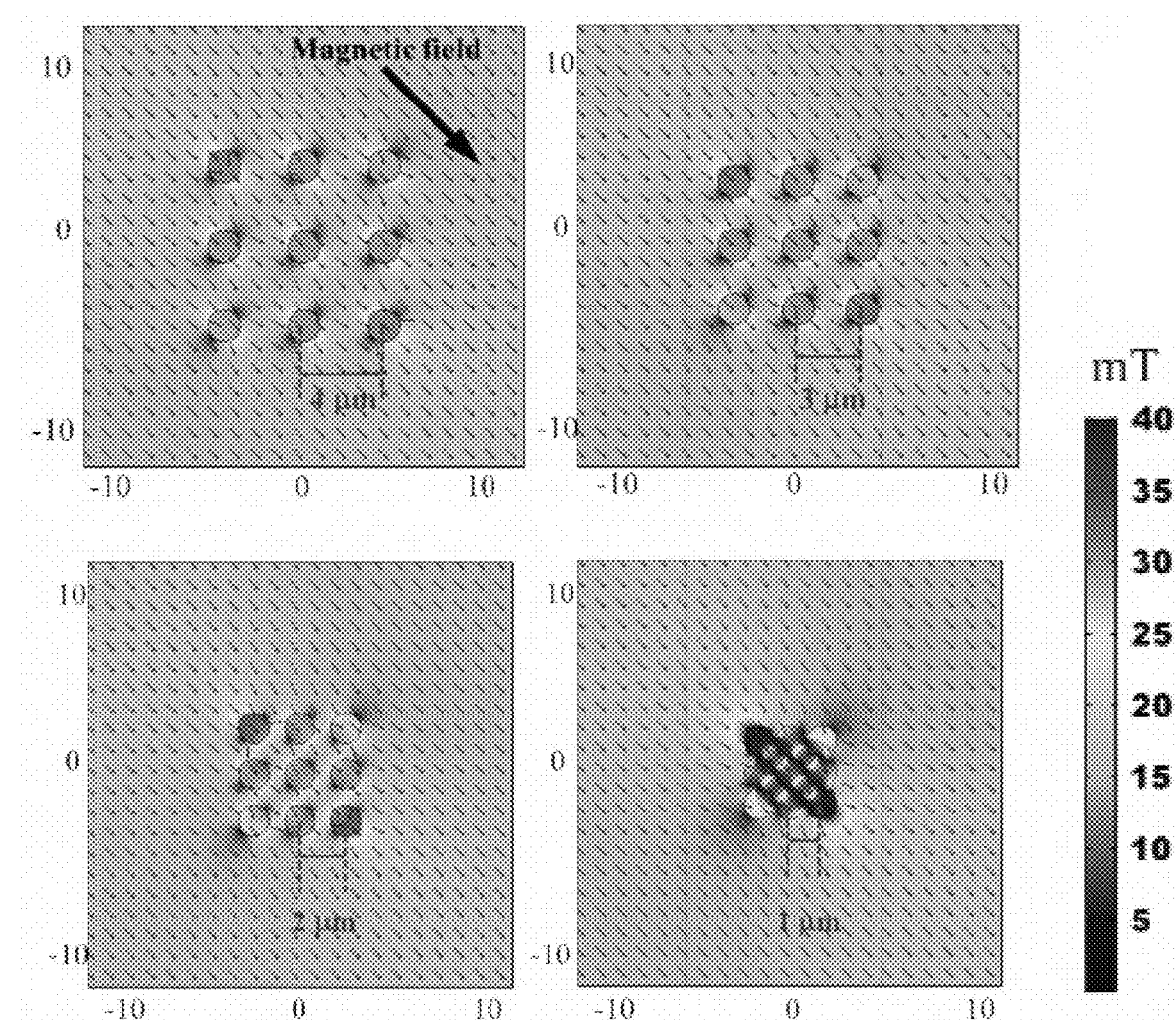
FIG. 14B shows simulation results of agent-agent interaction in a magnetic field with a sloped downward direction in accordance with certain embodiments.

FIGS. 14A and 14B show simulation results of agent-agent interaction in a magnetic field in accordance with certain embodiments. By way of example and for the simulation, spherical-shaped hematite microparticles (diameter: 1 µm) are used. The simulation is performed using an AC/DC Module of COMSOL Multiphysics. FIG. 14A illustrates magnetic field distributions of microparticle arrays with different distances. The distance between neighboring array centers decreases from 4 µm to 1 µm. Direction of the magnetic field is vertically downward. For FIG. 14B, the difference from FIG. 14A is that the direction of the magnetic field slopes downward. As can be seen, when the distance between microparticles is small enough (e.g., <1 µm), the magnetic field will affect the agent-agent interaction.

Figure 15A:
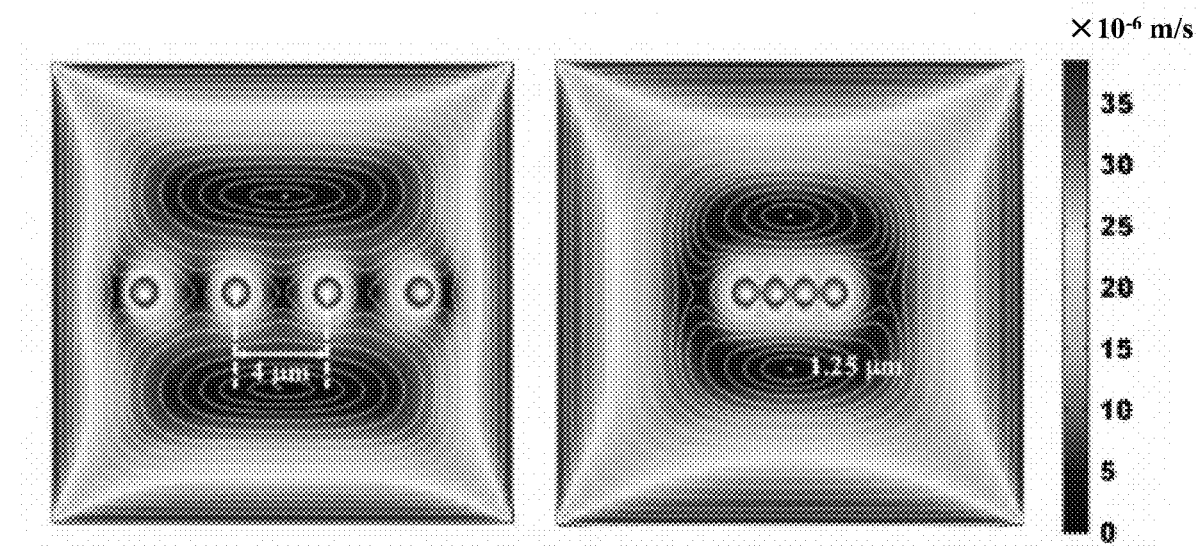
FIG. 15A shows simulation results of agent-agent interaction in a fluid where microparticles are fixed at their positions in the fluid in accordance with certain embodiments.
Figure 15B:
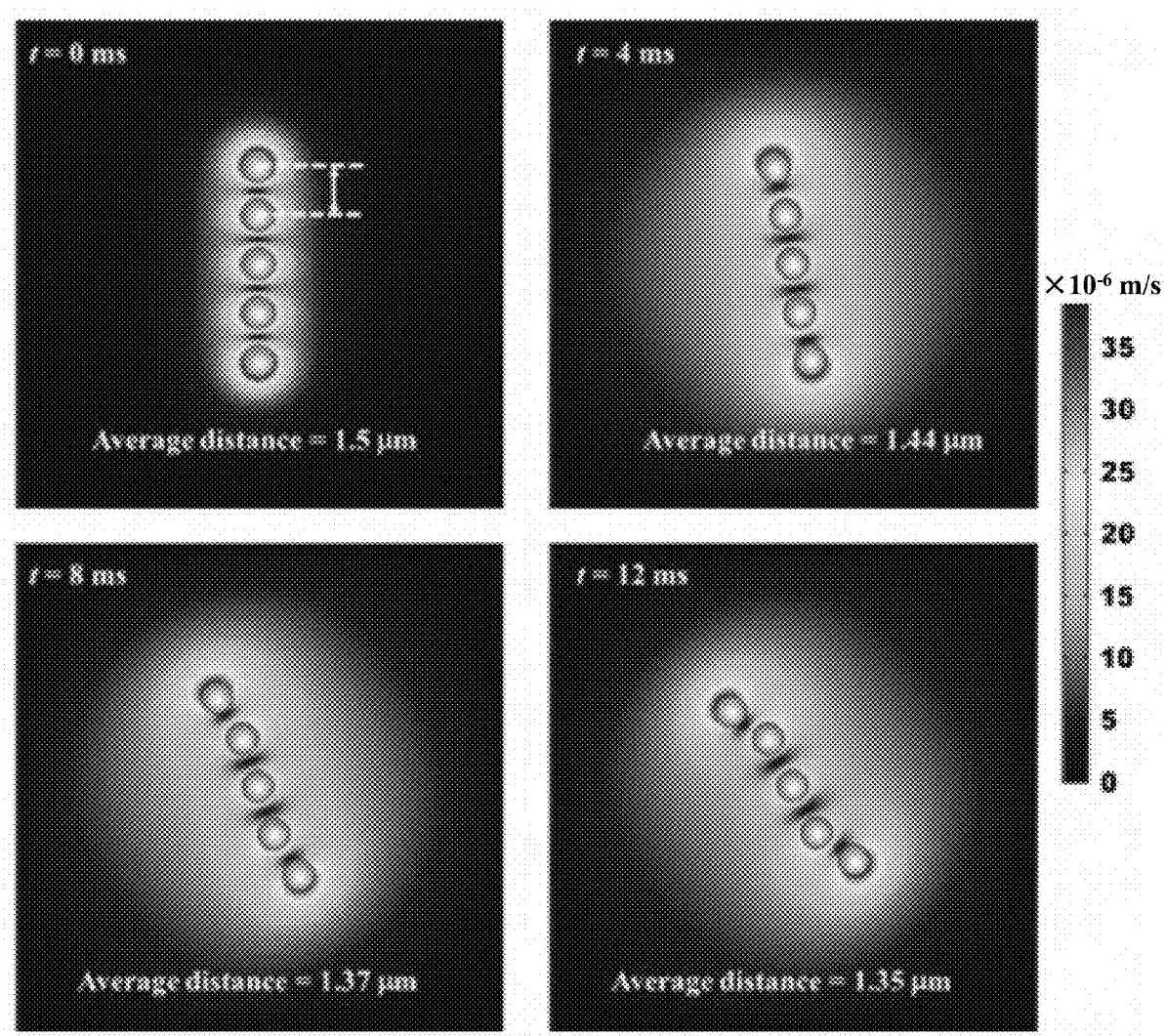
FIG. 15B shows simulation results of agent-agent interaction in a fluid where microparticles are freely released in the fluid in accordance with certain embodiments.

FIG. 15A and 15B show simulation results of agent-agent interaction in a fluid in accordance with certain embodiments. By way of example and for the simulation, spherical-shaped hematite microparticles (diameter: 1 µm) are used. FIG. 15A illustrates flow field distribution when the microparticles are fixed at their positions in the fluid. The simulation is performed using the Rotating Machinery Module of COMSOL Multiphysics. Each microparticle is assumed to rotate at a frequency of 10 Hz. When the distance between two adjacent microparticles is 4 µm, the fluid fields of the microparticles do not affect the interaction among microparticles. When the distance is reduced to 1.25 µm, the fluid fields of adjacent microparticles are merged, indicating that the particle-particle interaction are affected by the fluid. FIG. 15B illustrates flow field distribution when five microparticles are freely released in fluid. The simulation is performed using the Fluid-Structure Interaction of COMSOL Multiphysics. Each microparticle is assumed to rotate at a frequency is 10 Hz. When t=0 s, the distance between two adjacent microparticles is 1.5 µm. After 12 ms, the microparticles form a chain-like structure, and the distance is reduced to 1.35 µm, indicating that the fluid affects the behavior of microparticles.

Figure 16:
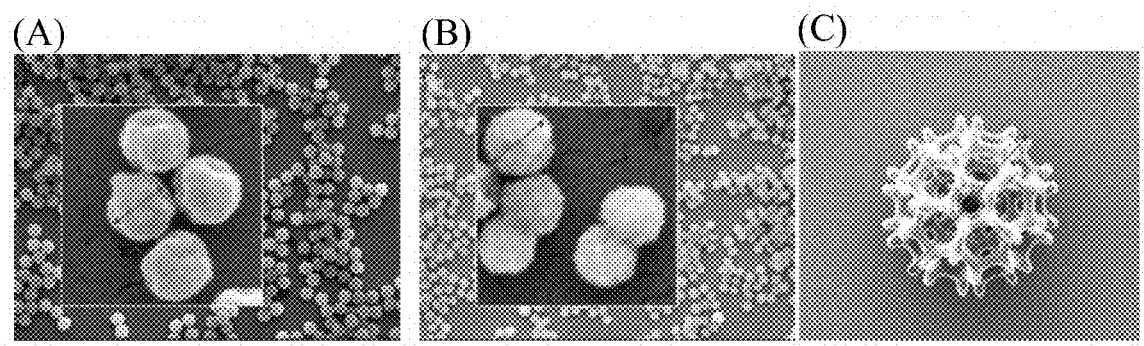
FIG. 16 shows images of different microagents (A) spherical-shaped hematite microparticles; (B) superparamagnetic iron oxide microparticles; and (C) burr-like porous spherical structure in accordance with certain embodiments.

FIG. 16 shows images of different microagents in accordance with certain embodiments. The morphology of the microparticles and fabricated microrobots is observed under a scanning electron microscope (SEM). (A) shows spherical-shaped hematite microparticles with superparamagnetic core and polymer outsourcing layer with a diameter of 1 μm. (B) shows superparamagnetic iron oxide microparticles with superparamagnetic core. (C) shows a burr-like porous spherical structure and a diameter of 80 μm, manufactured by a two-photon lithography system using degradable materials doped with 2% superparamagnetic materials.

FIGS. 17A-17D illustrate an aggregation process of a microparticle swarm in accordance with certain embodiments. The magnetic microagents used in these experiments include microparticles (diameter: 1 μm) and spherical microrobots (diameter: 80 μm). The frequency of the rotating magnetic field is 10 Hz, and the current I from the power source is 2.5 A.

Figure 17A:
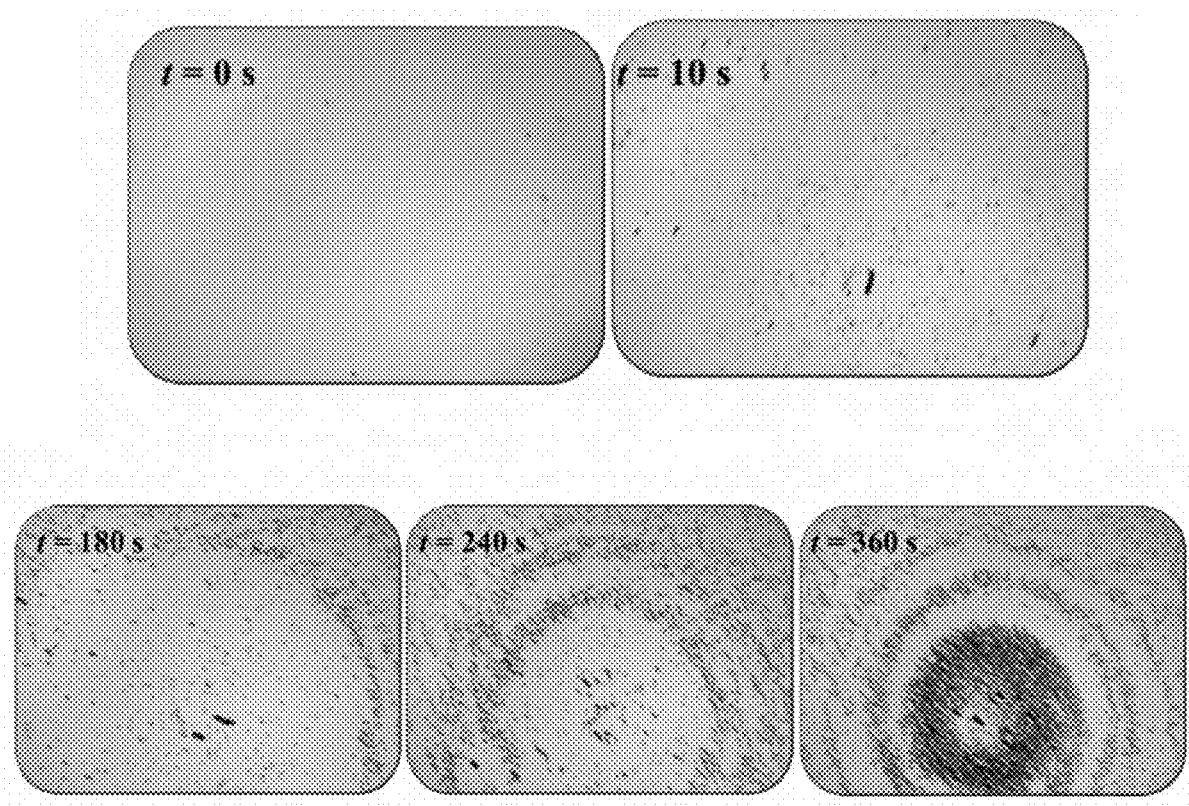
FIG. 17A illustrates an aggregation process of a microparticle swarm where microparticles are distributed in a chamber with low density in accordance with certain embodiments.
Figure 17B:
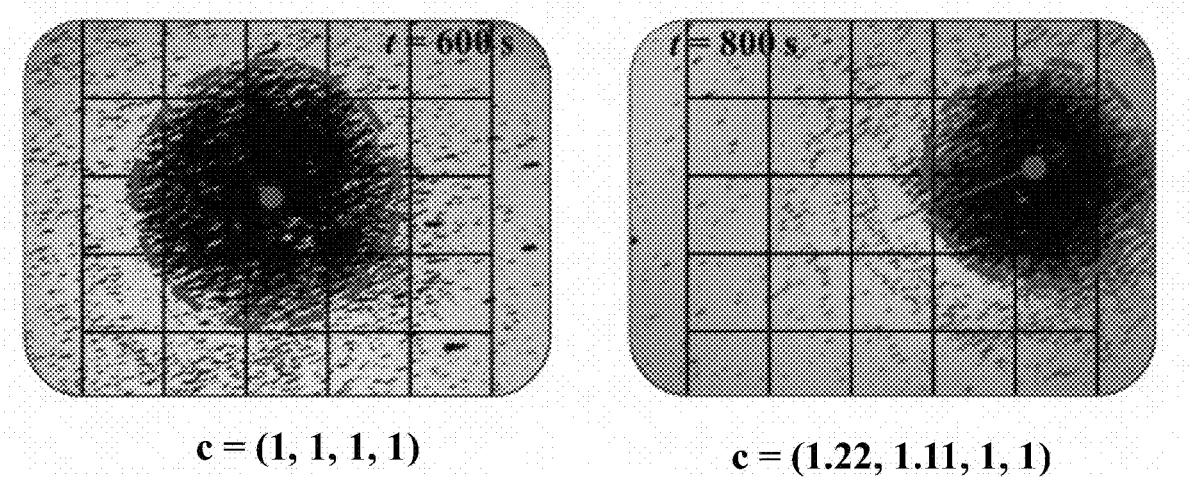
FIG. 17B illustrates gathering of microparticles at different aggregation areas under different parameters $c=(c_1, c_2, c_3, c_4)$ in accordance with certain embodiments.
Figure 17B:
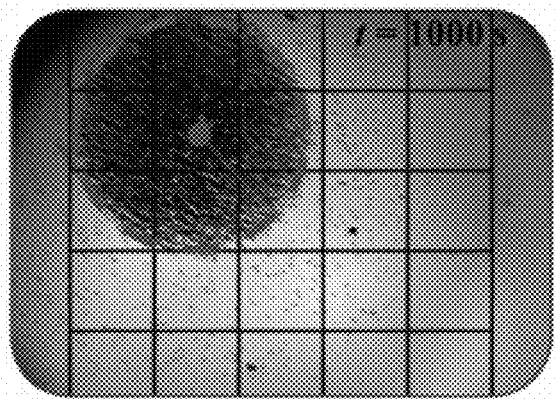
Figure 17B:
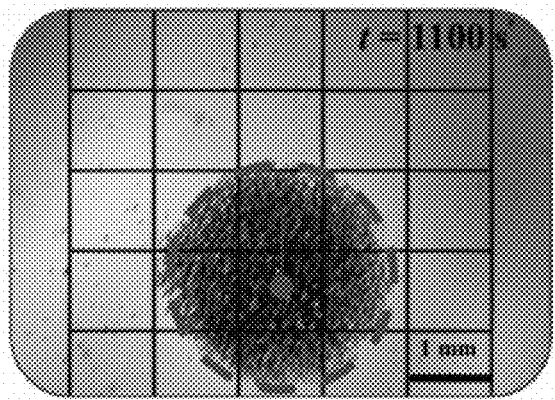

In FIG. 17A, the microparticles are distributed in a chamber with low density. At the beginning, the microparticles are distributed in a custom-made chamber with a density as low as 1 μg/ml. When a magnetic field is applied, the microparticles converge to a resulting aggregation center or are confined in an aggregation area. It can be seen that as time increases, more and more microparticles gather and are densely distributed around the aggregation center or in the aggregation area. FIG. 17B illustrates that by changing current parameter $c=(c_1, c_2, c_3, c_4)$, the microparticles gather at different aggregation areas. From left to right, the parameters c are (1, 1, 1, 1), (1.22, 1.11, 1, 1), (1, 1.12, 1.11, 1) and (1.01, 1, 1, 1.11) respectively. A dotted circle represents boundary of the circle that covers 95% of the microparticles.

Figure 17C:
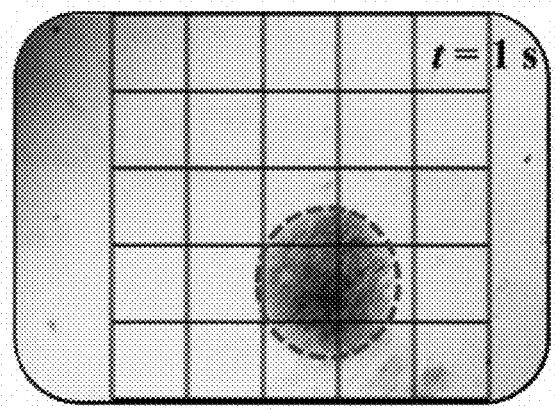
FIG. 17C illustrates locomotion of a swarm of microparticles (diameter: 1 μm) by changing parameters $c=(c_1, c_2, c_3, c_4)$ in accordance with certain embodiments.
Figure 17C:
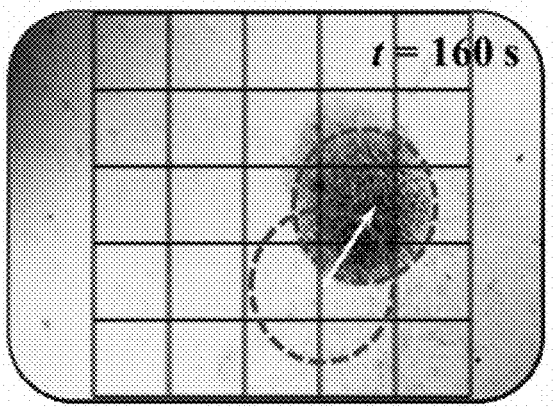
Figure 17C:
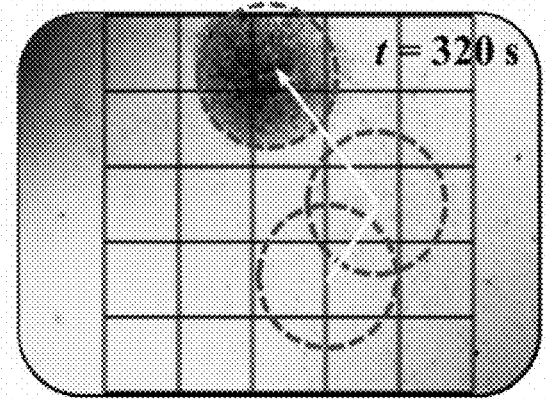
Figure 17C:
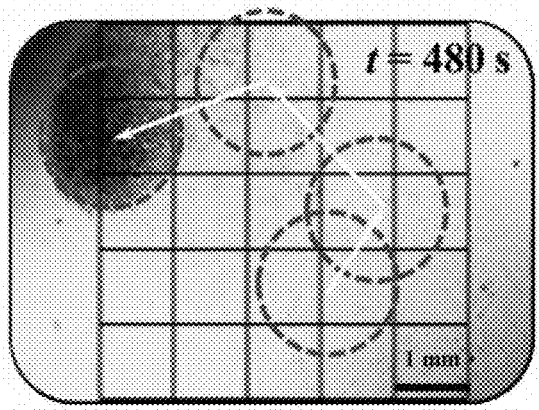

FIG. 17C illustrates locomotion of a swarm of microparticles (diameter: 1 μm). The swarm of microparticles is substantially confined in an aggregation area with a boundary denoted by a dot circle. At 1 s, the microparticle swarm is located at its original position by setting c=(1.11, 1, 1, 1.12). After changing c to (1.10, 1.02, 1, 1), the microparticle swarm moves to a new aggregation area at 160 s. By adjusting c to (1, 1.23, 1.01, 1), the microparticle swarm continues to move to a new aggregation area at 320 s. By adjusting c to (1, 1.12, 1.22, 1), the microparticle swarm then moves to a new aggregation area at 480 s. That is, with adjustment of the parameter c, the location or position of the aggregation area can be adjusted.

Figure 17D:
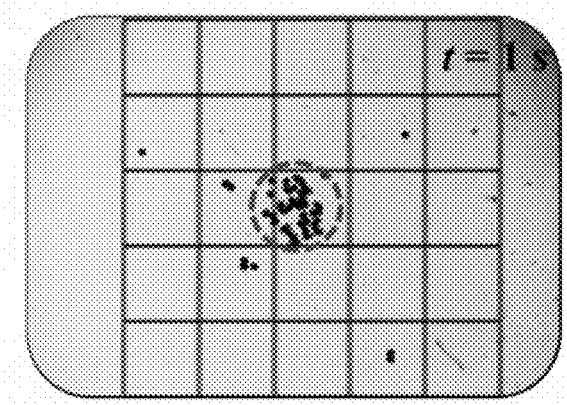
FIG. 17D illustrates locomotion of a group of 30 microrobots (diameter: 80 μm) by changing parameters $c=(c_1, c_2, c_3, c_4)$ in accordance with certain embodiments.
Figure 17D:
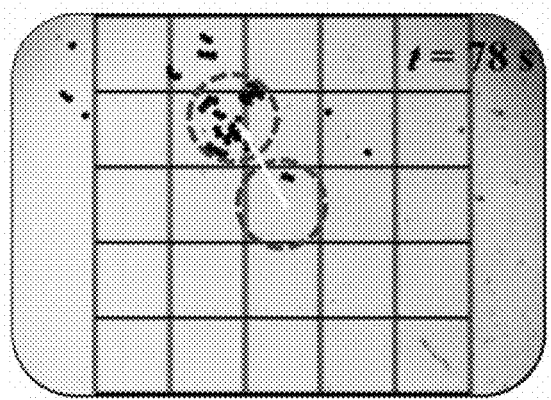
Figure 17D:
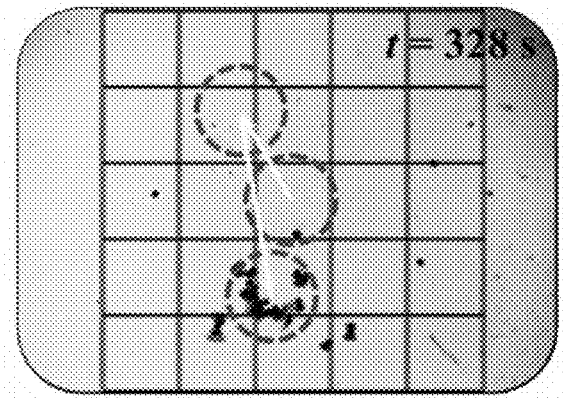
Figure 17D:
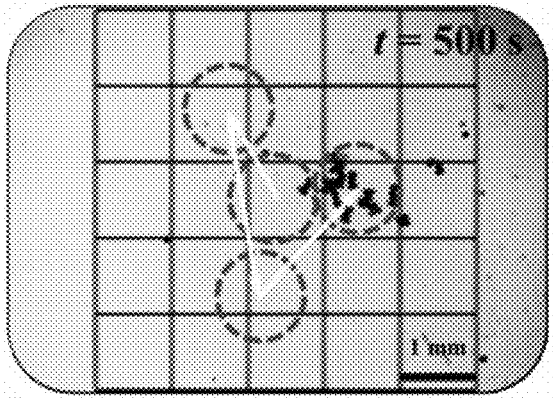

FIG. 17D illustrates locomotion of a group of 30 microrobots (diameter: 80 μm). By adjusting the parameter c, as can be seen, the microrobot swarm will migrate to a new aggregation area.

These results verify that a rotating gradient magnetic field, when properly designed, can accumulate different types of magnetic microagents, despite their size, shape, or material characteristics. Also, the driving mechanism does not depend on agent-agent interaction among microagents.

Figure 18A:
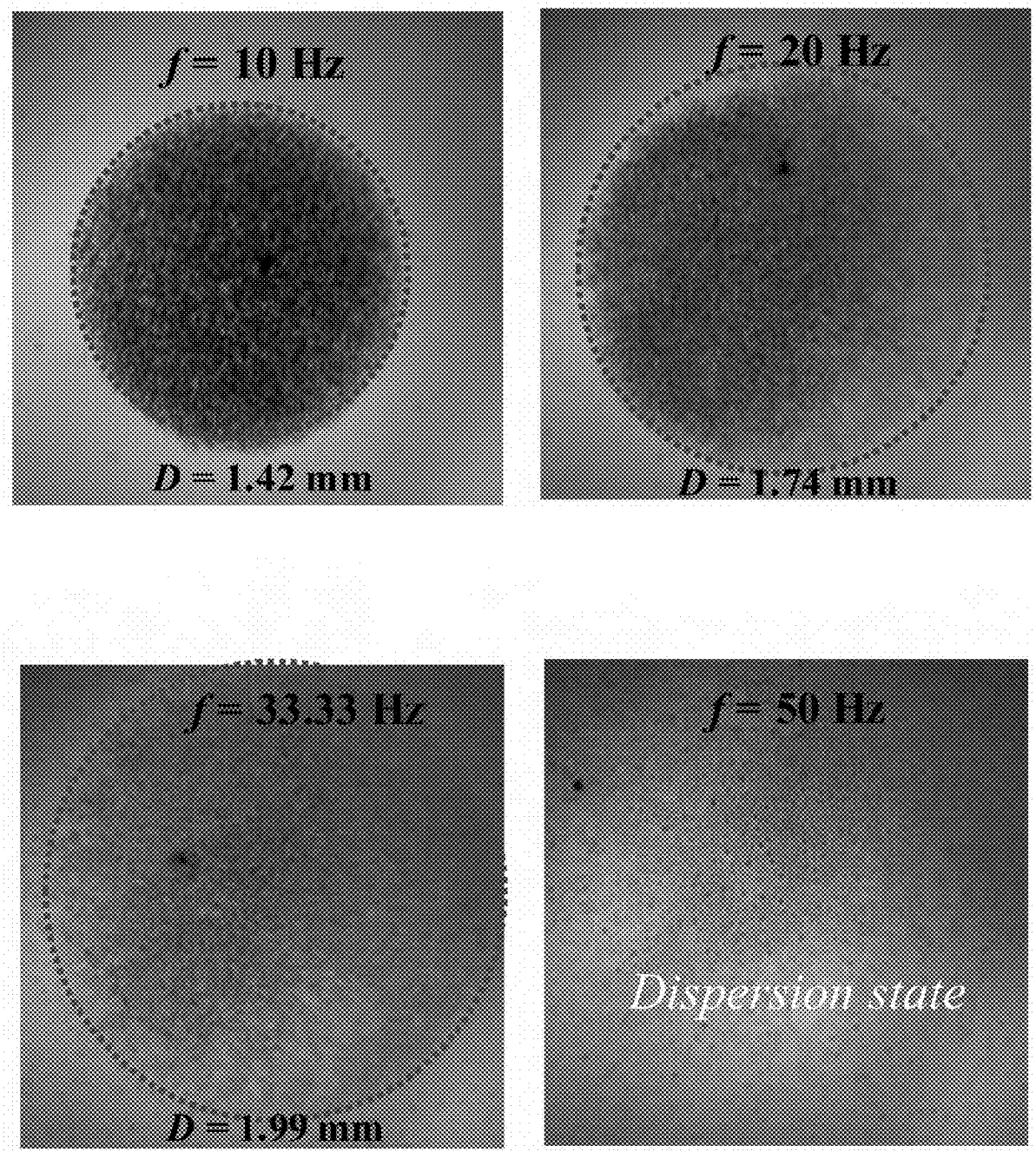
FIG. 18A illustrates a microparticle swarm on a working plane with h=20 mm, but at frequencies ranging from 6.66 Hz to 50 Hz in accordance with certain embodiments.
Figure 18B:
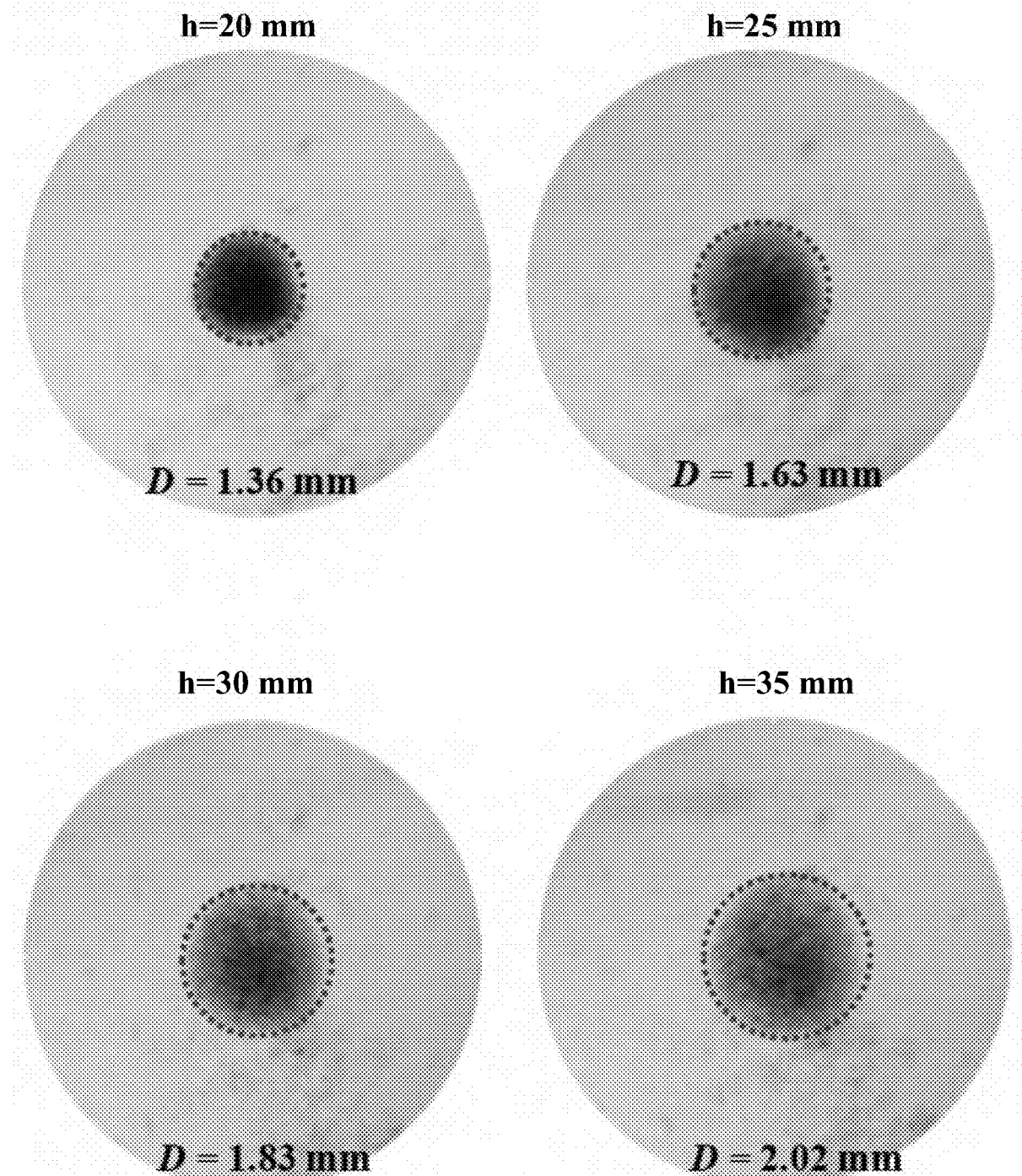
FIG. 18B illustrates a microparticle swarm on a working plane with different h values of 20, 25, 30, and 35 mm respectively at a frequency of 10 Hz in accordance with certain embodiments.

FIGS. 18A and 18B illustrate aggregation states of microparticle swarms when changing working plane's height h and magnetic field's rotating frequency f in accordance with certain embodiments. Height h is the distance or height of a working plane relative to a reference plane.

FIG. 18A illustrates a microparticle swarm on the working plane with h=20 mm, but at various frequencies ranging from 6.66 Hz to 50 Hz. It can be seen that the size of the formed microparticle swarm increases as the rotating frequency increases. The increased size of the swarm indicates decreased aggregation effect. That is, FIG. 18A indicates the increased frequency makes it harder to confine the microparticles. When the frequency reaches 50 Hz, the microparticles no longer stay together, but rather are scattered.

In FIG. 18B, the working planes are initialized with different h values of 20, 25, 30, and 35 mm respectively at a frequency of 10 Hz. It can be seen that when h increases, the size of the formed microparticle swarm increases, indicating a decreased aggregation ability or aggregation effect.

Figure 19:
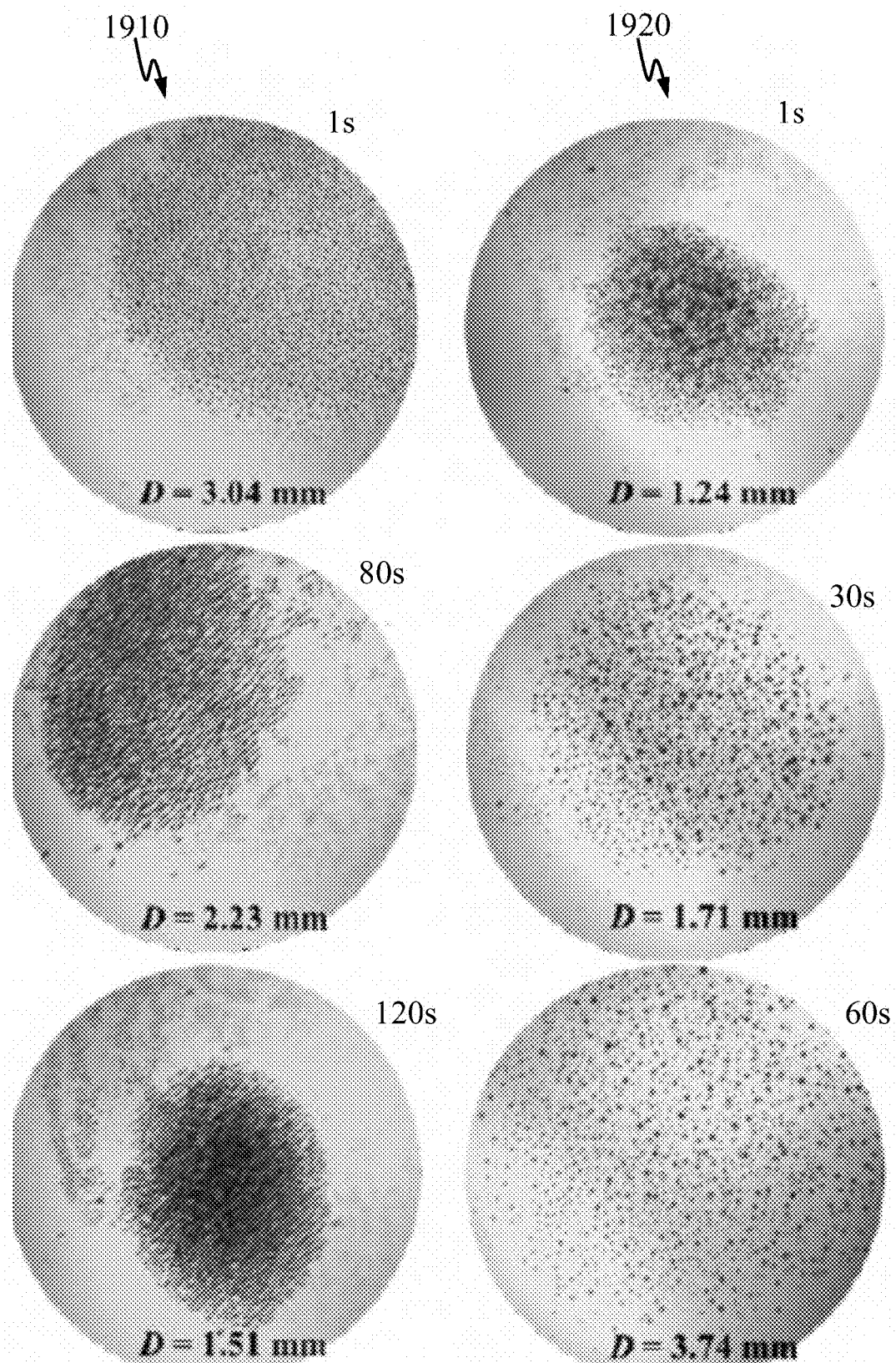
FIG. 19 illustrates motion performance characterization of microagent swarm in accordance with certain embodiments.
Figure 19:
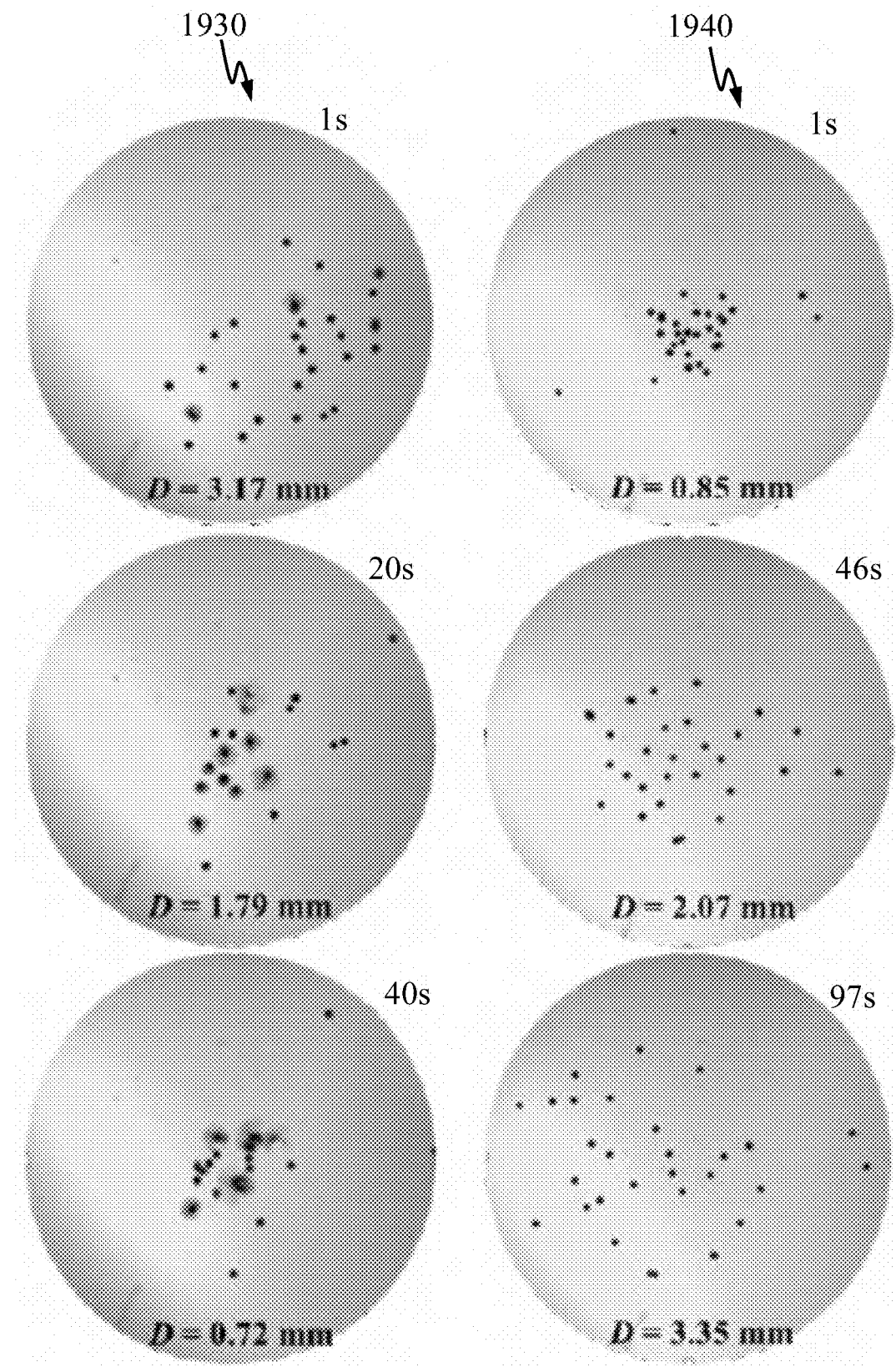

FIG. 19 illustrates motion performance characterization of microagent swarm in accordance with certain embodiments. Motions 1910 and 1920 are related to a swarm of microparticles (diameter: 1 μm) under two different rotating frequencies (10 Hz and 50 Hz) respectively. Motions 1930 and 1940 are related to a swarm of microrobots (diameter: 80 μm) under two different rotating frequencies (10 Hz and 50 Hz) respectively.

At 10 Hz, the distribution area of the microparticles is reduced from a larger area at 1 s to a smaller area at 120 s, indicating that the microparticles successfully aggregate. When changing the rotating frequency from 10 Hz to 50 Hz, the microparticles expands to a larger area from 1 s to 60 s, suggesting that the microparticles scatter when the frequency is increased to a certain high value. Motions 1930 and 1940 show similar performance for microrobots.

Figure 20:
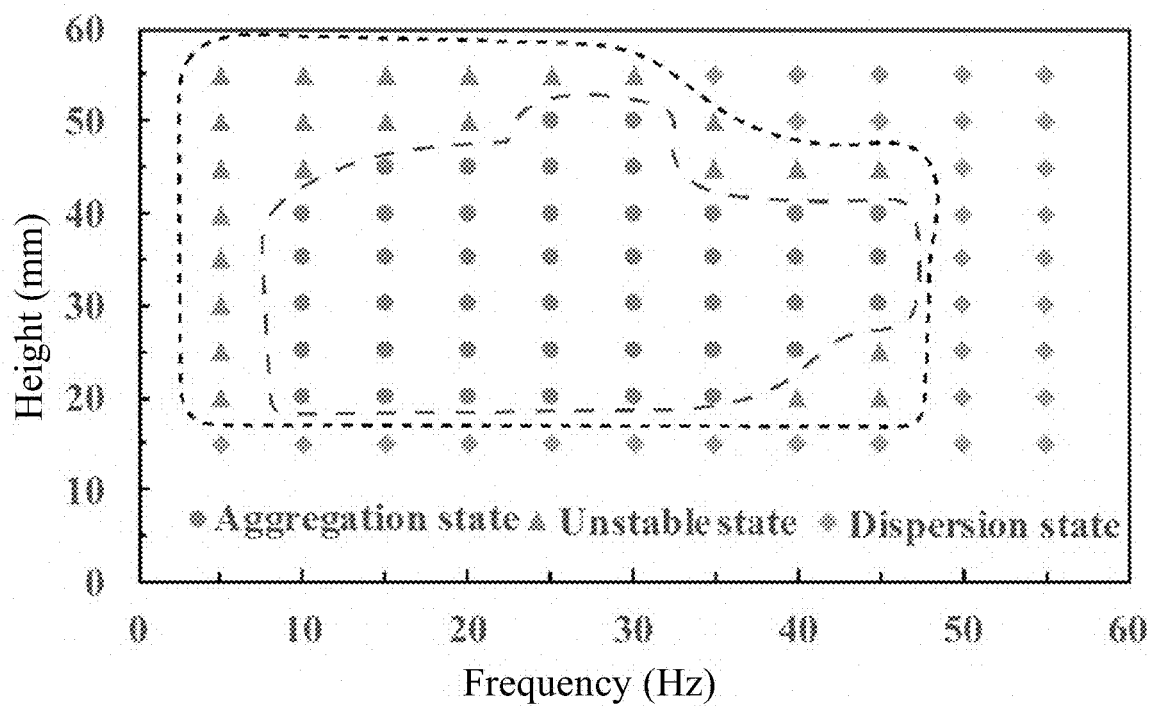
FIG. 20 illustrates a microparticle swarm tested on different working planes with h values ranging from 0 mm to 60 mm at different rotating frequencies in accordance with certain embodiments.

FIG. 20 illustrates a microparticle swarm tested on different working planes, with h values ranging from 0 mm to 60 mm at different rotating frequencies. Three different states are defined as "aggregation state," "dispersion state," and "unstable state". When the rotating frequency is in a low level, the microparticles aggregate and in the "aggregation state." When the rotating frequency increases to a high level, the microparticles scatter, and is in the "dispersion state." When the rotating frequency is in a critical level between the above two states, the microparticles appear unstable and in the "unstable state."

In certain embodiments, when the rotating frequency is in a range from 6 Hz to 34 Hz, the microparticles aggregate and in the "aggregation state." When the rotating frequency increases to above 48 Hz, the microparticles scatter and in the "dispersion state." When the rotating frequency falls in a range from 34 Hz to 48 Hz, the microparticles appear unstable and in the "unstable state."

FIG. 21A-21E illustrate in-vitro experiments of microagent aggregation control in microfluidic channels in accordance with certain embodiments.

According to the embodiment, experiments of aggregating microparticles in a microfluidic chip are conducted. The microfluidic chip is designed to simulate a blood vessel network for targeted delivery. Under action of a rotating magnetic field, a specific agglomeration area or aggregation area is formed, attracting microparticles from different channels. When the location of the aggregation area is changed by adjusting parameter c to respond to other disease sites for treatment, the microparticles located in the existing aggregation area are released and accumulate in a new aggregation area. Two microfluidic chips with different internal structures are designed to mimic two vascular environments of blood vessels and capillary network. The blood vessels with large diameters are usually used for injection because they can be easily detected and pierced.

Figure 21A:
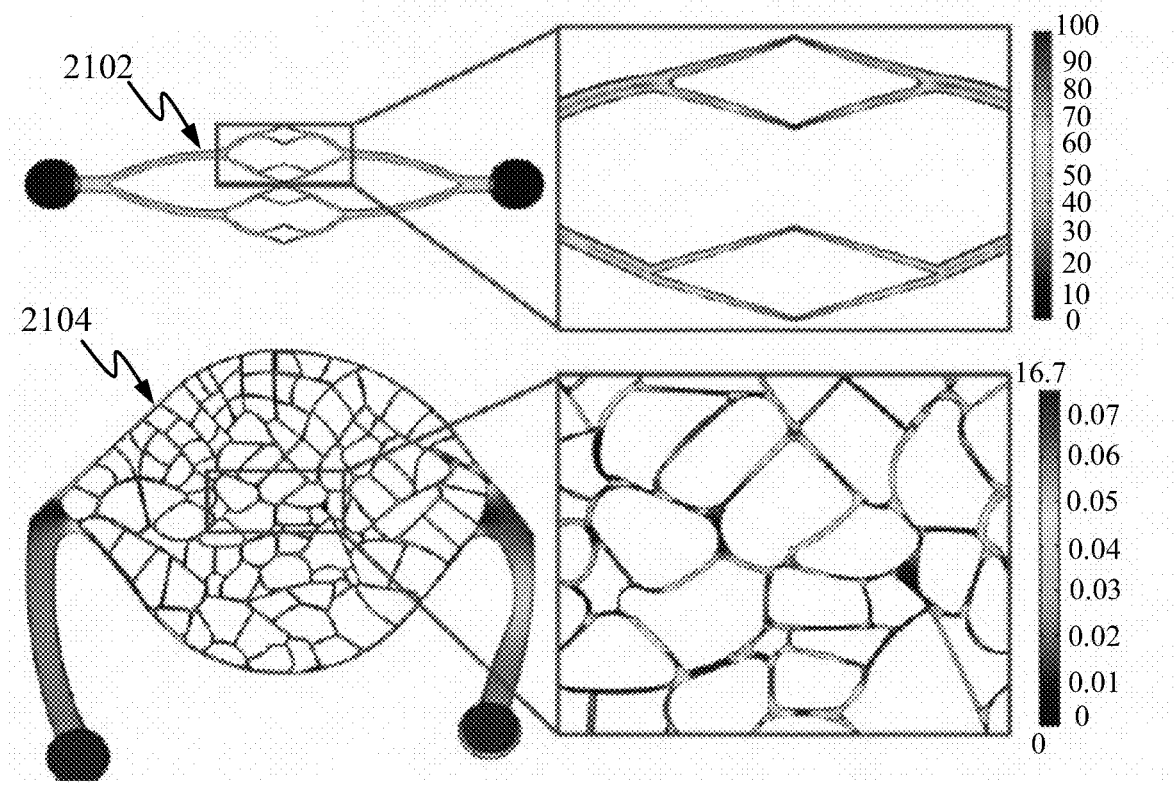
FIG. 21A illustrates flow simulation in binary channels (up) and nested channels (down) for in-vitro experiments of microagent aggregation control in microfluidic channels in accordance with certain embodiments.

FIG. 21A illustrates simulation results of the flow that can be uniformly distributed (less than 5% dispersion). Flow simulation in binary channels 2102 and nested channels 2104 is shown.

Figure 21B:
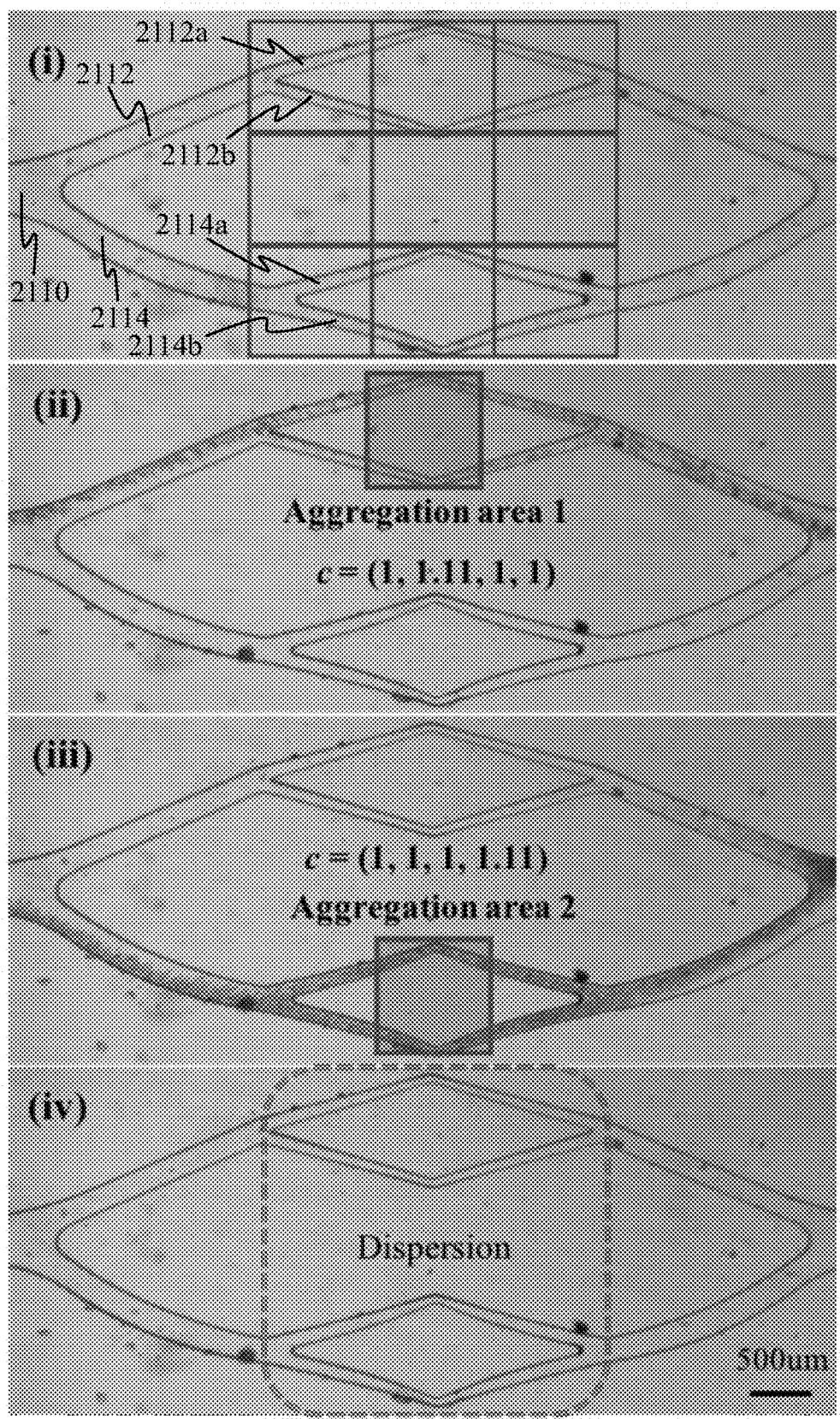
FIG. 21B illustrates enrichment of microparticles in different binary channels by adjusting aggregation centers for in-vitro experiments of microagent aggregation control in microfluidic channels in accordance with certain embodiments where (i) the microparticles are evenly distributed in the entire fluid channel at a flow rate of 3 μl/min; (ii) the microparticles are enriched in upper part; (iii) the microparticles are enriched in lower diamond-shaped microfluidic channels; and (iv) the microparticles scatter.

In an experiment as shown in FIG. 21B, in the entire microfluidic channel, a microfluidic chip with a diameter of 300 μm is used as a main channel (such as the main channel 2110 as shown in FIG. 21B(i)), which is separated into two subchannels (such as the subchannels 2112 and 2114 as shown in FIG. 21B(i)). Each subchannel is further separated into two branch channels (diameter: 50 μm) (such as the branch channels 2112a, 2112b, 2114a, and 2114b as shown in FIG. 21B(i)).

FIG. 21B shows enrichment of microparticles in different binary channels by adjusting the aggregation center or area. FIG. 21B(i) shows at a flow rate of 3 μl/min, the microparticles are evenly distributed in the entire fluid channel. Under the low-frequency rotating gradient magnetic field, the microparticles are enriched in upper part (see FIG. 21B(ii)) and lower diamond-shaped microfluidic channels (see FIG. 21B(iii)). Under a high-frequency rotating magnetic field, the microparticles scatter (see FIG. 21B(iv)).

Specifically, the microparticles are evenly distributed at the beginning (FIG. 21B(i)), and then are attracted to the upper and lower diamond-shaped microfluidic channels (FIG. 21B(ii) and FIG. 21B(iii)). These results suggest that under a rotating magnetic field, magnetic microparticles can move to different aggregation areas by entering different channels. When the frequency increases to 50 Hz, the microparticles first scatter and then are washed away by the fluid flow (FIG. 21B(iv)). A similar phenomenon can also be found in the nested channels of the simulated capillary network.

Figure 21C:
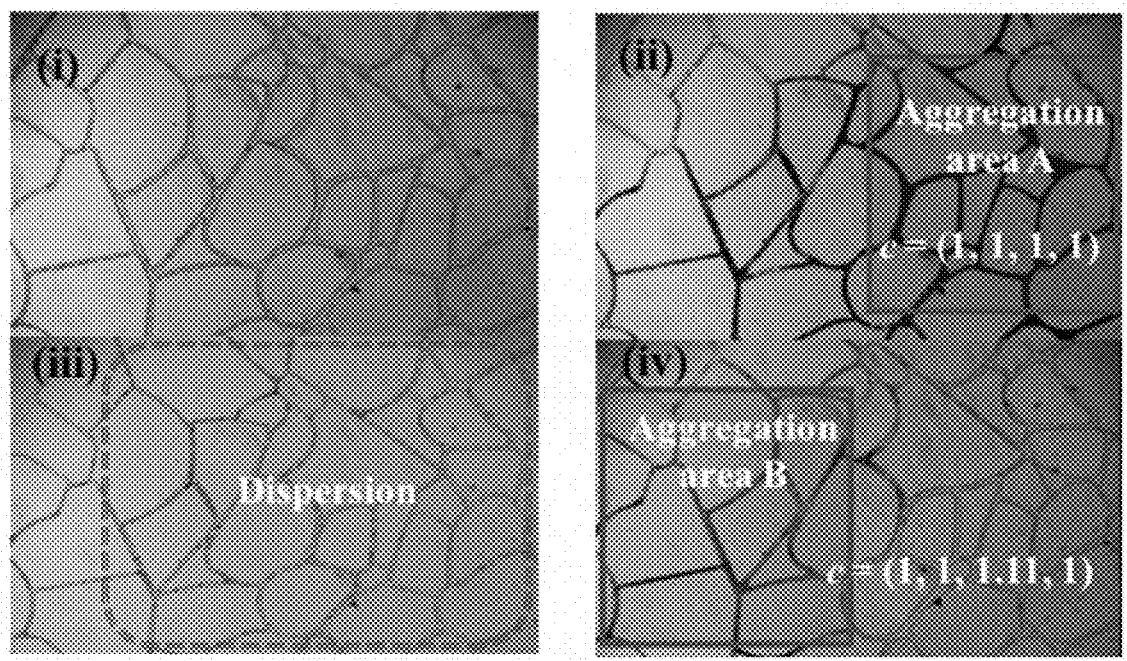
FIG. 21C illustrates enrichment of microparticles in different nested channels at low flow rates for in-vitro experiments of microagent aggregation control in microfluidic channels in accordance with certain embodiments where (i) the microparticles are evenly distributed at a flow rate of 1 μl/min; (ii) the microparticles are enriched in the aggregation area A; (iii) the microparticles are scattered; and (iv) the microparticles are enriched in the aggregation area B.

FIG. 21C illustrates enrichment of microparticles in different nested channels at low flow rates. At a flow rate of 1 μl/min, the microparticles are evenly distributed (FIG. 21C (i)), and then enriched in the aggregation area A (FIG. 21C(ii)) and the aggregation area B (FIG. 21C(iv)). The microparticles are scattered under a high-frequency rotating magnetic field (FIG. 21C(iii)). As shown in FIG. 21C, by changing the aggregation center or area defined by the rotating gradient magnetic field, magnetic particles are enriched in different areas of the channels.

Figure 21D:
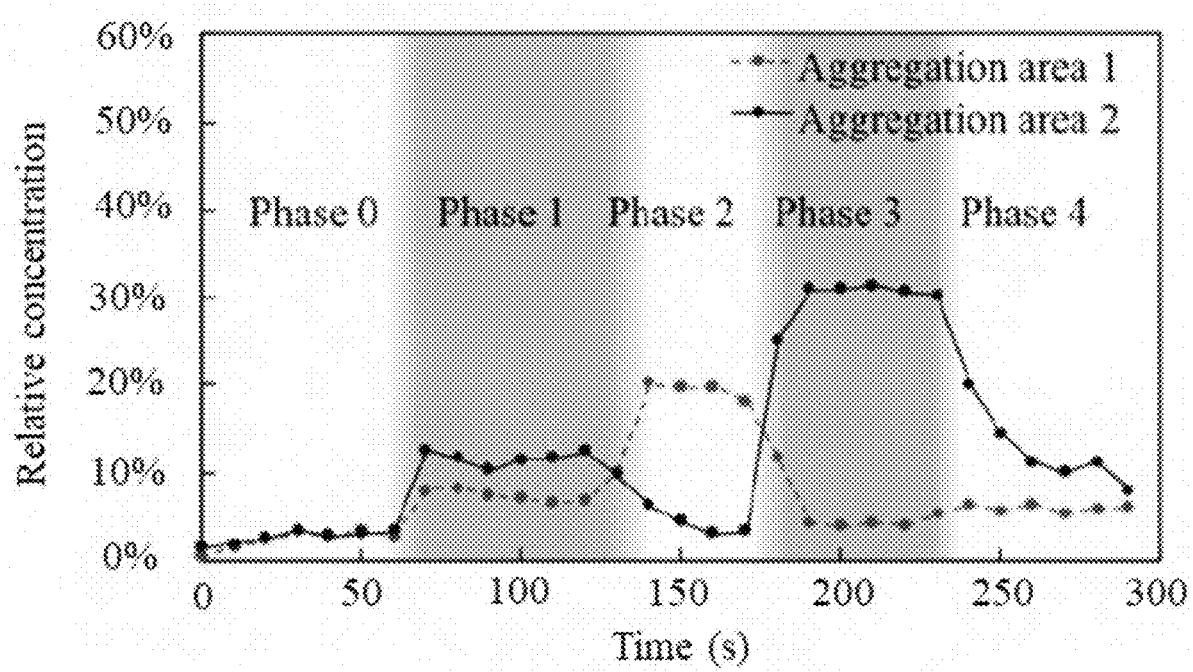
FIG. 21D illustrates concentration degrees of microparticles of FIG. 21B at different times.

FIG. 21D illustrates concentration degrees of microparticles of FIG. 21B at different times. A concentration degree represents density of microparticles in aggregation, and its value can be calculated by image processing in Python OpenCV. Phase 0 represents the initial state where no microparticle passes through the fluid channel and can be used as a reference in image processing. When microparticles flow into a binary channel, the concentration degree is displayed in Phase 1, which is higher than that in Phase 0. Note that the concentration degrees of the aggregation areas 1 and 2 are close to each other, indicating that the flow is evenly distributed. Phase 2 represents the process of FIG. 21B(ii) where the microparticles are attracted by the rotating magnetic field in aggregation area 1. The concentration degrees of microparticles in aggregation area 1 increases sharply to a high level, whereas that in aggregation area 2 decreases. Phase 3 represents the process of FIG. 21B(iii) in which the concentration degree in the aggregation area 2 increases significantly, whereas that in aggregation area 1 decreases. Phase 4 represents the dispersion process where the concentration degrees of the two areas decrease at the initial level.

Figure 21E:
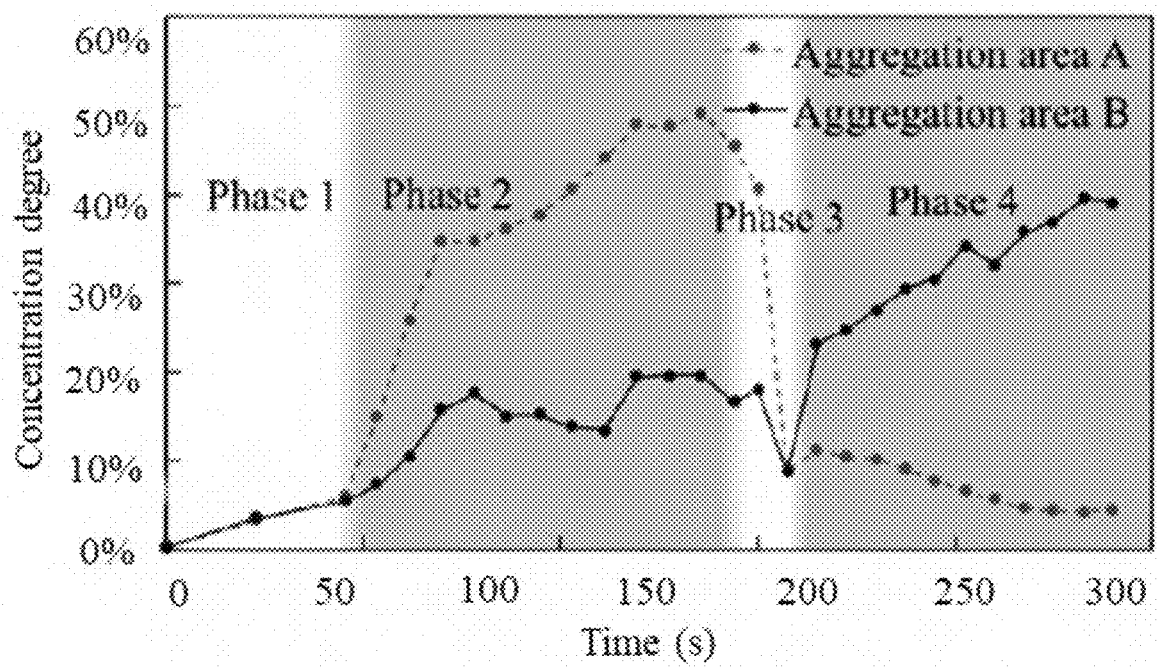
FIG. 21E illustrates concentration degrees of microparticles in the nested channel of FIG. 21C.

FIG. 21E illustrates concentration degrees of microparticles in a nested channel. Phases 1-4 represent the processes in FIG. 21C(i)-(iv) respectively.

Figure 22A:
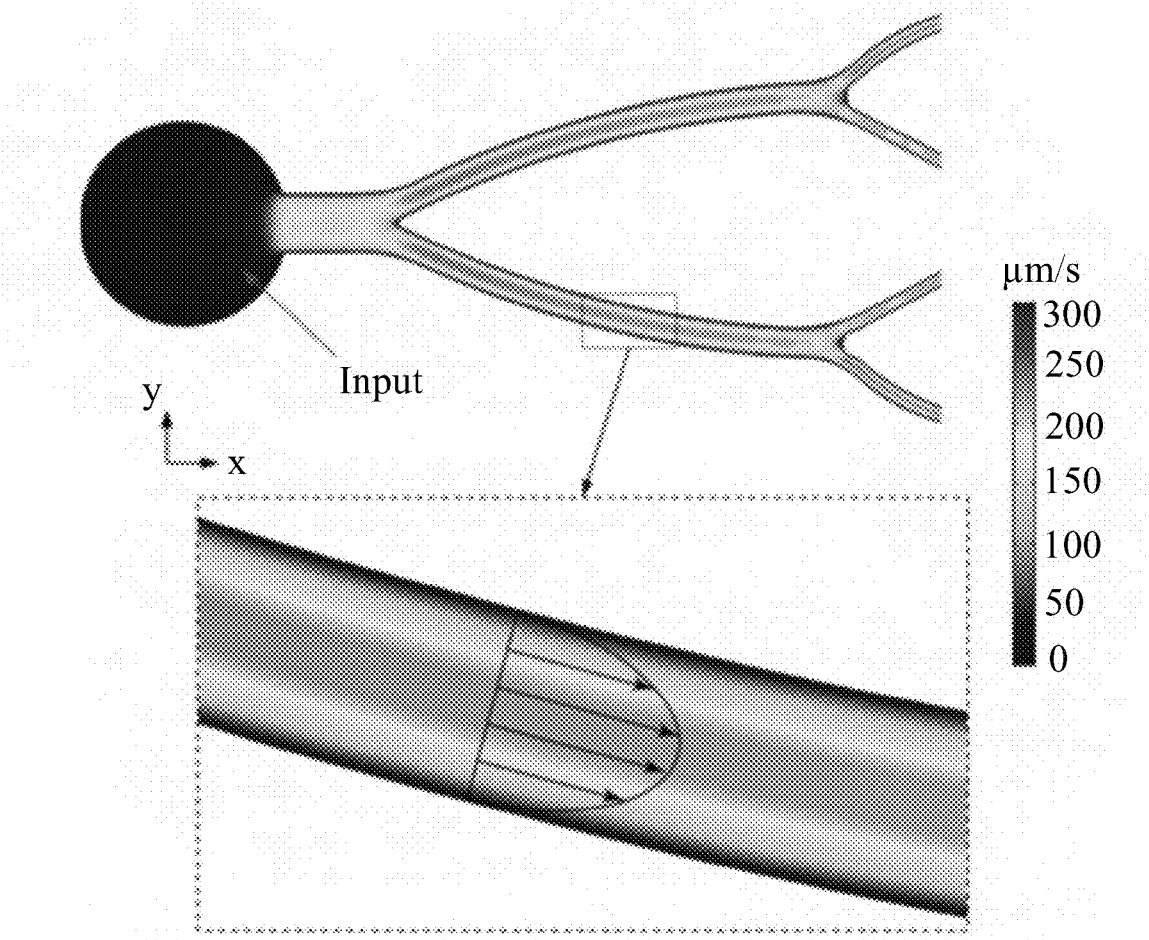
FIG. 22A illustrates flow fluid simulation results in a microfluidic channel where liquid flow in binary channels with the input velocity of 1 μl/min in accordance with certain embodiments.
Figure 22B:
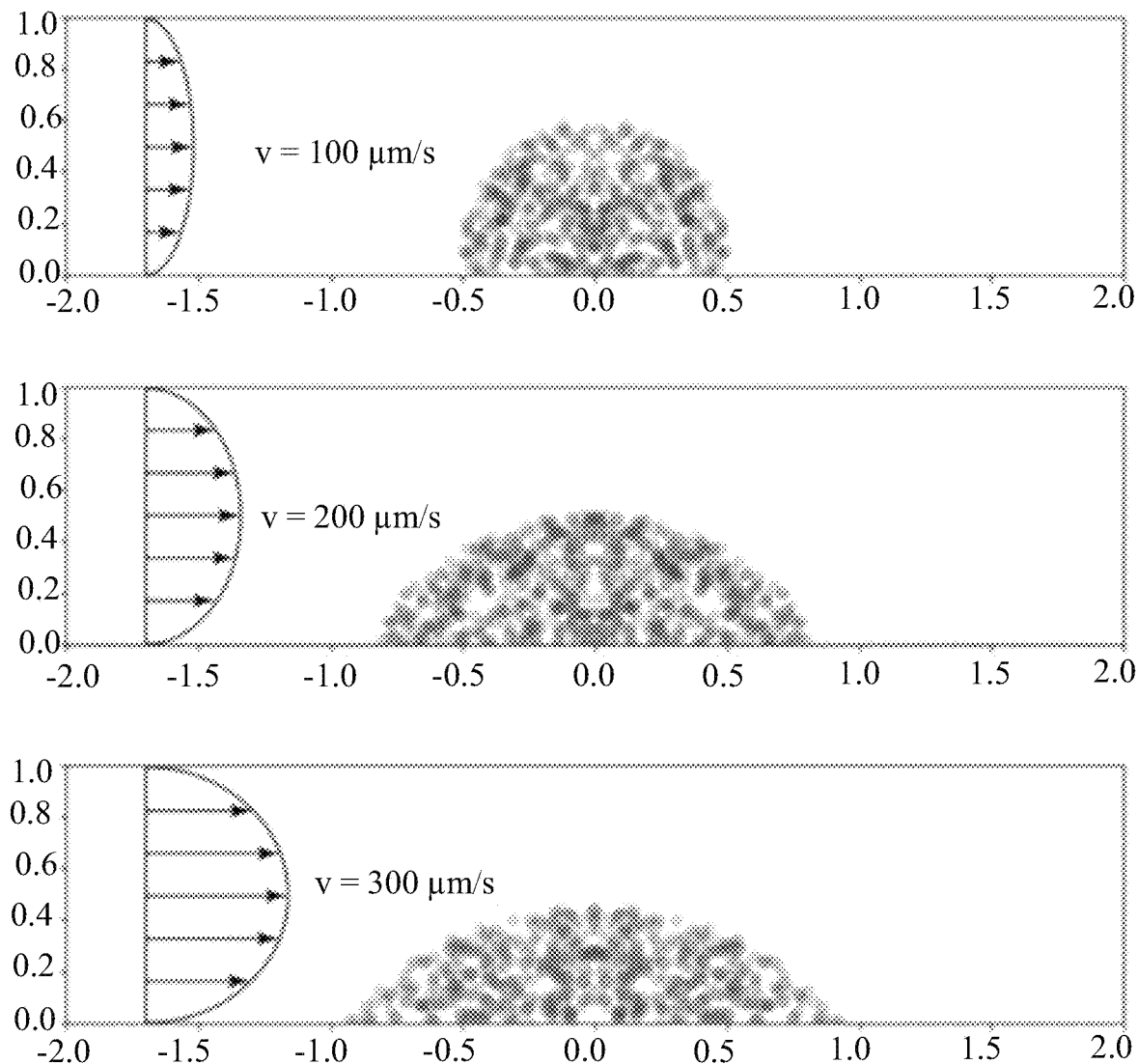
FIG. 22B illustrates flow fluid simulation results in a microfluidic channel showing microagent swarms in the flow channel when they are trapped by a rotating gradient magnetic field (I=2.5 A, f=20 Hz) in accordance with certain embodiments.

FIGS. 22A-22B illustrate flow fluid simulation results in a microfluidic channel. FIG. 22A shows liquid flow in binary channels with the input velocity of 1 μL/min. FIG. 22B shows microagent swarms in the flow channel when they are trapped by a rotating gradient magnetic field (I=2.5 A, f=20 Hz). As the velocity increases, the microagent swarm is squeezed on the radial direction of the flow channel, demonstrating that the rotating gradient magnetic field can trap the microagents in a flow fluid environment.

Figure 23:
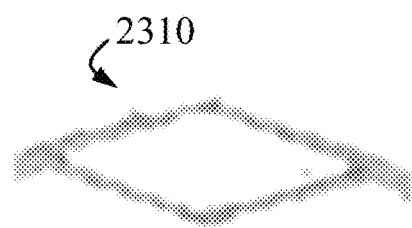
FIG. 23 shows calculation of concentration degrees in accordance with certain embodiments.
Figure 23:
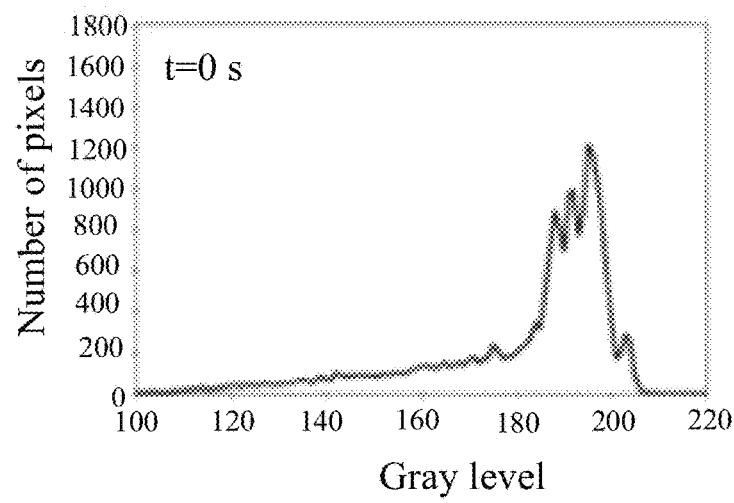
Figure 23:
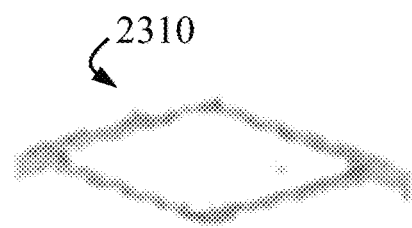
Figure 23:
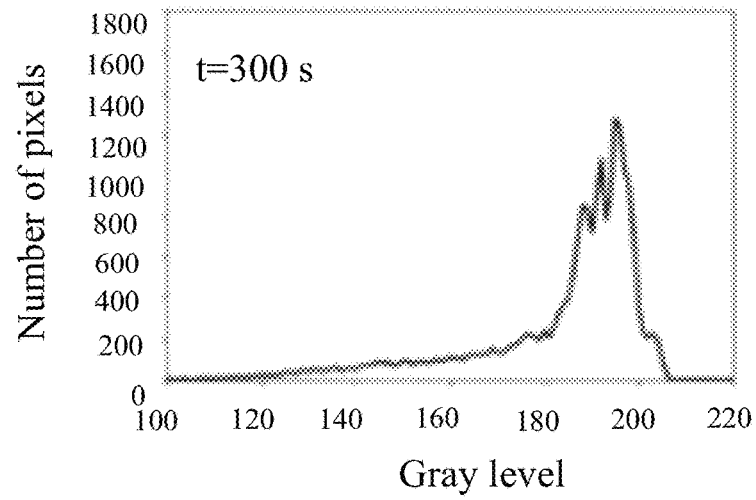
Figure 23:
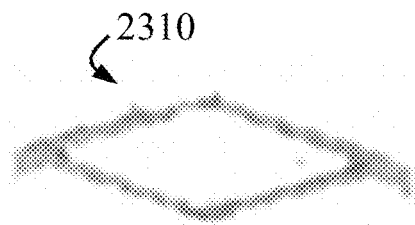
Figure 23:
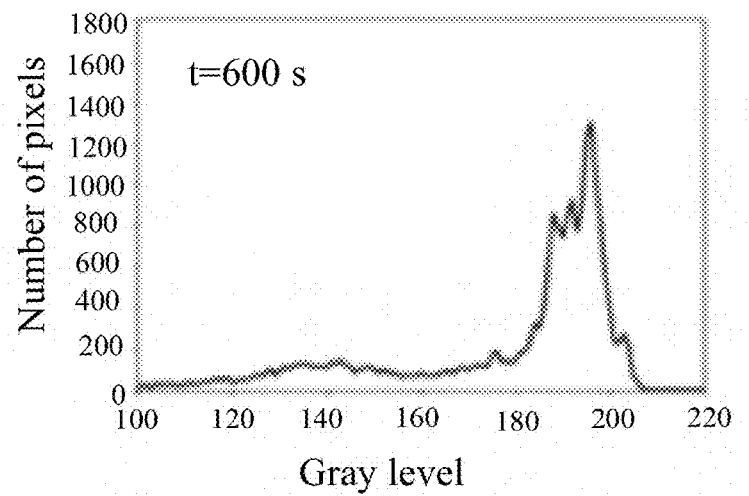
Figure 23:
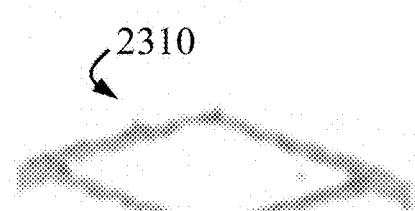
Figure 23:
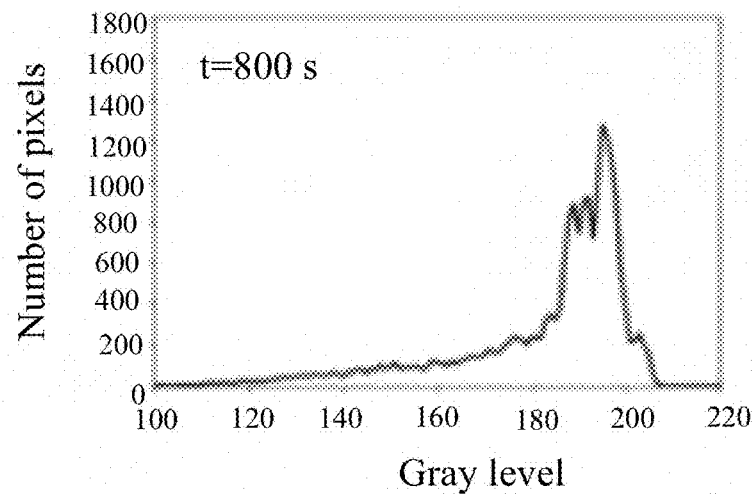
Figure 23:
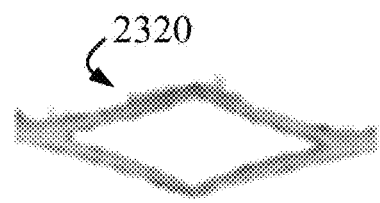
Figure 23:
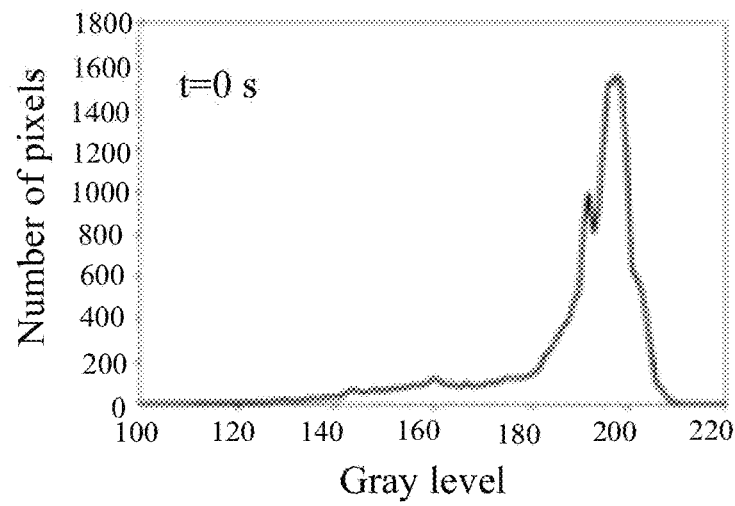
Figure 23:
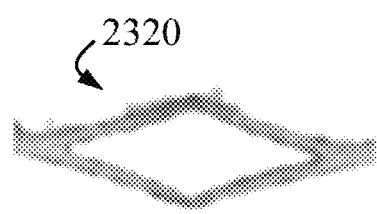
Figure 23:
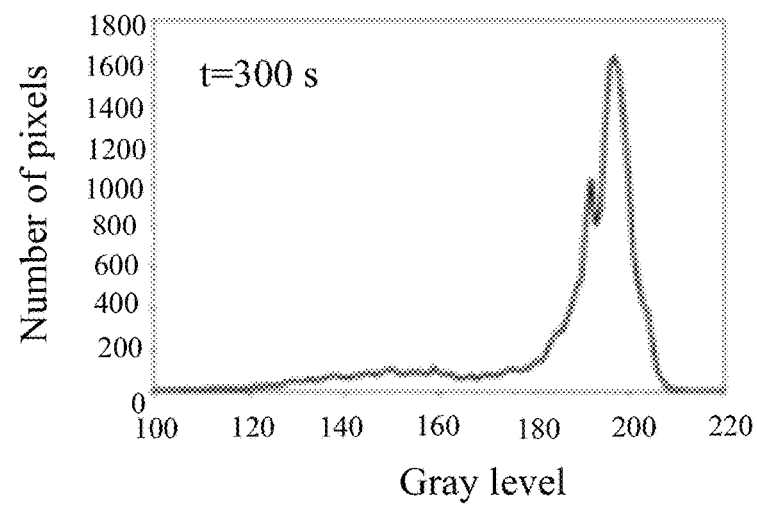
Figure 23:
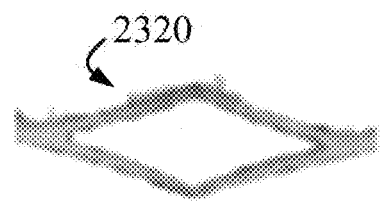
Figure 23:
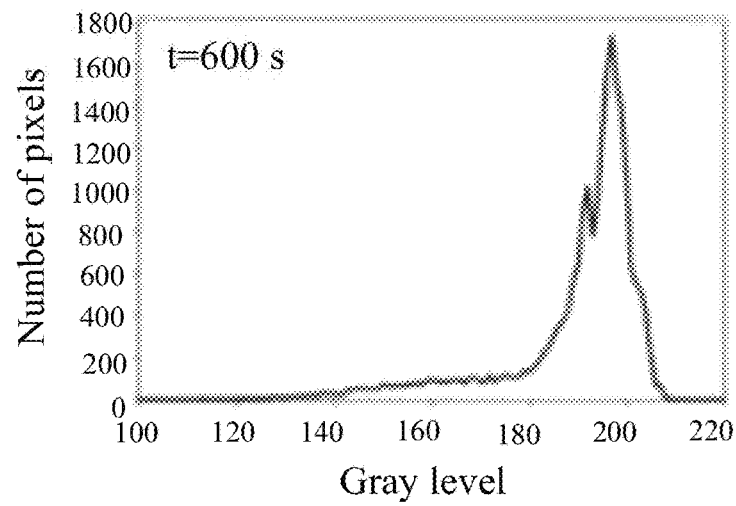
Figure 23:
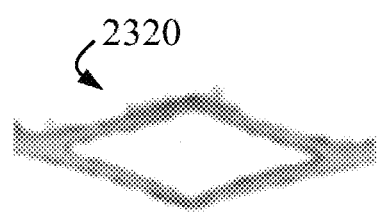
Figure 23:
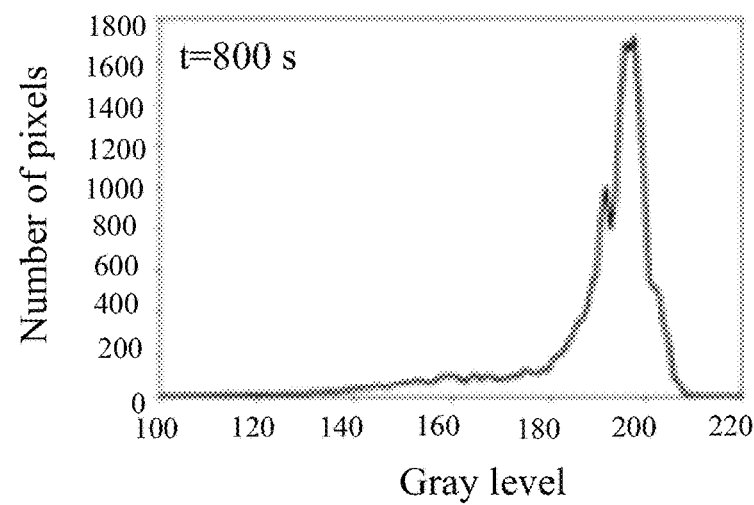
Figure 23:
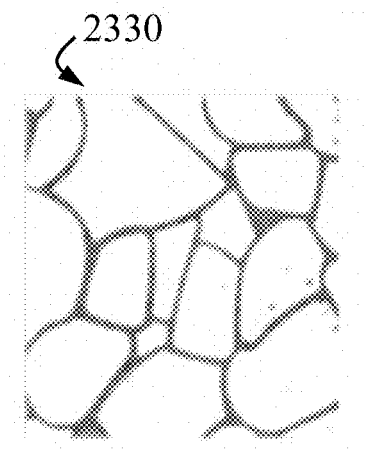
Figure 23:
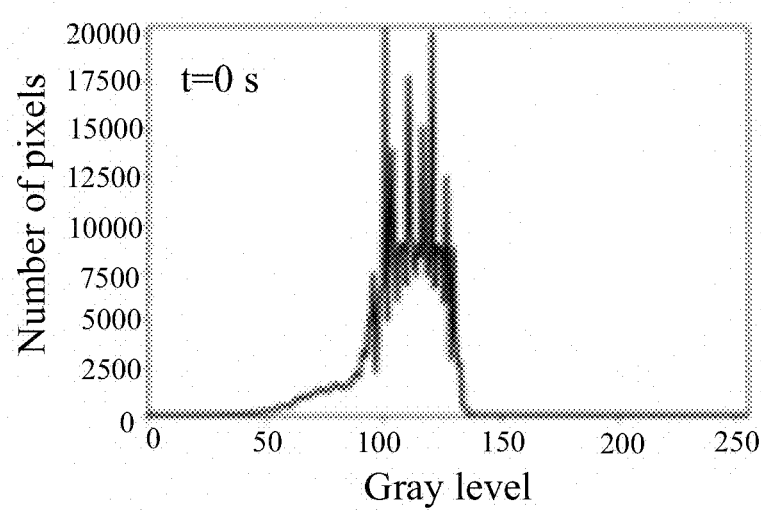
Figure 23:
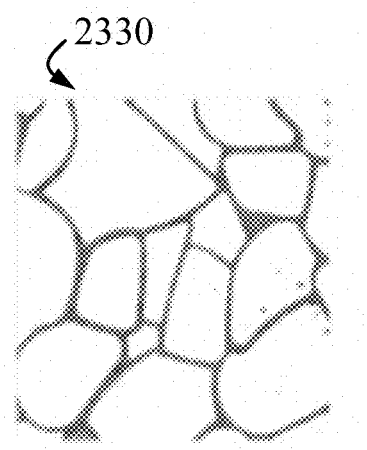
Figure 23:
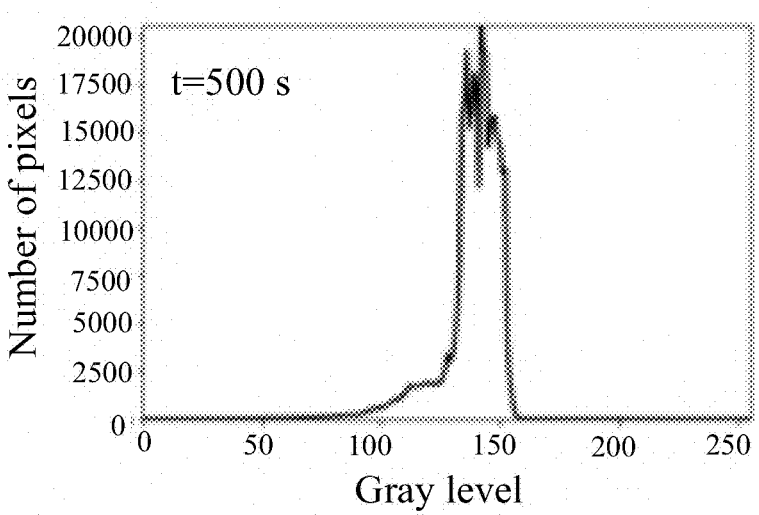
Figure 23:
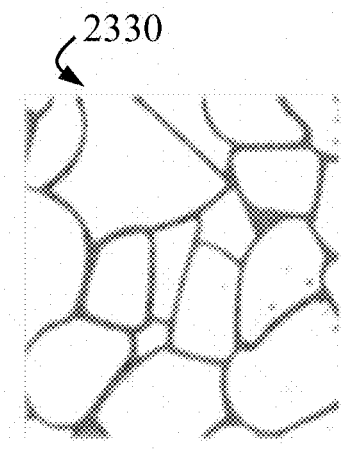
Figure 23:
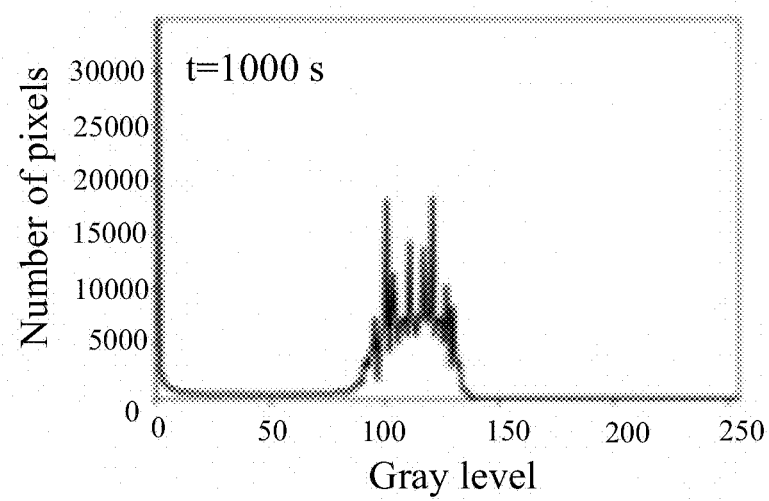
Figure 23:
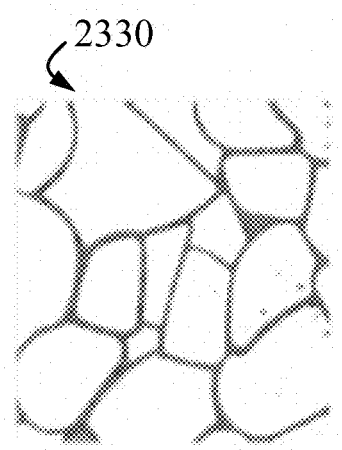
Figure 23:
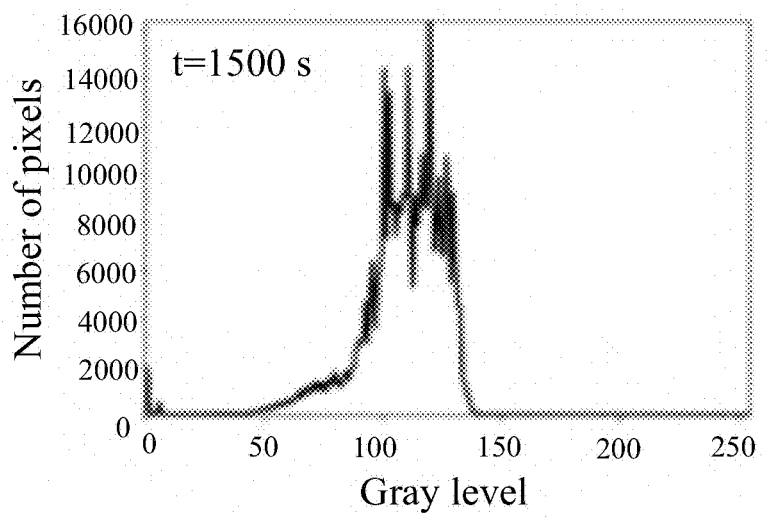
Figure 23:
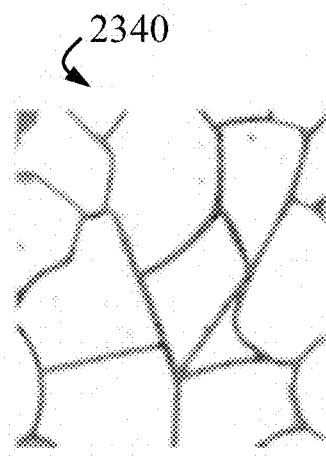
Figure 23:
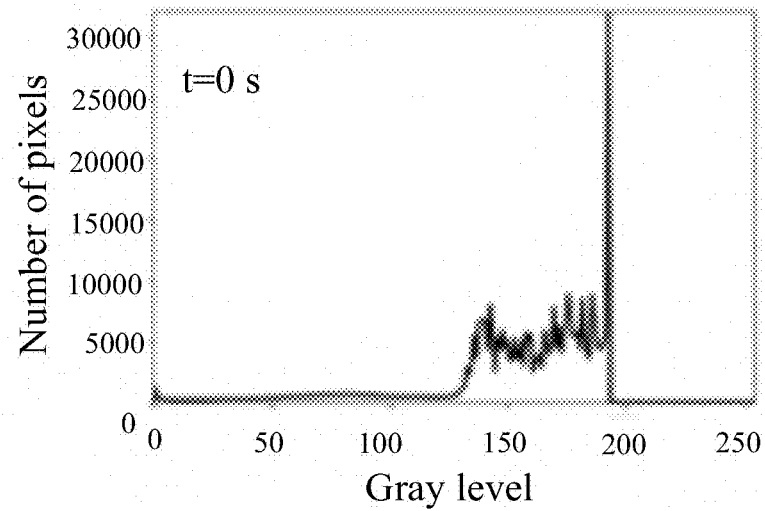
Figure 23:
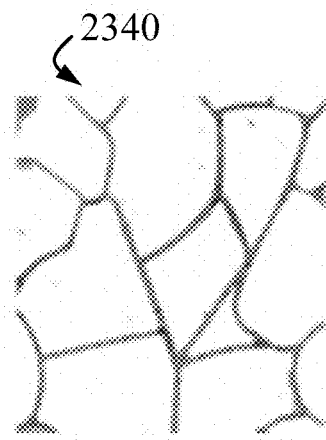
Figure 23:
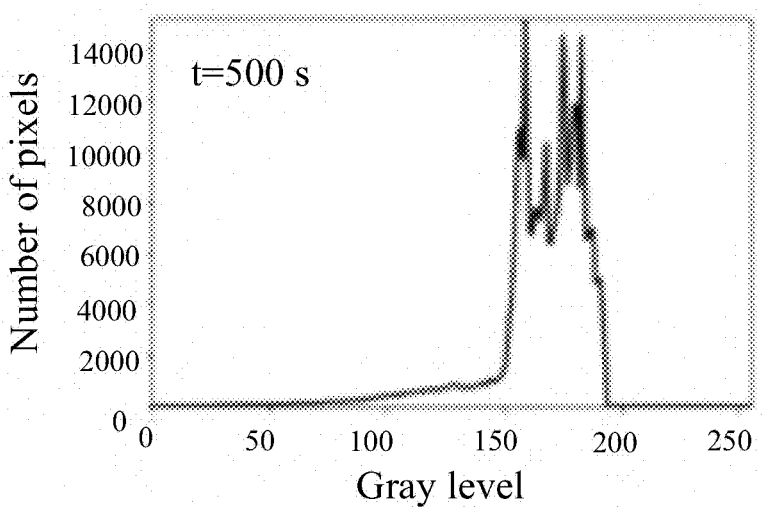
Figure 23:
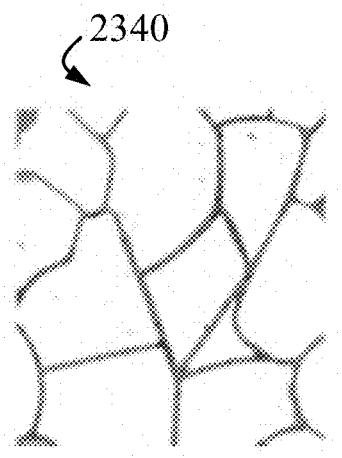
Figure 23:
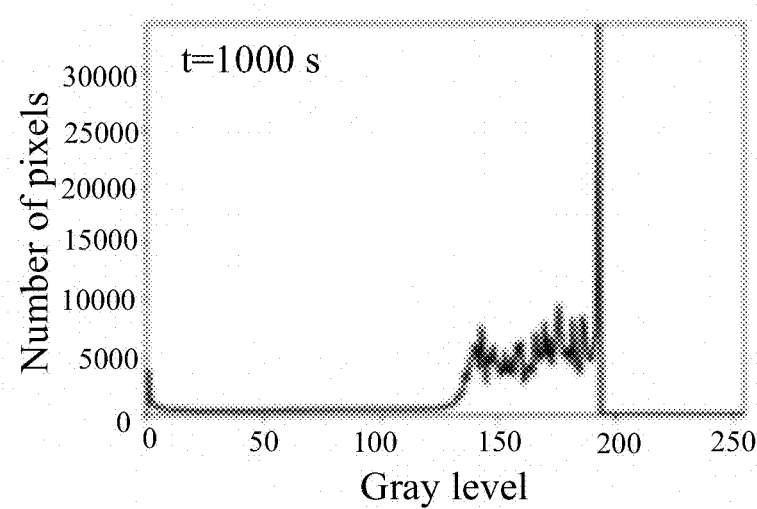
Figure 23:
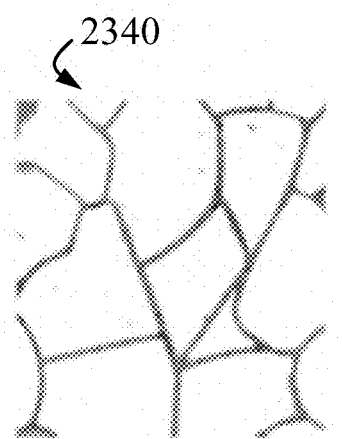
Figure 23:
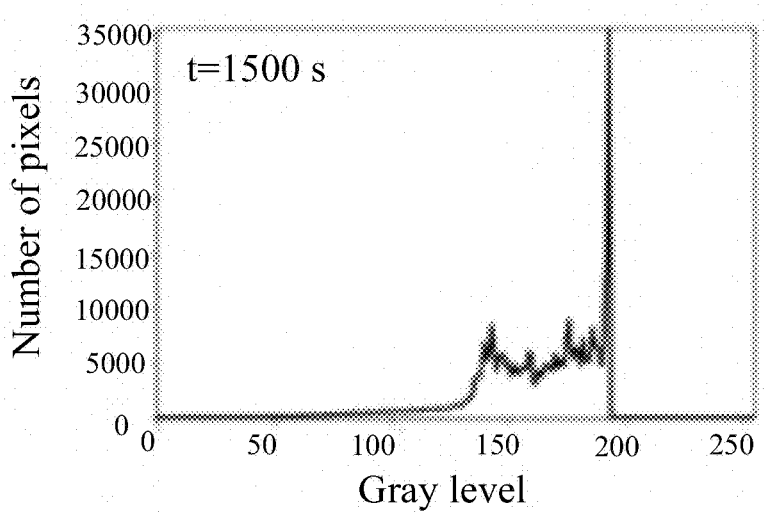

FIG. 23 shows calculation of concentration degrees. By way of example, aggregation areas 2310, 2320, 2330, and 2340 are aggregation areas 1, 2, A, and B in FIGS. 21A-21C. The images of flow channels are extracted from the original image, and the relationship between gray level and number of pixels is calculated at different time. When no microparticle passes through the fluid channel, the image is white (gray value=255), and the concentration degree is 0%; when the fluid channel is full of microparticles, the image is black (gray value=0), and the concentration degree is 100%. Using the statistical information of the imaging histogram, the concentration degrees of microparticles at different time can be calculated.

Figure 24A:
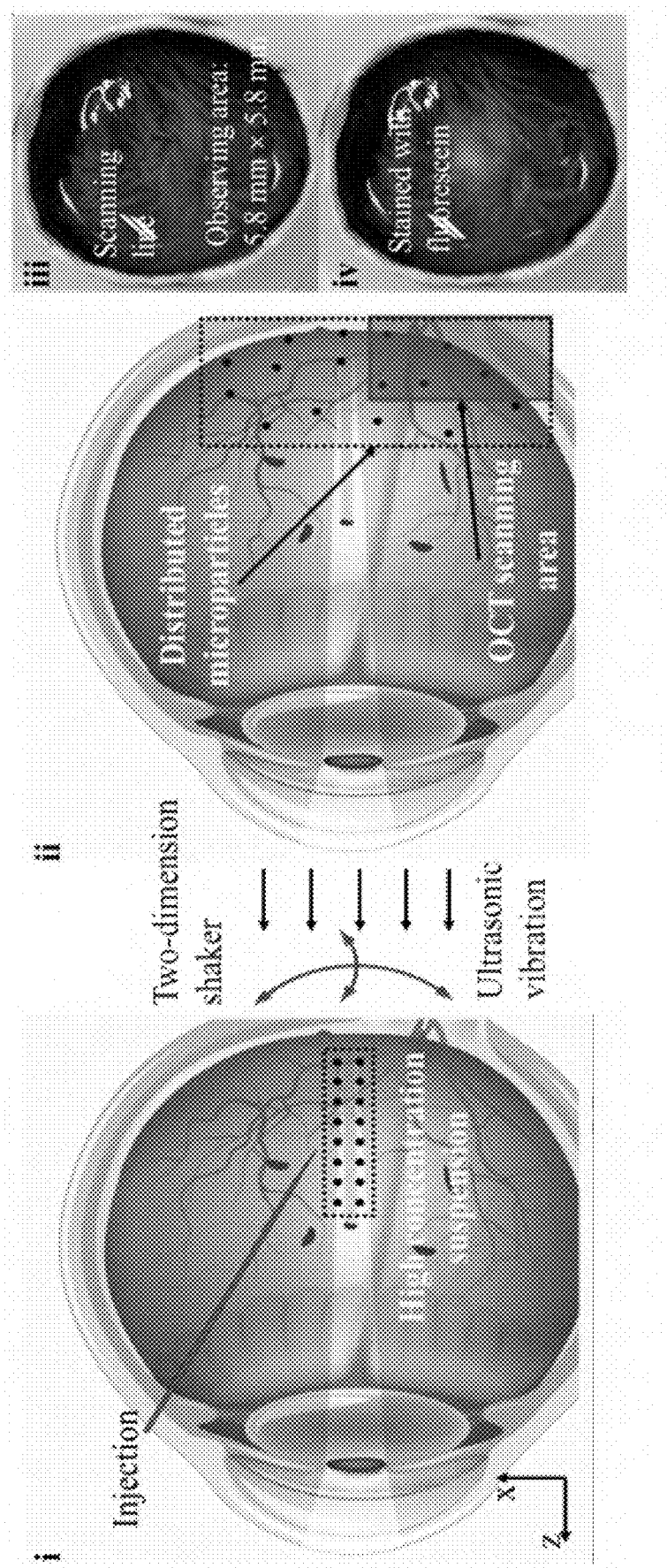
FIG. 24A illustrates ex-vivo experiments of microagent aggregation control and dispersion in a bovine eyeball in accordance with certain embodiments wherein (i) microparticles are injected into the fundus of the bovine eyeball; (ii) high-concentration suspension is dispersed to a uniformly distributed position through 2 D mechanical shaking and ultrasonic vibration; (iii) an observation area and scanning line of Optical Coherence Tomography (OCT); and (iv) an incised retina stained by the fluorescein released from the aggregated microparticles.
Figure 24B:
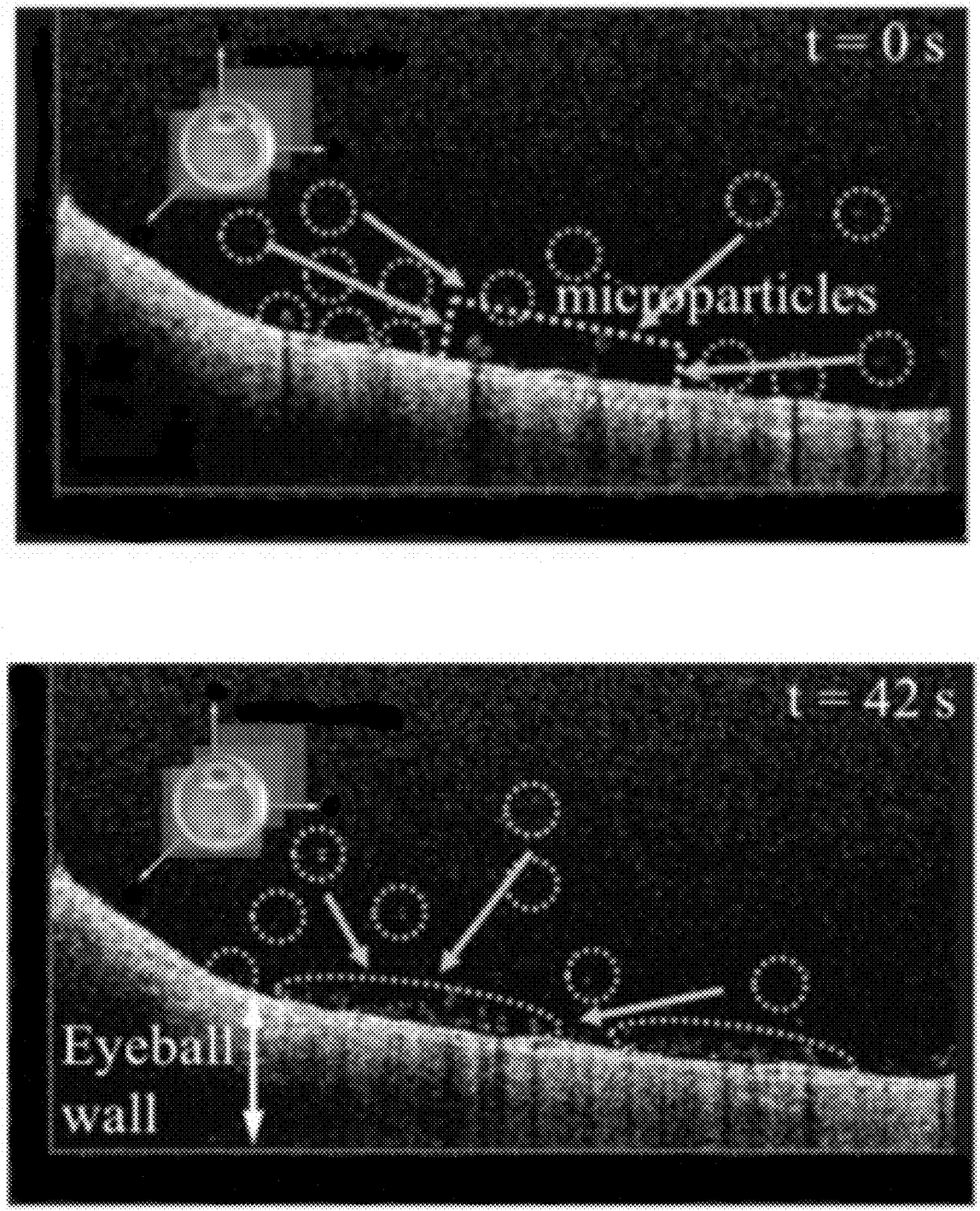
FIG. 24B illustrates an aggregation process of microparticles in 0-400 s and a dispersion process of microparticles in 400-750 s (I=2.5 A, f=15 Hz for aggregation, and f=66 Hz for dispersion) in the ex-vivo experiments of FIG. 24A.
Figure 24B:
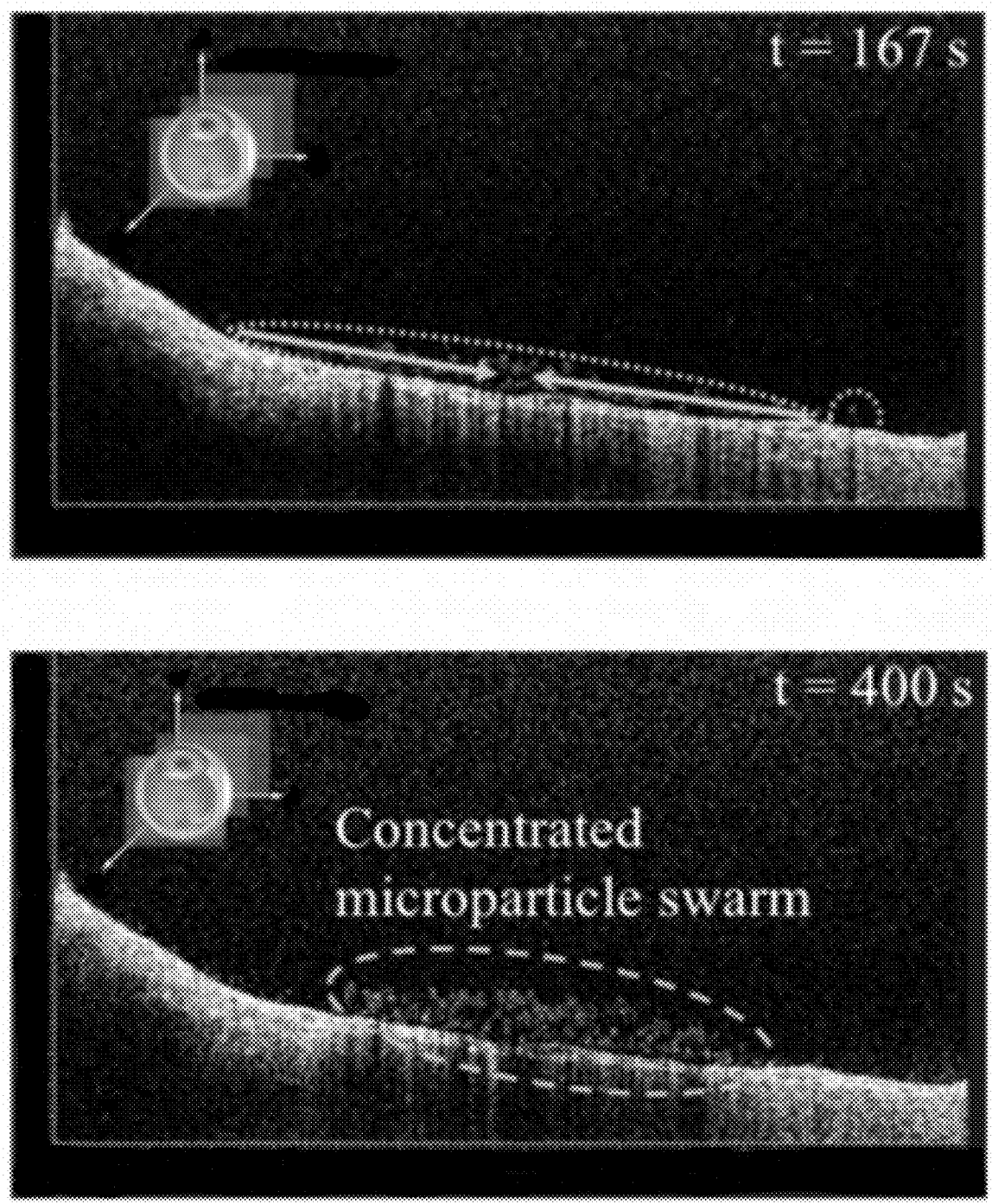
Figure 24B:
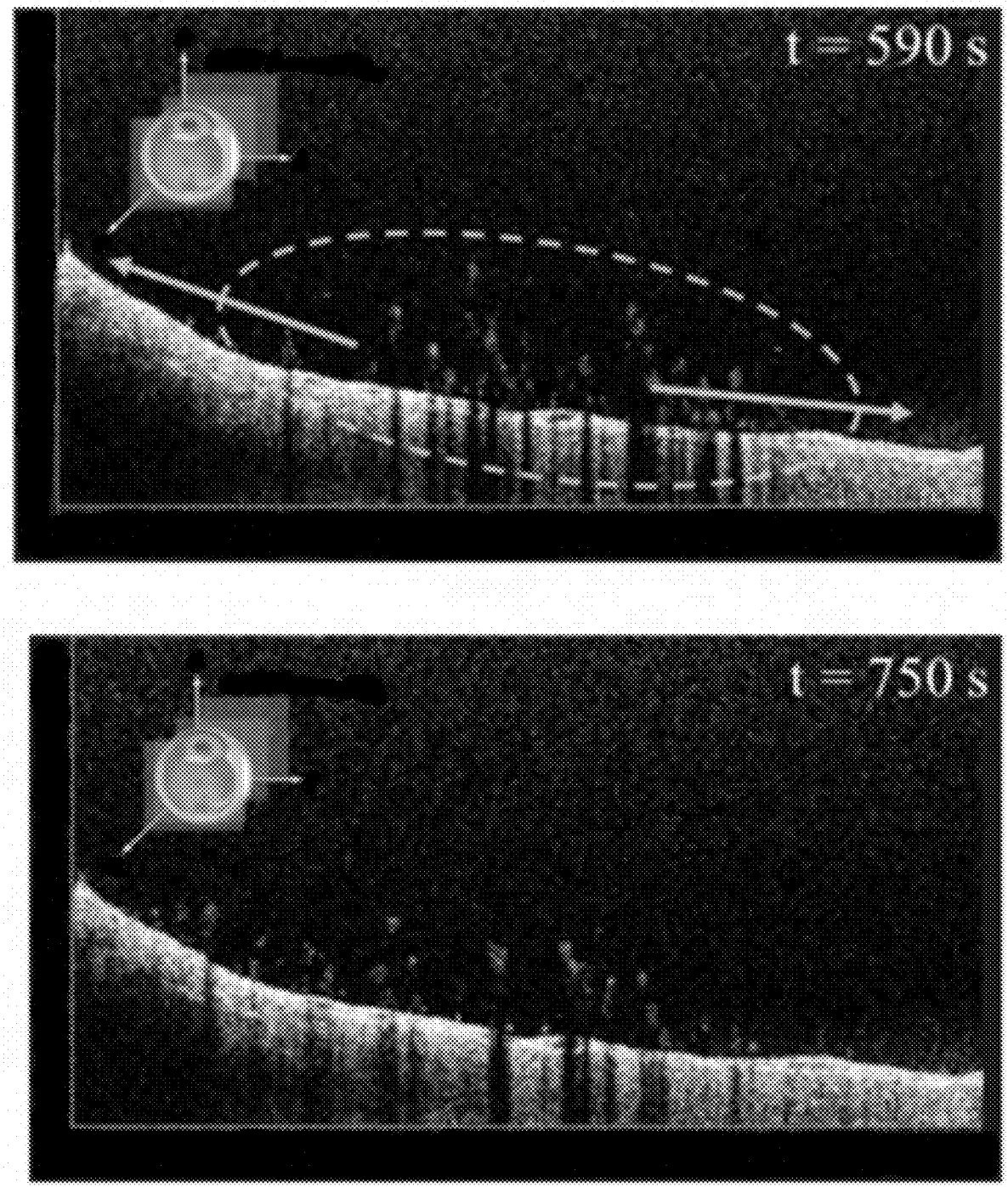
Figure 24C:
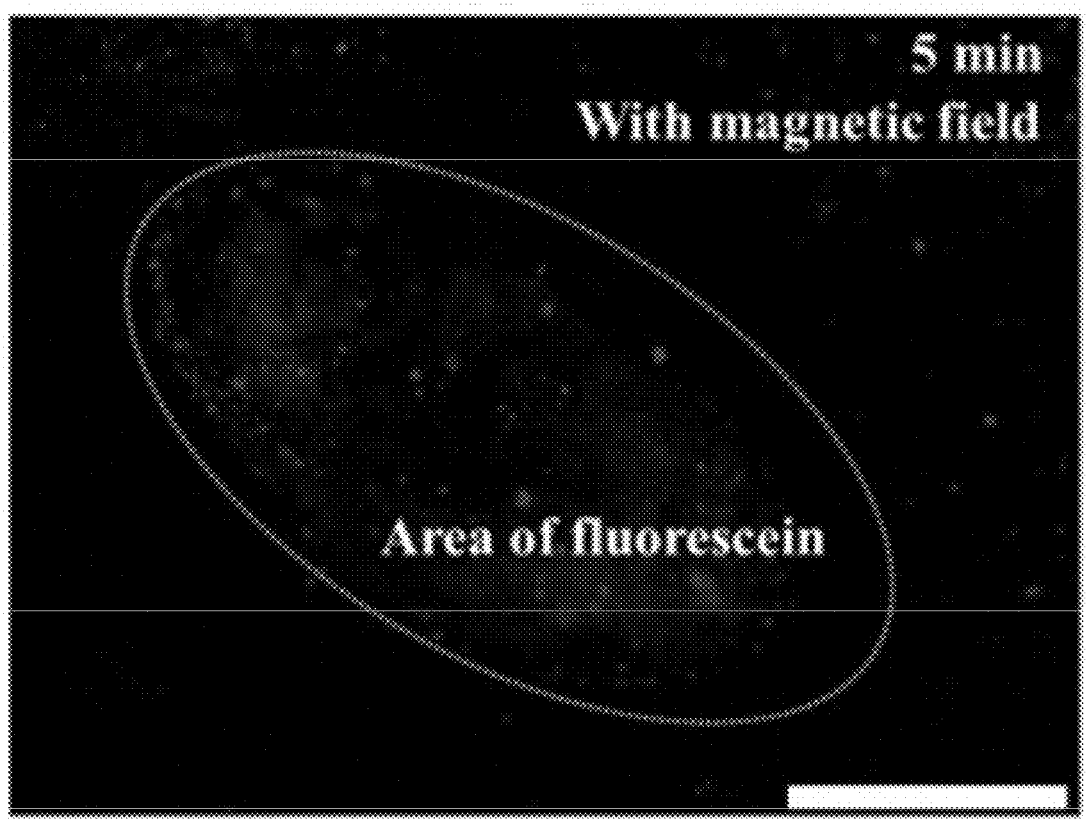
FIG. 24C illustrates fluorescent microscopy images of the incised retina stained by fluorescence microparticles with and without magnetic actuation control in the ex-vivo experiments of FIG. 24A.
Figure 24C:
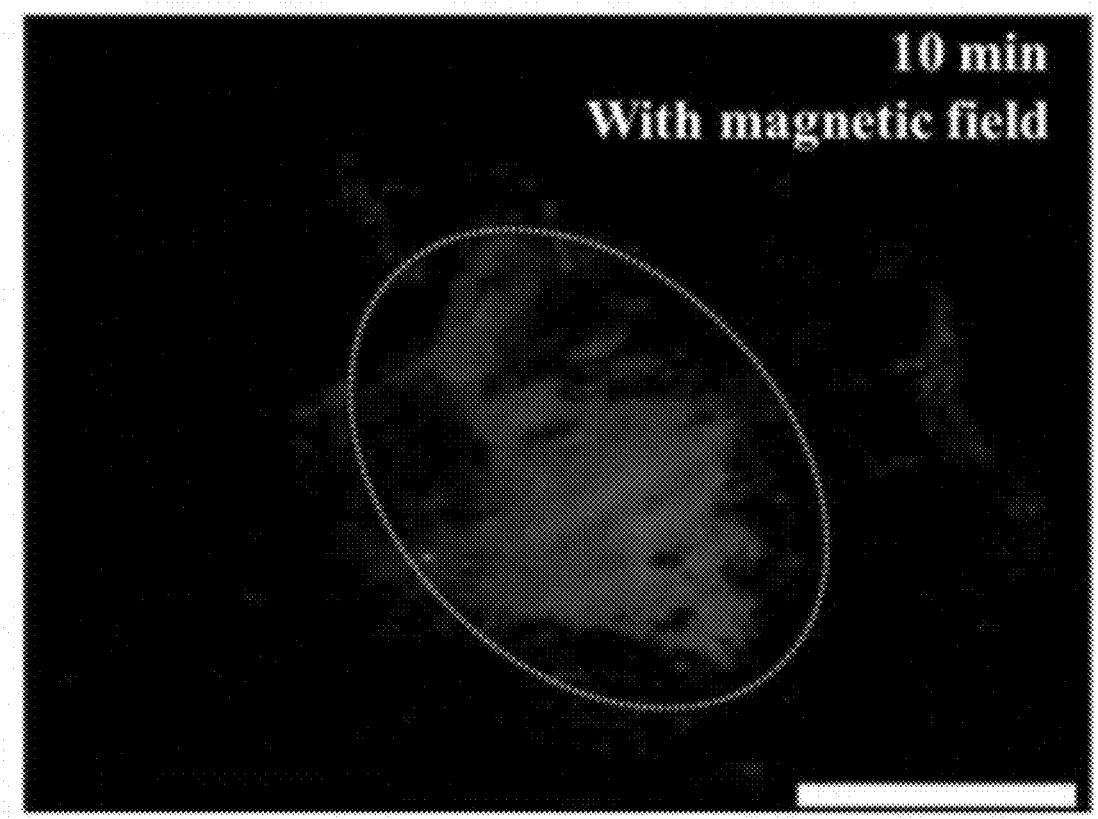
Figure 24C:
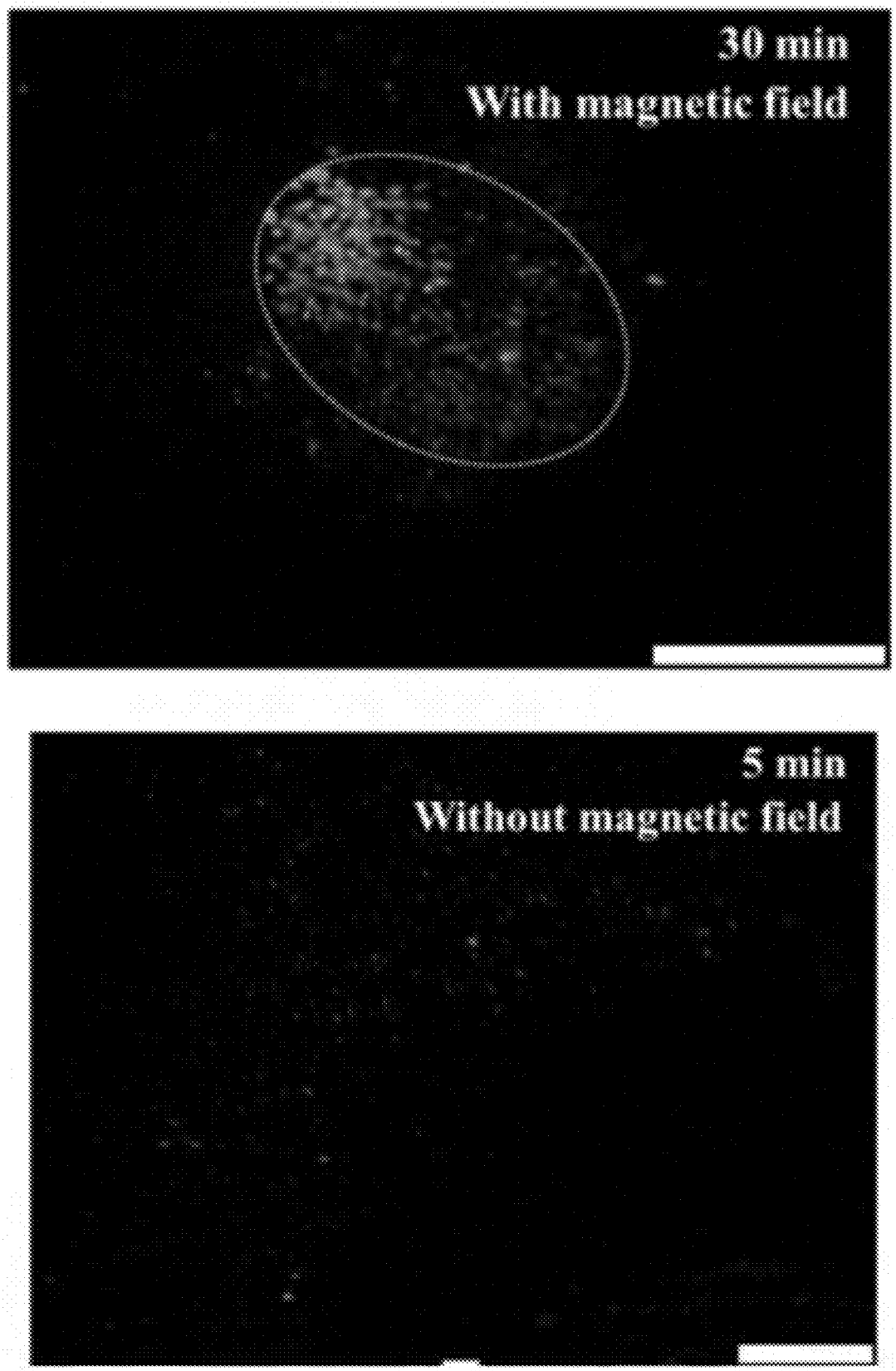
Figure 24C:
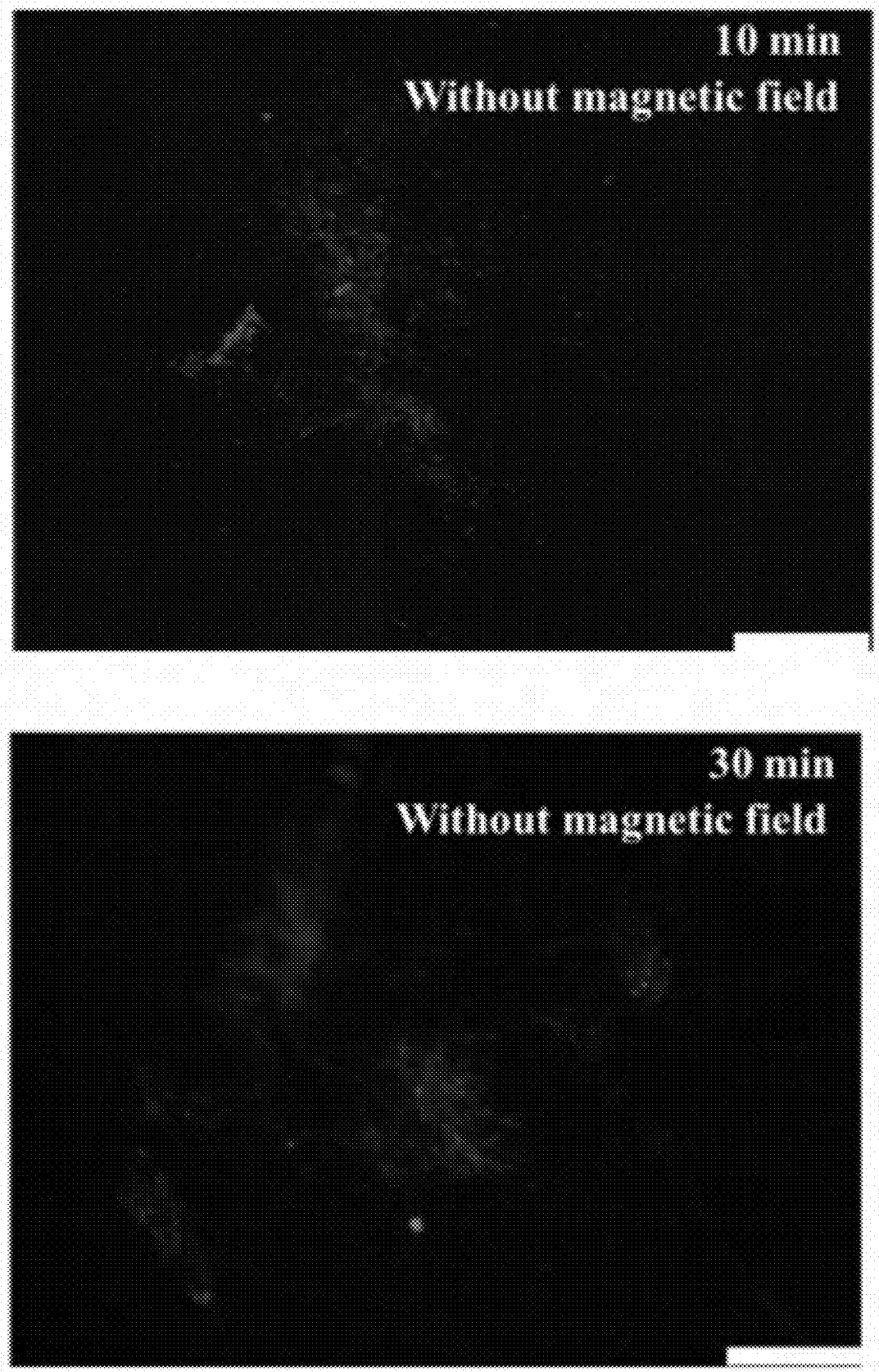
Figure 24D:
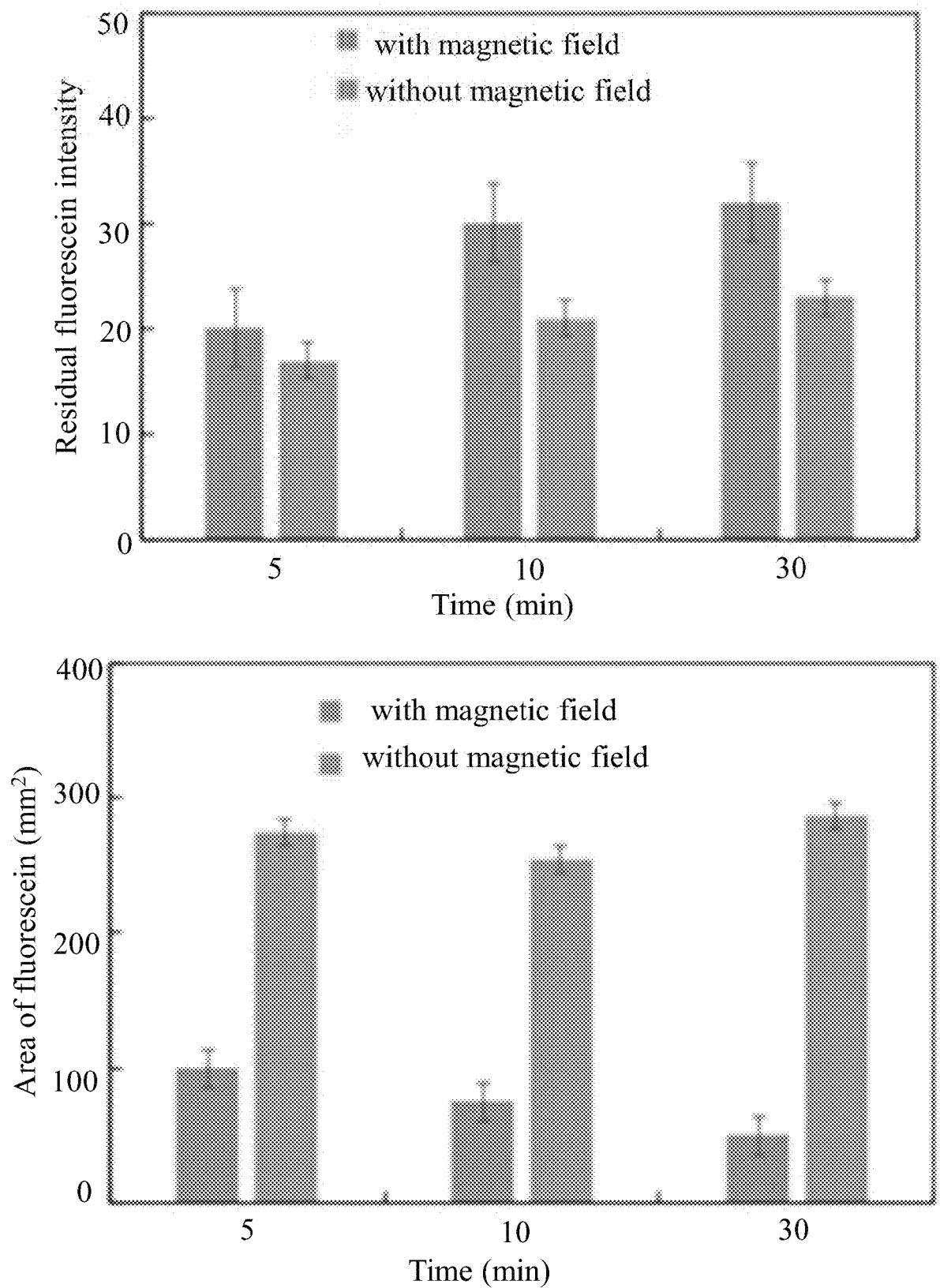
FIG. 24D shows quantitative data of the fluorescent microscopy images in FIG. 24C where the intensity and area of fluorescein are used to simulate the drug release process.

FIGS. 24A-24D illustrate ex-vivo experiments of microagent aggregation control and dispersion in a bovine eyeball. FIG. 24A is schematic of an experiment. FIG. 24A(i) shows microparticles are injected into the fundus of the bovine eyeball. FIG. 24A(ii) shows that high-concentration suspension is dispersed to a uniformly distributed position through 2 D mechanical shaking and ultrasonic vibration. The red dashed square and red solid line in FIG. 24A(iii) show the observation area and scanning line of OCT, respectively. The green sketch in FIG. 24A(iv) shows the incised retina stained by the fluorescein released from the aggregated microparticles. FIG. 24B illustrates an aggregation process of microparticles in 0-400 s and a dispersion process of microparticles in 400-750 s (I=2.5 A, f=15 Hz for aggregation, and f=66 Hz for dispersion). FIG. 24C illustrates fluorescent microscopy image of the incised retina stained by fluorescence microparticles with and without magnetic actuation control. The yellow dashed circle shows the fluorescence area in different situations. FIG. 24D shows quantitative data of the fluorescent microscopy image in FIG. 24C where the intensity and area of fluorescein are used to simulate the drug release process. The scale bars in FIGS. 24B-24C are 1 mm.

With regards to the ex-vivo experiments of controlling microparticles in the bovine eyeball, after being injected into the eyeball, the drug-loaded microparticles begin to slowly degrade, and the drugs are released through passive diffusion and stain the retina.

However, this passive diffusion to the retina can cause side effects and reduce the efficiency of passive diffusion. This problem can be overcome by using actively propelled microparticles. The physical properties of vitreous, such as density or viscoelasticity, may be unaffected by the small-dose injection of particle suspension, and the locomotion of microparticles may be also not dependent on the partial or overall dilution. In the present embodiment, a swarm of microparticles are injected into the bovine eyeball to demonstrate the feasibility of using rotating gradient magnetic field for microagent aggregation. The fluorescein bonded to the microparticles is used to demonstrate the drug release process. OCT and fluorescent microscopy are used to capture images. 0.1 ml of microparticle suspension (1 mg/mL) is injected into the posterior part of the eyeball (FIG. 24A(i)), and then subjected to 6 min of 2 D mechanical vibration and 0.5 min of ultrasonic vibration dispersion (FIG. 24A(ii)) to simulate the rehabilitation operation between the two consecutive treatment courses. Subsequently, a rotating gradient magnetic field is applied to trigger the aggregation process of the microparticles. The current of each coil is 2.5 A, and the rotating frequency is 15 Hz. FIGS. 24A(iii)-(iv) show aggregation process of the microparticle swarm. In FIG. 24A(iv), when the microparticles are degraded after 30 mins, the eyeball is stained by the released fluorescein, which can be used to simulate the drug release process for targeted therapy.

More specifically, FIG. 24B shows the process of aggregation and dispersion, where the length of the OCT scan line is 5.8 mm. Under a rotating magnetic field, the uniformly distributed particles gather into many clusters, as represented by the white pattern marked by the yellow dashed circle. At the same time, the microparticles begin to move toward the center of the OCT view, which is the desired aggregation center. When the distribution area of the microparticles is reduced, the image contrast of OCT is improved. Finally, the microparticles are concentrated around the aggregation center at 400 s. After increasing the frequency of the rotating magnetic field to 66 Hz within a period from 400 s to 750 s, the microparticles scatter.

Figure 25:
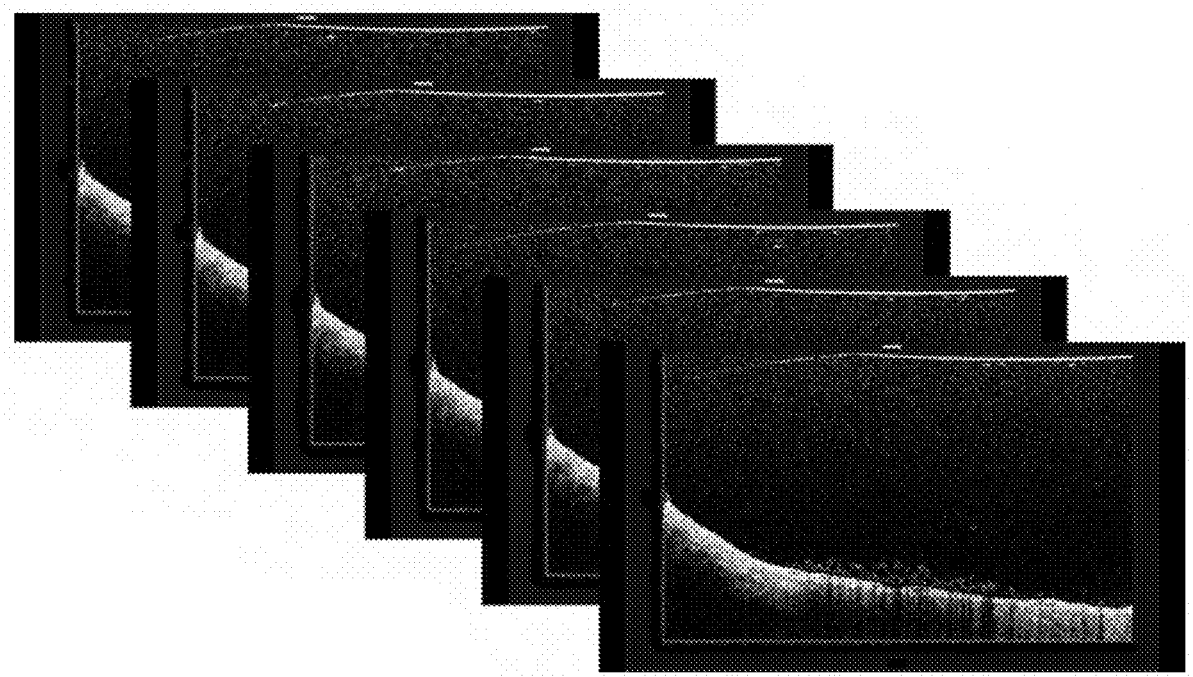
FIG. 25 shows a reconstructed the OCT image with slice-array images of gathered microparticles in accordance with certain embodiments.

More specifically, FIG. 24C shows the comparison result of the stained area with and without the rotating magnetic field. When the rotating magnetic field is applied, the fluorescence area shrinks from a large ellipse area at 5 mins to a small ellipse area at 30 mins. During this period, the brightness of the fluorescence stain increases, indicating that the microparticle swarm moves to the aggregation center and releases fluorescence. Note that due to the difference in the aggregation characteristics of the microparticles in the tangential and radial cross-sectional directions of the eyeball, the microparticles forms an elliptical pattern instead of a circle. The results of the control group show that when no magnetic actuation control is applied, the passive diffusion of fluorescence is weaker than that of actively propelled microparticles. Moreover, the distribution area is large and irregular. FIG. 24D shows the quantitative data of intensity and area of fluorescein used to simulate the drug release process. A reconstructed OCT image with slice-array images of the gathered microparticles is shown in FIG. 25.

Figure 26:
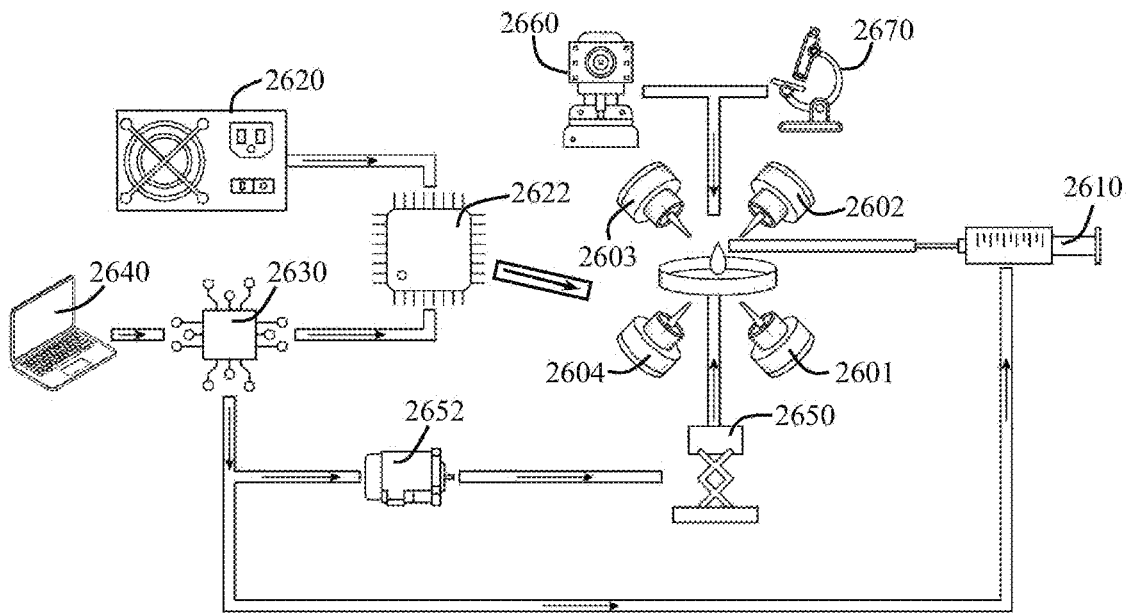
FIG. 26 illustrates a magnetic drive system in accordance with certain embodiments.

FIG. 26 illustrates a magnetic drive system in accordance with certain embodiments. The magnetic drive system includes four magnetic coils 2601, 2602, 2603, and 2604 to generate magnetic field in two orthogonal directions, four DC power supplies 2620 (AMETEK SGX300X17D-0ASAR) to generate high-power steady electrical voltage, one MCU 2630 (ATMEL MEGA32U4) included in a computer device 2640, and four voltage amplifiers 2622 controlled by MCU to transform DC current to the modified sinusoidal wave signals, such as what is shown in FIG. 7. The other components include a custom-designed chamber 2605, a microfluidic chip, an inverted optical CCD camera (THORLABS 1500 M-GE with objective lens from 2× to 10×), and OCT 2660 (THORLABS, Telesto™ Series), and a microscope 2670 that enables observation of microagent migration. The workspace of the magnetic field is located in the central area of the coil system, which is a square area with side length of 15 mm. A micro-injection device 2610 is provided to inject microagents into the workspace. Further, a drive device, such as a motor 2652, drives a lift platform 2650 such that the relative position of the workspace or working plane can be adjusted.

Consider a typical 2 D Helmholtz coil system with four coils where the first and third coils are in the positive and negative directions of the x-axis, and the second and fourth coils are in the positive and negative directions of the y-axis, respectively. The flux density of the rotating magnetic field is described as $B(t)=B_x\cos(2\pi ft)e_x+B_y\sin(2\pi ft)e_y$, where $e_x$ and $e_y$ denote the unit vectors in x and y directions respectively. For a Helmholtz coil system, $B_x$ is determined by the first and third coils. When current $I_1$ and $I_3$ of the first and third coils are reciprocal functions, expressed as $I_1=-I_3$, the superposition magnetic field $B_x$ is a unique vector field. Similarly, $I_2$ and $I_4$ are also reciprocal functions.

To generate a rotating gradient magnetic field, the two coils in the same direction should not be activated simultaneously. When $I_1>0$ and $I_3=0$, the direction of $B_x$ will point to the positive direction of the x-axis; when $I_1=0$ and $I_3>0$, the direction of $B_x$ will point to the negative direction of the x-axis. For $B_y$ on the y-axis, $I_2$ and $I_4$ are the same. This sequential activation process can be presented by Heaviside step function. Then, the current $I_i$ of the ith coil is presented in Equation (6).

Regarding microparticles and microrobots, by way of example, commercial spherical-shaped hematite microparticles (MagbeStar MP150FG-Plain, BEAVER Co., Ltd., China), with superparamagnetic core and polymer outsourcing layer with a diameter of 1 μm, are used for one or more in-vitro experiments. The microparticles can be loaded with various drugs via surface bonding. Commercial superparamagnetic iron oxide microparticles (SPIOm, Product 103 FG, NanoMicroTechnology Co., Ltd, China) are used for one or more ex-vivo experiments. The core of SPIOm is $Fe_3O_4$. The out layer of SPIOm is biocompatible polymers, and the fluorescein λmax absorption and λmax emission are 488 and 515 nm respectively. The particle size distribution (D50) is 0.5 μm. To adapt to high-viscosity environment, the microparticles can be processed with 1% Pluronic F-127 (Sigma Aldrich) in Deionized water solution as hydrophobic surface functionalization. The microrobots has a burr-like porous spherical structure and a diameter of 80 μm. They can be manufactured by a two-photon lithography system (Nanoscribe GmbH) using degradable materials doped with 2% superparamagnetic materials. Functional cells can be carried and delivered by such microrobots. The images of the microparticles and microrobots are shown in FIG. 16.

Regarding microfluidic chip design and fabrication, by way of example, a microfluidic chip is fabricated using soft-lithography technology. A four-inch-diameter silicon wafer is used as the substrate and spin-coated with a 100-μm-thick layer of negative photoresist SU-8 2050 (Microchem Corp.). After several processes, such as pre-bake, exposure, post-bake, and development, a SU-8 mold with a pattern of molded vascular microchannels is obtained. Appropriate amounts of polydimethylsiloxane (PDMS) (Sylgard 184, Dow Corning) and curing agent can are mixed at a ratio of 10:1 by weight and poured onto the SU-8 mold. The mold with PDMS mixture is placed in a vacuum oven and baked at 70° C. for 2 h after removing air bubbles. Finally, the cured PDMS microchannel is peeled off from the mold, punched at the inlet and outlets, and bonded with a clean glass substrate to form the final chip.

Regarding ex-vivo experiment on the bovine eyeball, by way of example, the bovine eyeball can be bought from local market and kept at 0° C.-4° C. environment. The fluorescein microparticle suspension with a volume of 1,000 μl is placed on a cell dish, mixed with 9 ml PBS (pH=7.6) buffer solution. After injecting 100 μl PBS buffer solution containing fluorescein microparticles into the eyeball using a micropipette, the eyeball incision is sealed with glue and then fixed on a custom-designed vibration chamber. Then, the eyeball with uniformly distributed fluorescein microparticles is placed in the operating area of the magnetic coil system. Before observation with OCT, the upper part of the eyeball can be removed. The eyeball is cut at its equator, excluding all other tissues (lens, cornea, pupil, iris, etc.) except the vitreous body. These images are taken with a complementary metal oxide semiconductor camera at a rate of 9-12 frames per second. After magnetic propulsion, the eyeball is cut with a scalpel, then the vitreous body is removed mechanically, and the retina is cut into a square (2 cm×2 cm). The fluorescence of the microparticles is excited by a light-emitting diode (Ts2R, Nikon eclipse) with a center wavelength of 488 nm. The experiment can be repeated three times or more.

Figure 27:
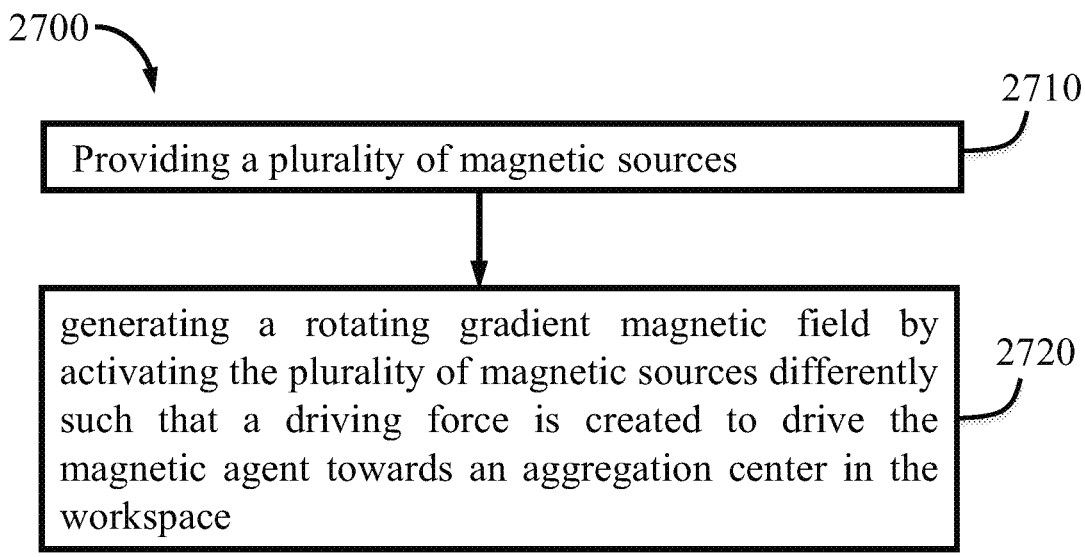
FIG. 27 is a flow chart illustrating a method for microagent control in accordance with certain embodiments.

FIG. 27 is a flow chart illustrating a method 2700 for controlling a microagent. The method 2700 can be used to control migration of a microagent or a swarm of microagents in a workspace. The microagent may be microparticle, microrobot, or other agents that can be magnetized.

Block 2710 states providing a plurality of magnetic sources. The magnetic sources can be activated to generate a magnetic field. The magnetic sources, when activated properly, can generated a rotating magnetic field. By way of example, the plurality of magnetic sources include magnetic coils, such as those as described with reference to FIG. 1, FIGS. 2A-2B or FIG. 26. The magnetic coils distribute evenly around the workspace and are energized sequentially with current input. The number of the magnetic sources can be determined according to practice needs. For example, there may be 2, 4, 6, 10, 12, 14, 18, or 20 magnetic sources.

Block 2720 states generating a rotating gradient magnetic field by activating the plurality of magnetic sources differently such that a driving force is created to drive the microagent towards an aggregation center in the workspace. By way of example, the method performs sequential activation for the plurality of magnetic sources such that direction of the rotating gradient magnetic field rotates. By way of example, the method adjusts position of the aggregation center by adjusting current input for the plurality of magnetic sources such that a magnetic flux density of the rotating gradient magnetic field in the workspace is adjusted. By way of example, the method adjusts position of the aggregation center by adjusting a rotating frequency at which the rotating gradient magnetic field rotates. By way of example, a workspace defines a working plane, and the plurality of magnetic sources defines a reference plane. The method adjusts position of the aggregation center by adjusting a height h of the working plane relative to the reference plane. By way of example, the method energizes a plurality of magnetic coils sequentially at a frequency f from respective DC power source. A current $I_i$ flowing through the ith magnetic coil is expressed as equation (1). The method adjusts position of the aggregation center by adjusting one or more of the amplitude I, the frequency f, and the current parameter.

By way of example, the method generates a mapping between the current parameter the aggregation center. The method solves motion functions with back propagation neural network (BPNN) model.

By way of example, the method controls migration of a swarm of microagents or microagent swarm in a workspace. The method generates a rotating gradient magnetic field by performing sequential activation for a plurality of magnetic sources such that a centripetal force is created to drive the microagent swarm towards an aggregation area in the workspace. The method increases size of the aggregation area by increasing a rotating frequency at which the rotating gradient magnetic field rotates. When the rotating frequency is less than a first threshold, the microagent swarm is in an aggregation state. When the rotating frequency is equal to or greater than the first threshold and is less than a second threshold, the microagent swarm is in an unstable state. When the rotating frequency is equal to or greater than the second threshold and is less than a second threshold, the microagent swarm is in a dispersion state. By way of example, the method further increases size of the aggregation area by increasing a height h of the working plane relative to the reference plane.

Figure 28:
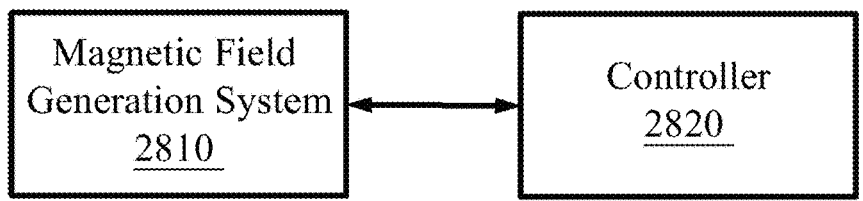
FIG. 28 illustrates an apparatus for controlling a microagent or a microagent swarm in accordance with certain embodiments.

FIG. 28 illustrates an apparatus for controlling a microagent or a microagent swarm. The apparatus, for example, can execute one or more methods as described above (such as the method 2700) or one or more steps of a method as described above. The apparatus, when operated, can control migration or navigation of a microagent or a microagent swarm in certain area or space. The certain area or space can be an environment inside or outside a human body. The certain area or space can be an industrial environment that is dangerous or harsh to humans or difficult for humans to access.

As illustrated, the apparatus includes a magnetic field generation system 2810 and a controller 2820. The magnetic field generation system 2810 generates a magnetic field. By way of example, the magnetic field generation system 2810 includes a plurality of magnetic sources, such as magnetic coils, and one or more power sources that energize the magnetic sources. In some embodiments, the magnetic field generation system 2810 includes other electrical components that performs one or more of functions including but not limited to signal filtration, rectification, conversion, amplification, comparison, etc.

The controller 2820 controls operation of the magnetic field generation system 2810 such that a rotating magnetic field can be generated to drive a microagent or a microagent swarm towards an aggregation center or aggregation area. For example, the controller 2820 can control the way of energization of the magnetic sources such that the magnetic sources are activated differently, such as sequentially, thereby rotating the magnetic field in a desirable way, such as at a desirable frequency. By way of example, the controller 2820 can control the rotating frequency of the magnetic field, the height of a working plane relative to a reference plane, one or more current parameters, etc. As a result, the migration behaviors, the location of the aggregation center or area, etc. of microagent or microagent swarm can be adjusted or controlled.

The controller 2820 can be implemented as a processor or processing unit of a computer device, such as a sever, a desktop, a tablet, a laptop, a smartphone, or the like, that communicates with the magnetic field generation system 2810 such that the magnetic field generation system 2810 can receive instructions from the controller 2820 and respond by following the same.

Figure 29:
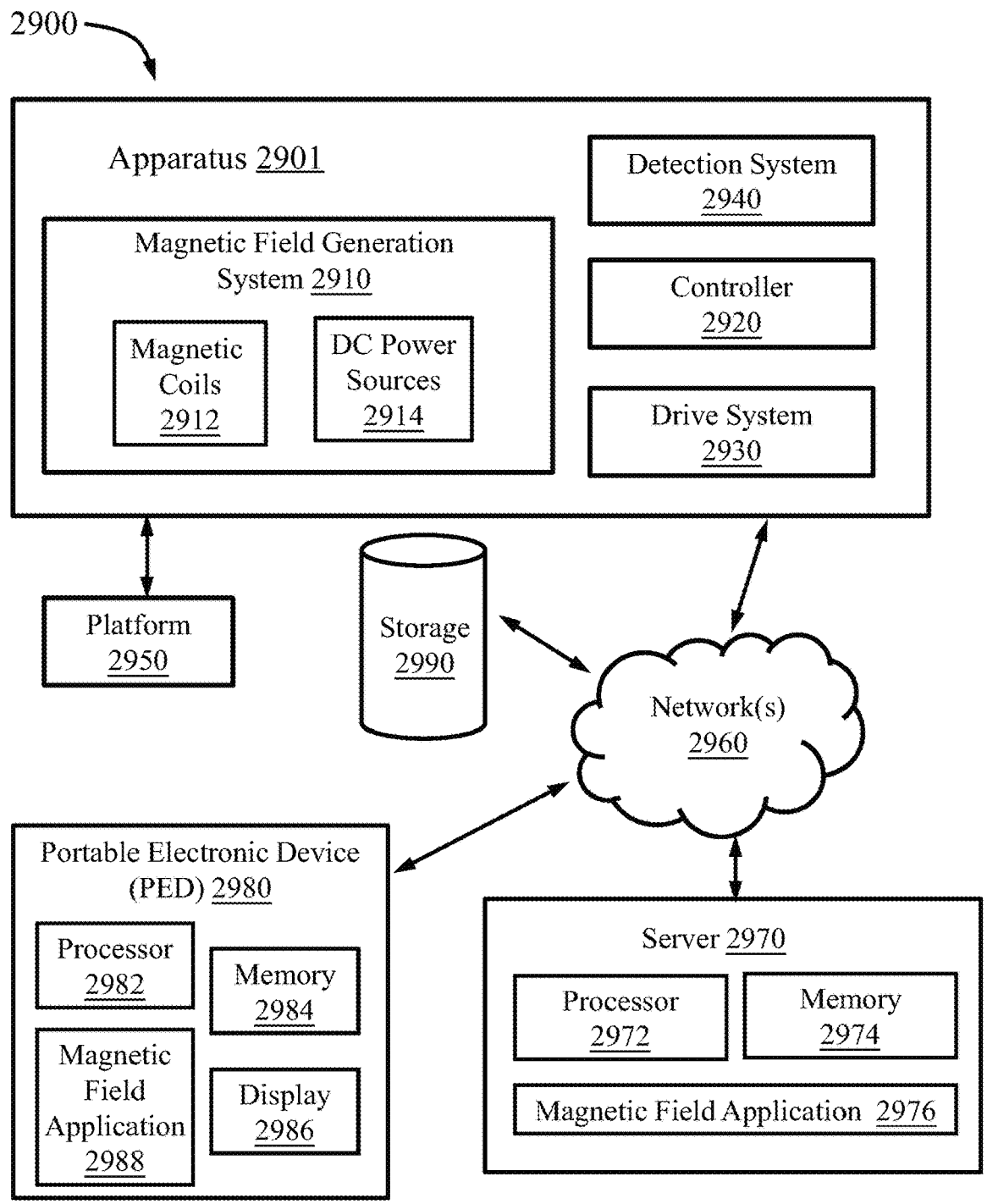
FIG. 29 illustrates a system for controlling a microagent or a microagent swarm in accordance with certain embodiments.

FIG. 29 illustrates a system 2900 for controlling a microagent or a microagent swarm. The system 2900, for example, can execute one or more methods as described above (such as the method 2700) or one or more steps of a method as described above.

As illustrated, the system 2900 includes an apparatus 2901 that includes a magnetic field generation system 2910 and a controller 2920. The magnetic field generation system 2910 can be a specific implementation of the magnetic field generation system 2810 with reference to FIG. 28. The controller 2920 can be a specific implementation of the controller 2820 with reference to FIG. 28.

By way of example, the magnetic field generation system 2910 includes multiple magnetic coils 2912 and DC power sources 2914 that energize the magnetic coils 2912. The controller 2920 controls the DC power sources 2914 such that the magnetic coils 2912 are activated differently. For example, the magnetic coils 2912 can be energized sequentially to create a rotating magnetic field. The rotating magnetic field generates a centripetal force for driving a microagent or a microagent swarm towards a target site. The rotating magnetic field generates a target site acting as an attraction center that attracts a microagent or a microagent swarm.

Optionally, the apparatus 2901 includes a drive system 2930, such as a motor and a transmission mechanism. The drive system 2930 can drive a platform 2950 for the microagent or microagent swarm, thereby changing positon of the workspace in the rotating magnetic field. The platform 2950 may be a human body, part of a human body, a microagent platform outside a human body, or a harsh environment in which microagents are expected to migrate to a target site to carry out a task in an industrial application.

Optionally, the apparatus 2901 includes a detection system 2940. The detection system 2940 includes one or more of sensors, cameras, etc. for collecting information related to microagent migration. The detection system 2940 facilitates monitoring of microagent or microagent swarm in a workspace. In some embodiments, optionally, the collected data by the detection system 2940 can be used in a feedback loop such that microagent migration can be adjusted timely or in a real-time manner. In this way, migration of microagent or swarm into the target site can be achieved more effectively, such as within a shorter time period, reaching the target site more accurately, etc.

Optionally, the apparatus 2901 can communicate one or more devices or systems via one or more networks 2960. As a result, microagent control can be achieved remotely. This is advantageous in applications where a close observation and control is difficult. For example, there may be scenarios where platform for carrying microagent or swarm must be kept in certain conditions, such as very low temperature or a limited space that is not easy to be accessed by operators or users.

By way of example, the system 2900 includes a server 2970 that communicates with the apparatus 2901 via one or more networks 2960. The server 2970 includes a processor or processing unit 2972 (such as one or more processors, microprocessors, and/or microcontrollers), one or more components of computer readable medium (CRM) or memory 2974, and a magnetic field application 2976. The memory 2974 stores instructions that when executed cause the processor 2972 to execute one or more methods as discussed herein, or one or more steps of a method as discussed herein.

In certain embodiments, optionally the system 2900 includes a portable electronic device or PED 2980 and a storage or memory 2990. The storage 2990 can include one or more of memory or databases that store one or more of image files, audio files, video files, software applications, and other information discussed herein. By way of example, the storage 2990 store image, instructions or software application that are retrieved by the server 2970 over the network 2960 such that one or more methods as discussed herein are executed, or one or more steps of a method as discussed herein are executed. For example, instructions for controlling the magnetic field generation system 2910 can be stored in the storage 2990 and retrieved by the server 2970 for execution. For example, the data collected by the detection system 2940 can be stored in the storage 2990 and retrieved by the server 2970.

The PED 2980 includes a processor or processing unit 2982 (such as one or more processors, microprocessors, and/or microcontrollers), one or more components of computer readable medium (CRM) or memory 2984, one or more displays 2986, and a magnetic field application 2988. The PED 2980 can execute one or more of methods as discussed herein or one or more steps of a method as discussed herein, and display an image related to microagent migration for review. Alternatively or additionally, the PED 2980 can retrieve files such as software instructions from the storage 2990 over the network 2960 and execute one or more methods as discussed herein or one or more steps of a method as discussed herein.

As used herein, a microagent is an agent with a size in a range of a few microns or less and can be magnetized. A microagent can be a microparticle or a microrobot, or the like.

The methods, apparatus, or systems in accordance with embodiments are provided as examples, and examples from one embodiment should not be construed to limit examples from another embodiment.

Unless otherwise defined, the technical and scientific terms used herein have the plain meanings as commonly understood by those skill in the art to which the example embodiments pertain. Embodiments are illustrated in non-limiting examples. Based on the above disclosed embodiments, various modifications that can be conceived of by those skilled in the art fall within scope of the example embodiments.

What is claimed is:

1. A method for controlling microagent in a workspace, comprising:
   providing a plurality of magnetic sources; and
   generating a rotating gradient magnetic field by activating the plurality of magnetic sources differently such that a driving force is created to drive the microagent towards an aggregation center in the workspace.

2. The method of claim 1, wherein the plurality of magnetic sources include magnetic coils that distribute evenly around the workspace and are energized sequentially with current input.

3. The method of claim 1, wherein generating the rotating gradient magnetic field includes performing sequential activation for the plurality of magnetic sources such that direction of the rotating gradient magnetic field rotates.

4. The method of claim 1, further comprising adjusting position of the aggregation center by adjusting current input for the plurality of magnetic sources such that a magnetic flux density of the rotating gradient magnetic field in the workspace is adjusted.

5. The method of claim 1, further comprising adjusting position of the aggregation center by adjusting a rotating frequency at which the rotating gradient magnetic field rotates.

6. The method of claim 1, wherein the workspace defines a working plane, and the plurality of magnetic sources define a reference plane, and wherein the method further comprises adjusting position of the aggregation center by adjusting a height h of the working plane relative to the reference plane.

7. The method of claim 1, wherein generating the rotating gradient magnetic field includes energizing a plurality of magnetic coils sequentially at a frequency f from respective direct current (DC) power source, and wherein a current $I_i$ flowing through the ith magnetic coil is expressed as:

$$I'_i = I \cdot \sin\left(2\pi\left(ft - \frac{i-1}{n}\right)\right) \cdot c_i$$

$$I_i = \begin{cases} I'_i & \text{when } I'_i \geq 0 \\ 0 & \text{when } I'_i < 0 \end{cases}$$

where I denotes an amplitude of current for the respective DC power source, t denotes time, $c_i$ denotes a current parameter for the ith magnetic coil.

8. The method of claim 7, further comprising: adjusting position of the aggregation center by adjusting one or more of the amplitude I, the frequency f, and the current parameter.

9. The method of claim 7, thither comprising: generating a mapping between the current parameter and the aggregation center.

10. The method of claim 9, wherein generating the mapping includes solving motion functions with back propagation neural network (BPNN) model.

11. A method for controlling migration of a microagent swarm in a workspace, the microagent swarm including a plurality of microagents, the method comprising:
generating a rotating gradient magnetic field by performing sequential activation for a plurality of magnetic sources such that a centripetal force is created to drive the microagent swarm towards an aggregation area in the workspace.

12. The method of claim 11, further comprising increasing size of the aggregation area by increasing a rotating frequency at which the rotating gradient magnetic field rotates.

13. The method of claim 12, wherein when the rotating frequency is less than a first threshold, the microagent swarm is in an aggregation state,
when the rotating frequency is equal to or greater than the first threshold and is less than a second threshold, the microagent swarm is in an unstable state,
when the rotating frequency is equal to or greater than the second threshold, the microagent swarm is in a dispersion state.

14. The method of claim 11, wherein the workspace defines a working plane, and the plurality of magnetic sources define a reference plane, and wherein the method further comprises increasing size of the aggregation area by increasing a height h of the working plane relative to the reference plane, the height h being a distance of the working plane and the reference plane in a direction perpendicular to the working plane and the reference plane.

15. The method of claim 11, wherein generating the rotating gradient magnetic field includes energizing a plurality of magnetic coils sequentially at a frequency f from respective direct current (DC) power source, and wherein current $I_i$, flowing through the ith magnetic coil is expressed as:

$$I'_i = I \cdot \sin\left(2\pi\left(ft - \frac{i-1}{n}\right)\right) \cdot c_i$$

$$I_i = \begin{cases} I'_i \text{ when } I'_i \geq 0 \\ 0 \text{ when } I'_i < 0 \end{cases}$$

where I denotes an amplitude of current for the respective DC power source, t denotes time, $c_i$ denotes a current parameter for the ith magnetic coil.

16. The method of claim 15, further comprising adjusting the aggregation area by adjusting the current parameter.

17. An apparatus of controlling a microagent in a workspace, comprising:
a magnetic field generation system that includes a plurality of magnetic sources for generating a rotating gradient magnetic field in the workspace; and
a controller that controls activation of the magnetic field generation system such that the rotating gradient magnetic field is generated for driving the microagent towards an aggregation center.

18. The apparatus of claim 17, further comprising a drive system that adjusts a relative position of a working plane relative to a reference plane defined by the magnetic field generation system.

19. The apparatus of claim 17, wherein the magnetic field generation system includes a plurality of magnetic coils and direct current (DC) power sources that energize the plurality of magnetic coils sequentially such that the rotating gradient magnetic field rotates at a rotating frequency.

20. The apparatus of claim 17, further comprising a detection system that detects migration of microagent in the workspace towards the aggregation center.

* * * * *